United States Patent
Kamm et al.

(10) Patent No.: US 9,261,496 B2
(45) Date of Patent: Feb. 16, 2016

(54) DEVICE FOR HIGH THROUGHPUT INVESTIGATIONS OF MULTI-CELLULAR INTERACTIONS

(75) Inventors: Roger Dale Kamm, Cambridge, MA (US); Haruhiko Harry Asada, Cambridge, MA (US); Waleed Ahmed Farahat, Newton, MA (US); Ioannis K. Zervantonakis, Cambridge, MA (US); Levi B. Wood, Cambridge, MA (US); Chandrasekhar Kothapalli, Cleveland, OH (US); Seok Chung, Seoul (KR); Jeffrey D. Macklis, Brookline, MA (US); Suzanne Tharin, Palo Alto, CA (US); Johanna Varner, Salt Lake City, UT (US); Young Kum Park, Singapore (SG); Kwang Ho Lee, Seoul (KR); Le Thanh Tu Nguyen, Lausanne Vaud (CH); Choong Kim, Singapore (SG)

(73) Assignees: Massachusetts Institute of Technology, Cambridge, MA (US); The General Hospital Corporation, Boston, MA (US); The Brigham and Women's Hospital, Inc., Boston, MA (US); Children's Medical Center, Corp., Boston, MA (US)

( * ) Notice: Subject to any disclaimer, the term of this patent is extended or adjusted under 35 U.S.C. 154(b) by 0 days.

(21) Appl. No.: 13/876,293

(22) PCT Filed: Sep. 29, 2011

(86) PCT No.: PCT/US2011/054029
§ 371 (c)(1),
(2), (4) Date: Oct. 4, 2013

(87) PCT Pub. No.: WO2012/050981
PCT Pub. Date: Apr. 19, 2012

(65) Prior Publication Data
US 2014/0057311 A1    Feb. 27, 2014

Related U.S. Application Data

(60) Provisional application No. 61/394,624, filed on Oct. 19, 2010, provisional application No. 61/387,674, filed on Sep. 29, 2010.

(51) Int. Cl.
| | |
|---|---|
| *C12M 1/34* | (2006.01) |
| *C12M 3/00* | (2006.01) |
| *G01N 33/50* | (2006.01) |
| *B01L 3/00* | (2006.01) |
| *C12M 3/06* | (2006.01) |
| *C12M 1/00* | (2006.01) |
| *C12M 1/12* | (2006.01) |

(52) U.S. Cl.
CPC ...... *G01N 33/5008* (2013.01); *B01L 3/502753* (2013.01); *C12M 23/16* (2013.01); *C12M 23/22* (2013.01); *C12M 25/14* (2013.01); *C12M 29/04* (2013.01); *G01N 33/5011* (2013.01); *G01N 33/5029* (2013.01); *G01N 33/5058* (2013.01); *G01N 33/5064* (2013.01); *B01L 2200/0668* (2013.01); *B01L 2300/069* (2013.01); *B01L 2300/0681* (2013.01); *B01L 2300/0816* (2013.01)

(58) Field of Classification Search
CPC .......... G01N 35/025; G01N 35/00029; G01N 33/5011; G01N 33/5088; G01N 33/5029; G01N 33/5058; G01N 33/5064; C12M 23/08; C12M 23/16; C12M 23/22; C12M 25/14; C12M 41/14; C12Q 1/04; C12Q 1/18; C12Q 1/02; C12N 5/0012; C12N 2533/54; C12N 2533/74; A61K 35/12; A61K 48/00; C23F 1/02; C04B 41/009; C04B 41/91; B01L 2200/12; B01L 2200/0689; B01L 2200/0668; B01L 2300/0681; B01L 2300/069; B01L 2300/0816; B01L 3/502753
See application file for complete search history.

(56) References Cited

U.S. PATENT DOCUMENTS

| | | | |
|---|---|---|---|
| 2005/0147960 | A1 | 7/2005 | Levinson et al. |
| 2006/0154361 | A1 | 7/2006 | Wikswo et al. |
| 2006/0199260 | A1* | 9/2006 | Zhang et al. ............... 435/293.1 |
| 2007/0269476 | A1 | 11/2007 | Voytik-Harbin et al. |
| 2008/0233607 | A1* | 9/2008 | Yu et al. ........................... 435/29 |
| 2010/0002929 | A1 | 1/2010 | Sammak et al. |
| 2010/0028999 | A1 | 2/2010 | Nain |
| 2011/0159522 | A1* | 6/2011 | Kamm et al. ................ 435/7.21 |

FOREIGN PATENT DOCUMENTS

| | | |
|---|---|---|
| WO | WO 2006/052223 A1 | 5/2006 |
| WO | WO 2008/079320 A1 | 7/2008 |
| WO | WO 2009/012449 A1 | 1/2009 |
| WO | WO 2009/048435 A1 | 4/2009 |
| WO | WO 2009/089189 A2 | 7/2009 |
| WO | WO 2009/126524 A2 | 10/2009 |
| WO | WO 2010/009307 A2 | 1/2010 |
| WO | WO 2010/036912 A2 | 4/2010 |
| WO | WO 2010/101708 A2 | 9/2010 |
| WO | WO 2010/124207 A1 | 10/2010 |
| WO | WO 2011/044116 A2 | 4/2011 |

OTHER PUBLICATIONS

Barallobre, M.J., et al., "The Netrin Family of Guidance Factors: Emphasis on Netrin-1 Signalling", *Brain Res Brain Res Rev.*, 49: 22-47 (2005).

Bareyre, F.M., et al, "Transgenic Labeling of the Corticospinal Tract for Monitoring Axonal Responses to Spinal Cord Injury", *Nat. Med.*, 11(12): 1355-1360 (2005).

Bently, D. and Toroian-Raymond, A., "Disoriented Pathfinding by Pioneer Neurone Growth Cones Deprived of Filopodia by Cytochalasin Treatment", *Nature*, 323 (6090): 712-715 (1986).

Brånemark, P.I., "Capillary Form and Function. The Microcirculation of Granulation Tissue.", *Bibl. Anat.*, 7: 9-28 (1965).

Chaw, K.C., et al., "Multi-Step Microfluidic Device for Studying Cancer Metastasis", *Lab Chip*, 7(8): 1401-1407 (2007).

Chung, S., et al., "Surface-Treatment-Induced Three-Dimensional Capillary Morphogenesis in a Microfluidic Platform", *Adv Mater*, 21(47):4863-4867 (2009).

Cooper, H.M., et al., "The Deleted in Colorectal Cancer Netrin Guidance System: A Molecular Strategy for Neuronal Navigation", *Clin Exp Pharmacol Physiol*, 26(9): 749-751 (1999).

Fischbach, C., et al., "Engineering Tumors With 3D Scaffolds", *Nature Methods*, 4(10):855-860 (2007).

Frame, M.C., "SRC in Cancer: Deregulation and Consequences for Cell Behaviour", *Biochini Biophys Acta*, 1602(2): 114-130 (2002).

Galbraith, C.G., et al., "Shear Stress Induces Spatial Reorganization of the Endothelial Cell Cytoskeleton", Cell Motil Cytoskeleton, 40(4): 317-330 (1998).

Joosten, E.A., et al., "Induction of Corticospinal Target Finding by Release of a Diffusible Chemotrophic Factor in Cervical Spinal Grey Matter", *Neuroscience Letters*, 128: 25-28 (1991).

Kang, J.H., et al., "Fabrication of a Poly(dimethylsiloxane) Membrane With Well-Defined Through-Holes for Three Dimensional Microfluidic Networks",*Journal Of Micromechanics and Microengineering*, 49(4): 045027 (2009).

Kennedy, T.E., "Cellular Mechanisms of Netrin Function : Long-Range and Short-Range Actions", *Biochem Cell Biol.*, 78(5): 569-575 (2000).

Kuang, R.Z. and Kalil, K., "Development of Specificity in Corticospinal Connections by Axon Collaterals Branching Selectively Into Appropriate Spinal Targets", *J. Comp Neurol*, 344(2): 270-282 (1994).

Li, G.N., et al.,"Multi-Molecular Gradients of Permissive and Inhibitory Cues Direct Neurite Outgrowth",*Ann Biomed Eng*, 36(6): 889-904 (2008).

Lin, L., et al., "Surface-Bound Microenclosures for Biomolecules", *Angew Chem Int Ed Engl.*, 49(50):9773-9776 (2010).

Liu, T., et al., "A Microfluidic Device for Characterizing the Invasion of Cancer Cells in 3-D Matrix", *Electrophoresis*, 30(24): 4285-4291 (2009).

Margulies, S.S., et al., "Physical Model Simulations of Brain Injury in the Primate", *J Biomech*, 23(8): 823-836 (1990).

O'Leary, D.D. and Terashima, T., "Cortical Axons Branch to Multiple Subcortical Targets by Interstitial Axon Budding: Implications for Target Recognition and 'Waiting Periods'", *Neuron*, 1(10): 901-910 (1998).

Pedersen, J.A. and Swarz, M.A., "Mechanobiology in the Third Dimension", *Ann Biomed Eng.*, 33(11): 1469-1490 (2005).

Peinado, H. and Cano, A., "A Hypoxic Twist in Metastasis", *Nature Cell Biology*, 10(3):253-254 (2008).

Sakai, Y., et al., "Embryoid Body Culture of Mouse Embryonic Stem Cells Using Microwell and Micropatterned Chips", *J Biosci Bioeng*, 111:85-91 (2011).

Saltzman, W.M., et al., "Three-Dimensional Cell Cultures Mimic Tissues", *Ann N.Y. Acad Sci.*, 665: 259-273 (1992).

Stanfield, B.B., "The Development of the Corticospinal Projection", *Prog Neurobiol*, 38(2): 169-202 (1992).

Strell, C., et al., "Surface Molecules Regulating Rolling and Adhesion to Endothelium of Neutrophil Granulocytes and MDS-MB-468 Breast Carcinoma Cells and Their Interaction", *Cell Mol. Life Sci.*, 64(24): 3306-3316 (2007).

Takuma, H., et al., "In Vitro Formation of Corticospinal Synapses in an Organotypic Slice Co-Culture", *Neuroscience*, 109(2): 359-370 (2002).

Tourovskaia, A., et al., "Long-Term Micropatterned Cell Cultures in Heterogeneous Microfluidic Environments", *Conf Proc. IEEE Eng Med Biol Soc.*, 4:2675-2678 (2004).

Wagner, Jr., F.C. and Dohrmann, G.J., "Alterations in Nerve Cells and Myelinated Fibers in Spinal Cord Injury", *Surg Neurol*, 3(3): 125-131 (1975).

Wan, C.R., et al., "Differentiation of Embryonic Stem Cells Into Cariomyocytes in a Compliant Microfluidic System", *Ann Biomed Eng*, 39(6):1840-1847 (2011).

Wang, D.M. and Tarbell, J.M., "Modeling Interstitial Flow in an Artery Wall Allows Estimation of Wall Shear Stress on Smooth Muscle Cells", *J Biomech Eng*, 117(3): 358-363 (1995).

Wehrle, R., et al., "Expression of Netrin-1, Slit-1 and Slit-3 But Not Slit-2 After Cerebellar and Spinal Cord Lesions", *Eur J Neurosci.*, 22(9): 2134-2144 (2005).

Arlotta, P., et al., "Neuronal Subtype-Specific Genes That Control Corticospinal Motor Neuron Development In Vivo", *Neuron*, 45: 207-221 (2005).

Bardi, G., et al., "Rho Kinase Is Required for CCR7-Mediated Polarization and Chemotaxis of T Lymphocytes", *FEBS Letters*, 542: 79-83 (2003).

Boardman, K.C. and Swartz, M.A., "Interstitial Flow As a Guide for Lymphangiogenesis", *Circ. Res.*, 92: 801-808 (2003).

Borselli, C., et al., "Induction of Directional Sprouting Angiogenesis by Matrix Gradients",*J Biomed Mater Res*, 810A:297-305 (2007).

Brose, K., et al., "Slit Proteins Bind Robo Receptors and Have an Evolutionary Conserved Role in Repulsive Axon Guidance", *Cell*, 96: 795-806 (1999).

Buck, K.B. and Zheng, J.Q., "Growth Core Turning Induced by Direct Local Modification of Microtubule Dynamics", *The Journal of Neuroscience*, 22(21): 9358-9367 (2002).

Bunge, M.B., "Novel Combination Strategies to Repair the Injured Mammalian Spinal Cord", *The Journal of Spinal Cord Medicine*, 31(3): 262-269 (2008).

Catapano, L.A., et al., "Specific Neurotrophic Factors Support the Survival of Cortical Projection Neurons At Distinct Stages of Development", *The Journal of Neuroscience*, 21(22): 8863-8872 (2001).

Catapano, L.A., et al., "Stage-Specific and Opposing Roles of BDNF, NT-3 and bFGF in Differentiation of Purified Callosal Projection Neurons Toward Cellular Repair of Complex Circuitry", *European Journal of Neuroscience*, 19: 2421-2434 (2004).

Causeret, F., et al., "Slit Antagonizes Netrin-1 Attractive Effects During the Migration of Inferior Olivary Neurons", *Developmental Biology*, 246: 429-440 (2002).

Chang, S.F., et al., "Tumor Cell Cycle Arrest Induced by Shear Stress: Roles of Integrins and Smad", *PNAS*, 105(10): 3927-3932 (2008).

Chen, H., et al., "Semaphorin-Neuropilin Interactions Underlying Sympathetic Axon Responses to Class III Semaphorins", *Neuron*, 21: 1283-1290 (1988).
Chueh, B.-H., et al., "Leakage-Free Bonding of Porous Membranes Into Layered Microfluidic Arrays Systems", *Anal Chem*, 79(9):3504-3508 (2007).
Chung, B.G., et al., "A Hybrid Microfluidic-Vacumn Device for Direct Interfacing With Conventional Cell Cuture Methods", *BMC Biotechnology*, 7(60): 7 pages (2007).
Chung, S., et al., "Cell Migration Into Scaffolds Under Co-Culture Conditions in a Microfluidic Platform", *Lab Chip*, 9: 269-275 (2009).
Chung, S., et al., "Microfluidic Platforms for Studies of Angiogenesis, Cell Migration, and Cell-Cell Interactions", *Annals of Biomedical Engineering*, 38(3): 1164-1177 (2010).
Cukierman, E., et al., "Taking Cell-Matrix Adhesions to the Third Dimension", *Science*, 294: 1708-1712 (2001).
Curinga, G. and Smith, G.M., "Molecular/Genetic Manipulation of Extrinsic Axon Guidance Factors for CNS Repair and Regeneration", *Exp. Neurol.*, 209(2): 333-342 (2008).
Curti, B.D., et al., "Interstitial Pressure of Subcutaneous Nodules in Melanoma and Lymphoma Patients: Changes During Treatment", *Cancer Research*, 53: 2204-2207 (1993).
Dertinger, S.K.W., et al, "Gradients of Substrate-Bound Laminin Orient Axonal Specification of Neurons", *PNAS*, 99(20): 12542-12547 (2002).
Dickson, B.J., "Molecular Mechanisms of Axon Guidance", *Science*, 298: 1959-1964 (2002).
Eide, B. L., et al., Identification of Try-397 As the Primary Site of Tyrosine Phosphorylation and $pp60^{src}$ Association in the Focal Adhesion Kinase, $pp125^{FAK}$, *Molecular and Cellular Biology*, 15(5): 2819-2827 (1995).
El-Ali, J., et al., "Cells on Chips", *Nature*, 442, 403-411 (2006).
Feraud, O., et al., "Embryonic Stem Cell-Derived Embryoid Bodies Development in Collagen Gels Recapitulates Sprouting Antiogenesis", *Laboratory Investigation*, 18(12):1669-1681 (2001).
Finchmam, V.J. and Frame, M.C., "The Catalytic Activity of Src Is Dispensable for Translocation to Focal Adhesions But Controls the Turnover of These Structures During Cell Motility", *The EMBO Journal*, 17(1): 81-92 (1998).
Fluery, M.E., et al., "Autologous Morphogen Gradients by Subtle Interstitial Flow and Matrix Interactions", *Biophysical Journal*, 91: 113-121 (2006).
Folch, A. and Toner, M., "Microengineering of Cellular Interactions", *Annu. Rev. Biomed. Eng.*, 2: 227-256 (2000).
Francisco, H., et al., "Regulation of Axon Guidance and Extension by 3-Dimensonal Constraints", *Biomaterials*, 28(23): 3398-3407 (2007).
Fried, J., et al., "Cytotoxic and Cytokinetic Effects of Thymidine, 5-Fluorouacil, and Deoxycytidine on HeLa Cells in Culture", *Cancer Research*, 41: 2627-2632 (1981).
Friedl, P., et al., "Migration of Coordinated Cells Clusters in Mesenchymal and Epithelial Cancer Explants In Vitro", *Cancer Research*, 55: 4557-4560 (1995).
Galbraith, C.G., et al., "The Relationship Between Force and Focal Complex Development", *The Journal of Cell Biology*, 159(4): 695-705 (2002).
Genç, B., et al, "A Chemoattractant Role for NT-3 in Proprioceptive Axon Guidance", *PLOS Biology*, 2(12): 2112-2121 (2004).
Gerhardt, H., et al., "VEGF Guides Angiogenic Sprouting Utilizing Endothelial Tip Cell Filopodia", *The Journal of Cell Biology*, 161(6):1163-1177 (2003).
Goodhill, G.J., "Mathematical Guidance for Axons", *Trends in Neuroscience*, 21(6): 226-231 (1998).
Goodhill, G.J. and Urbach, J.S., "Theoretical Analysis of Gradient Detection by Growth Cones", *J. Nerubiol*, 41: 230-241 (1999).
Griffith, L.G. and Swartz, M.A., "Capturing Complex 3D Tissue Physiology In Virtro", *Nature Reveiws Molecular Cell Biology*, 7: 211-224 (2006).
Han, Q., et al., "Multidimensional Analysis of the Frequencies and Rates of Cytokine Secretion From Single Cells by Quantitative Microengraving", *Lab Chip*, 10(11): 1391-1400 (2010).

Helm, C.L.E., et al., "Synergy Between Interstitial Flow and VEGF Directs Capillary Morphogenesis In Vitro Through a Gradient Amplification Mechanism", *PNAS*, 102(44): 1577915784 (2005).
Helmke, B.P., "Rapid Displacement of Vimentin Intermediate Filaments in Living Endothelial Cells Exposed Cells Exposed to Flow", *Circulation Research*, 86: 745-752 (2000).
Huang, C.P., et al., "Engineering Microscalc Cellular Niches for Three-Dimensional Multicellular co-Cultures", *Lab Chip*, 9: 1740-1748 (2009).
Jalali, S., et al., "Shear Stress Activates p6Osrc-Ras-MAPK Signaling Pathways in Vascular Endothelial Cells", *Arterioscler Thromb Vasc Biol*, 18: 227-234 (1998).
Jarjour, A.A., et al., "Netrin-1 Is a Chemorepellent for Oligodendrocyte Precursor Cells in the Embryonic Spinal Cord", *The Journal of Neuroscience*, 23(9): 3735-3744 (2003).
Jcon, N.L., et al., "Generation of Solution and Surface Gradients Using Microfluidic Systems", *Langmuir*, 16: 8311-8316 (2000).
Joosten, E.A.J., et al., "Tropism and Corticospinal Target Selection in the Rat", *Neuroscience*, 59: 33-41 (1994).
Keenan, T.M., et al., "Micorfluidic 'jets' for Generating Steady-State Gradients of Soluble Molecules on Open Surfaces", *Applied Physics Letter*, 89: 114103-01-114103-03 (2006).
Keenan, T.M. and Folch, A., "Biomolecular Gradients in Cell Culture Systems", *Lab Chip*, 8: 94-57 (2008).
Keino-Masu, K., et al., "Deleted in Colorectal Cancer (DCC) Encodes a Netrin Receptor", *Cell*, 87: 175-185 (1996).
Khademhosseini, A., et al., "Cell Docking Inside Microwells Within Reversibly Sealed Microfluidic Channels for Fabricating Multiphenotype Cell Arrays", *Lab Chip*, 5:1380-1386 (2005).
Kong, F., et al., "Demonstration of Catch Bonds Between an Integrin and Its Ligand", *The Journal of Cell Biology*, 185(7): 1275-1284 (2009).
Lang, S., et al., "Growth Cone Response to Ephrin Gradients Produced by Microfluidic Networks", *Anal Bioannal Chem*, 390: 809-816 (2008).
Lawler, K., et al., "Mobility and Invasiveness of Metastatic Esophageal Cancer Are Potentiated by Shear Stress in a ROCK-And Ras-Dependent Manner", *Am J Physiol Cell Physiol*, 291: C668-C677 (2006).
Lee, K.H., et al., "Hydrophilic Electrospun Polyurethane Nanofiber Matrices for hMSC Culture in a Microfluidic Cell Chip", *Journal of Biomedical Materials Research Part A*, 90A:619-628 (2009).
Lee, K.H., et al., "Polymeric Nanofiber Web-Based Artificial Renal Microfluidic Chip", *Biomed Microdevices*, 9:435-442 (2007).
Li, G.N., et al., "Tissue-Engineered Platform of Axon Guidance", *Tissue Engineering: Part B*, 4(1): 33-51 (2008).
Li, H.S., et al., "Vertebrated Slit, a Secreted Ligand for the Transmembrane Protein Roundabout, Is a Repellent for Olfactory Bulb Axons", *Cell*, 96: 807-818 (1999).
Li, N., et al., "Biology on a Chip: Microfabrication for Studying the Behaviour of Cultured Cells", *Crical Review in Biomedical Engineering*, 31(5&6): 423-488 (2003).
Li, S., et al., "Fluid Shear Stress Activation of Focal Adhesion Kinase", *The Journal of Biological Chemistry*, 272(48): 30455-30465 (1997).
Li, S., et al., "The Role of the Dynamics of Focal Adhesion Kinase in the Mechanotaxis of Endothelial Cells", *PNAS*, 99(6): 3546-3551 (2002).
Li, S., et al., "Mechanotransduction in Endothelial Cell Migration", *Journal of Cellular Biochemistry*, 96: 1110-1126 (2005).
Lin, S., et al., "In-Situ Measurement of Cellular Microenvironments in a Microfluidic Device", *Lab Chip*, 9:257-262 (2009).
Lo, C.M., et al., "Cell Movement Is Guided by the Rigidity of the Substrate", *Biophysical Journal*, 79: 144-152 (2000).
Love, J.C., et al., "A Microengraving Method for Rapid Selection of Single Cells Producing Antigen-Specific Antibodies", *Nature Biotechnology*, 24(6):703-707 (2006).
Luo, Y. and Zare, R.N., "Perforated Membrane Method for Fabricating Three-Dimensional Polydimethylsiloxane Microfluidic Devices", *Lab Chip*, 8:1688-1694 (2008).
Magavi, S.S., et al., "Induction of Neurogenesis in the Neocortex of Adult Mice", *Nature*, 405: 951-955 (2000).

McDonald, J.C., et al., "Fabrication of Microfluidic Systems in Poly(dimethylsiloxane)", *Electrophoresis*, 21: 27-40 (2000).

Meijering, E., et al., "Design and Validation of a Tool for Neurite Tracing and Analysis in Fluorescence Microscopy Images", *Cytometry Part A*, 58A:167-176 (2004).

Millet, L.J., et al., "Guiding Neuron Development With Planar Surface Gradients of Substrate Cues Deposited Using Microfluidic Devices", *Lab Chip*, 10(12): 1525-1535 (2010).

Mitchell, K.J., et al., "Genetic Analysis of Netrin Genes in Drosophila: Netrins Guide CNS Commissural Axons and Peripheral Motor Axons", *Neuron*, 17: 203-215 (1996).

Moldovan, N. T., et al., "Contribution of Monocytes/Macrophages to Compensatory Neovascularization. The Drilling of Metalloelastase-Positive Tunnels in Ischemic Myocardium", *Circulation Research*, 87: 378-384 (2000).

Molyneaux, B.J., et al., "Fezl Is Required for the Birth and Specification of Corticospinal Motor Neurons", *Neuron*, 47: 817-831 (2005).

Mortimer, D., et al, "Growth Cone Chemotaxis", *Trends in Neurosciences*, 31(2): 90-98 (2008).

Nakatsu, M.N., et al., "Angiogenic Sprouting and Capillary Lumen Formation Modeled by Human Umbilical Vein Endothelial Cells (HUVEC) in Fibrin Gels: the Role of Fibroblasts and Angiopoietin-1", *Microvascular Research*, 66:102-112 (2003).

Ng, C.P. and Swartz, M.A., "Fibroblast Alignment Under Interstitial Fluid Flow Using a Novel 3D Tissue Culture Model", *Am J Physiol Hear Circ Physiol.*, 28: H1771-H1777 (2003).

Ng, C.P., et al., "Interstitial Fluid Flow Induces Myofibroblast Differentiation and Collagen Alignment In Vitro", *Journal of Cell Science*, 118(20): 4731-4739 (2005).

Ozdinler, P.H. and Macklis, J.D., "IGF-I Specifically Enhances Axon Outgrowth of Corticospinal Motor Neurons", *Nature Neuroscience*, 9(11): 1371-1381 (2006).

Park, J. W., et al., "Microfluidic Culture Platform for Neuroscience Research", *Nature Protocols*, 1(4): 2128-2136 (2006).

Park, Y.K., et al., "A Simple Three-Dimensional Microfluidic Platform for Tracking Stem Cell Fate Within Differently Engineered Microenvironments As a Basis for Drug Screening", Electronic Supplementary Information for Lab on a Chip—4 pages—no date provided.

Parsa, H., et al., "Uncovering the Behaviours of Individual Cells Within a Multicellular Microvascular Community", *PNAS*, 108(12):5133-5138 (2011).

Pedersen, J. A., et al., "Cells in 3D Matrices Under Interstitial Flow: Effects of Extracellular Matrix Alignment on Cell Shear Stress and Drag Forces", *Journal of Biomechanics*, 43: 900-905 (2010).

Piper, M., et al., "Signaling Mechanisms Underlying Slit2-Induced Collapse of Xenopus Retinal Growth Cones", *Neuron*, 49: 215-228 (2006).

Plump, A.S., et al., "Slit1 and Slit2 Cooperate to Prevent Premature Midline Crossing of Retinal Axons in the Mouse Visual System", *Neuron*, 33: 219-232 (2002).

Polacheck, W.J., et al., "Interstitial Flow Influences Direction of Tumor Cell Migration Through Competing Mechanisms", *PNAS*, 108(27):1115-11120 (2011).

Pujic, Z., et al., "Analysis of the Growth Cone Turning Assay for Studying Axon Guidance", *Journal of Neuroscience Methods*, 170: 220-228 (2008).

Raub, C.B., et al., "Predicting Bulk Mechanical Properties of Cellularized Collagen Gels Using Multiphoton Microscopy", *Acta Biomater*, 6(12):4657-4665 (2010).

Renault, J.P., et al., "Fabricating Microarrays of Functional Proteins Using Affinity Contact Printing", *Angew Chem Int Ed*, 41(13):2320-2323 (2002).

Riol-Blanco, L, et al., "The Chemokine Receptor CCR7 Activates in Dendritic Cells Two Signaling Modules That Independently Regulate Chemotaxis and Migratory Speed", *The Journal of Immunology*, 174: 4070-4080 (2005).

Rosenthal, A., et al., "Cell Patterning Chip for Controlling the Stem Cell Microenvironment", *Biomaterials*, 28(21): 3208-3216 (2007).

Rosoff, W., et al., "A New Chemotaxis Assay Shows the Extreme Sensitivity of Axons to Molecular Gradients", *Nature Neuroscience*, 7(6): 678-682 (2004).

Schaff, U.Y., et al., "Vascular Mimetics Based on Microfluidics for Imaging the Leukocyte-Endothelial Inflammatory Response", *Lab Chip*, 7:448-456 (2007).

Schaller, M.D., et al., "Autophosphorylation of the Focal Adhesion Kinase, pp125$^{FAK}$, Directs SH2-Dependent Binding of pp60$^{src}$", *Molecular and Cellular Biology*, 14(3): 1680-1688 (1994).

Serafini, T., et al., "The Netrins Define a Family of Axon Outgrowth-Promoting Proteins Homologous to C. Elegans UNC-6", *Cell*, 78: 409-424 (1994).

Serini, G., et al., "Modeling the Early Stages of Vascular Network Assembly", *The EMBO Journal*, 22(8):1771-1779 (2003).

Shields, J.D., et al., "Autologous Chemotaxis As a Mechanism of Tumor Cell Homing to Lyphatics Via Interstitial Flow and Autocrine CCR7 Signaling", *Cancer Cell*, 11: 526-538 (2007).

Shyy, J.Y.J. and Chien, S., "Role of Integrins in Endothelial Mechanosensing of Shear Stress", *Circulation Research*, 91: 769-775 (2002).

Sieg, D.J., et al., "Pyk2 and Src-Family Protein-Tyrosine Kinases Compensate for the Loss of FAK in Firbronectin-Stimulated Signaling Events But Pyk2 Does Not Fully Function to Enhance FAK Cell Migration", *The EMBO Journal*, 17(20): 5933-5947 (1998).

Stein, E. and Tessier-Lavigne, M., "Hierarchial Organization of Guidance Receptors: Silencing of Netrin Attraction by Slit Through a Robo/DCC Receptor Complex", *Science*, 291: 1928-1938 (2001).

Taylor, A.M., et al., "A Microfluidic Culture Platform for CNS Axonal Injury, Regeneration and Transport", *Nature Methods*, 2(8): 599-605 (2005).

Taylor, A.M., et al., "Microfluidic Local Perfusion Chambers for the Visualization and Manipulation of Synapses", *Neuron*, 66: 57-68 (2010).

Tessier-Lavigne, M. and Goodman, C.S., "The Molecular Biology of Axon Guidance", *Science*, 274(5290): 1123-1133 (1996).

Thomas, J.W., et al., "SH2- and SH3-Mediated Interactions Between Focal Adhesion Kinase and Src", *The Journal of Biological Chemistry*, 273(1): 577-583 (1998).

Toh, Y.-C., et al., "A Novel 3D Mammalian Cell Perfusion-Culture System in Microfluidic Channels", *Lab Chip*, 7:302-309 (2007).

Urbach, J.S. and Goodhill, G.J., "Limitations on Detection of Gradients of Diffusible Chemicals by Axons", *Neurocomputing*, 26-27: 39-43 (1999).

Vickerman, V., et al., "Design, Fabrication and Implementation of a Novel Multi Parameter Control Microfluidic Platform for Three-Dimensional Cell Culture and Real-Time Imaging", *Lab Chip*, 8(9): 1468-1477 (2008).

Wang, N., et al., "Mechanotransduction Across the Cell Surface and Through the Cytoskeleton", *Science*, 260(5111): 1124-1127 (1993).

Wang, S. and Tarbell, J.M., "Effect of Fluid Flow on Smooth Muscle Cells in a 3-Dimensional Collagen Gel Model", *Arteriosler Thromb Vasc Biol*, 20: 2220-2225 (2000).

Ward, M.E., et al., "Regulated Formation and Selection of Neuronal Processes Underlie Directional Guidance of Neuronal Migration", *Molecular and Cellular Neuroscience*, 30: 378-387 (2005).

Whitesides, G.M., "The Origins and the Future of Microfluidics", *Nature*, 442: 368-373 (2006).

Wilbur, J.D., et al., "Microcontact Printing of Self-Assembled Monolayers: Applications in Microfabrication", *Nanotechnology*, 7:452-457 (1996).

Willson, C.A., et al., "Upregulation of EphA Receptor Expression in the Injured Adult Rat Spinal Cord", *Cell Transplantation*, 11: 229-239 (2002).

Wood, L.B., et al., "A Stochastic Broadcast Feedback Approach to Regulating Cell Population Morphology for Microfluidic Angiogenesis Platforms", *IEEE Transactions on Biomedical Engineering*, 56(9):2299-2303 (2009).

Wu, W., et al., "Directional Guidance of Neuronal Migration in the Olfactory System by the Protein Slit", *Nature*, 400(6742): 331-336 (1999).

Xia, Y. and Whitesides, G.M., "Soft Lithography", *Annu. Rev. Mater. Sci.*, 38: 153-184 (1998).

Xu, J., et al., "Adaptation Is Not Required to Explain the Long-Term Response of Axons to Molecular Gradients", *Development*, 132: 4545-4552 (2005).

Yamamura, N., et al., "Effects of the Mechanical Properties of Collagen Gel on the In Vitro Formation of Microvessel Networks by Endothelial Cells", *Tissue Engineering*, 13(7): 1443-1453 (2007).

Yao, J., et al., "An Essential Role for β-Actin mRNA Localization and Translation in $Ca^{2+}$-Dependent Growth Cone Guidance", *Nature Neuroscience*, 9(10): 1265-1273 (2006).

Yebra, M., et al., "Recognition of the Neural Chemoattractant Netrin-1 by Integrins a6β1 Regulates Epithelial Cell Adhesion and Migration", *Developmental Cell*, 5: 695-707 (2003).

Zheng, J.Q., et al., "Turning of Nerve Growth Cones Induced by Neurotransmitters", *Nature*, 368: 140-144 (1994).

Zhu, H., et al., "A Microdevice for Multiplexed Detection of T-Cell-Secreted Cytokines", *Lab Chip*, 8:2197-2205 (2008).

Notification of Transmittal of the International Search Report and the Written Opinion of the International Searching Authority for PCT/US2011/054029, "Device for High Throughput Investigations of Multi-Cellular Interactions", date of mailing Feb. 6, 2012.

International Preliminary Report on Patentability for PCT/US2011/054029, "Device for High Throughput Investigations of Multi-Cellular Interactions", date of mailing Apr. 2, 2013.

Park, Y.K, "Three-Dimensional Microfluidic System for Screening Antimetastatic Lung Cancer Drugs", 1 page poster presented at the 2011 BMES meeting of Oct. 12-15, 2011 in Harford, CT.

\* cited by examiner

*Primary Examiner* — Michael Hobbs

(74) *Attorney, Agent, or Firm* — Hamilton, Brook, Smith & Reynolds, P.C.

(57) ABSTRACT

Provided herein are microfluidic devices that can be used as a 3D bioassay, e.g., for drug screening, personalized medicine, tissue engineering, wound healing, and other applications. The device has a series of channels {e.g., small fluid channels) in a small polymer block wherein one or more of the channels can be filled with a biologically relevant gel, such as collagen, which is held in place by posts. As shown herein, when the device is plated with cells such as endothelial cells, new blood vessels grow in the gel, which is thick enough for the cells to grow in three dimensions. Other channels, e.g., fluid channels, allow drugs or biological material to be exposed to the 3D cell growth. Cells, such as endothelial cells, can be cultured and observed as they grow on the surface of a 3D gel scaffold, where e.g., rates of angiogenesis can be measured, as well as intervascularization and extravascularization of cancerous cells.

22 Claims, 28 Drawing Sheets

The average dimensions of a typical device in use now. This is a reference only, and does not reflect final dimensions of a production model.

The new High Throughput device

Validation Data

High concentration of anti-metastatic drugs | Low concentration of anti-metastatic drugs FIG. 10A
FIG. 10B
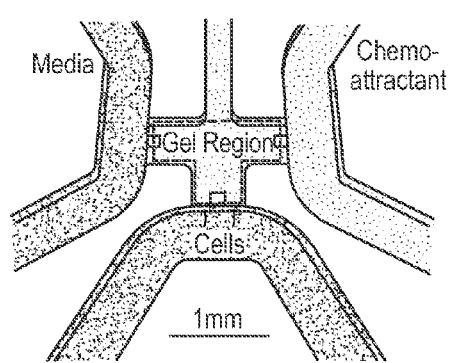
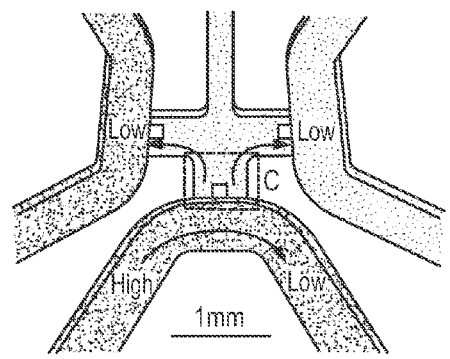
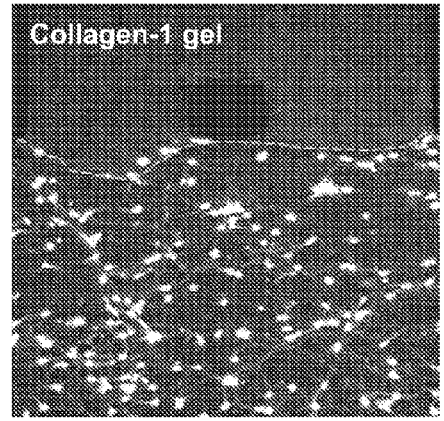
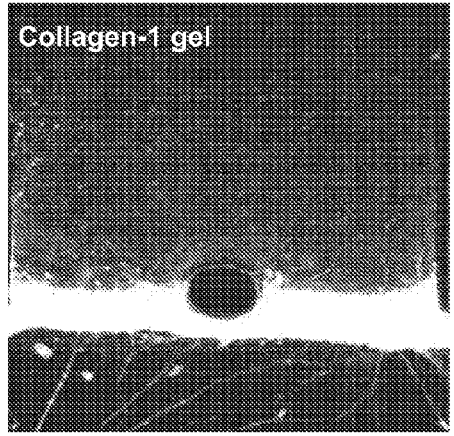

Transfected fibroblasts

Normal fibroblasts

Lab-purified Netrin

Netrin (0.1 μg/mL)

Netrin (1 μg/mL)

Netrin (10 μg/mL)

Controls

Brain pulp (0.1 μg/mL)

Brain pulp
0.1 µg/mL

Control 3.0 µm/s

Streamline Migration

Directional Migration

FIG 22D
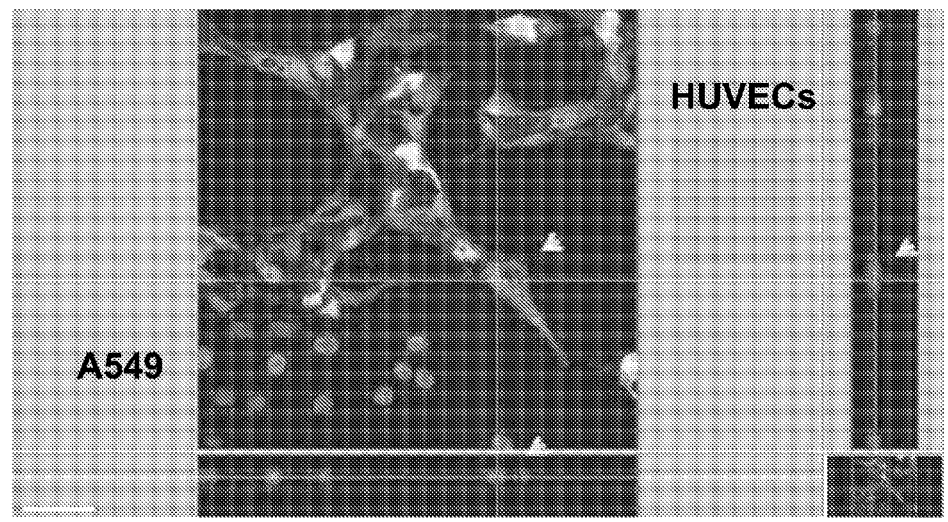
FIG 23A   FIG 23B   FIG 23C   FIG 23D
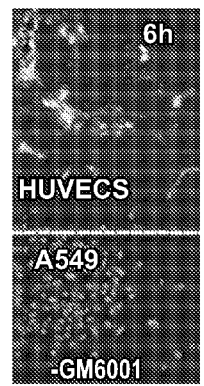 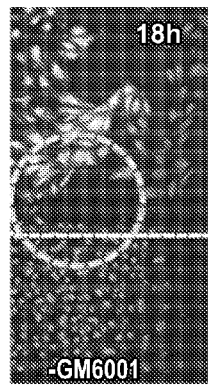 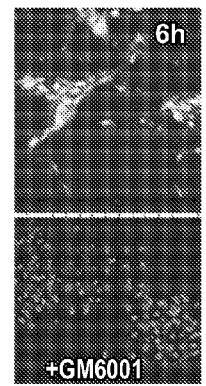 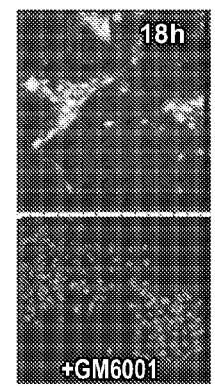

DEVICE FOR HIGH THROUGHPUT INVESTIGATIONS OF MULTI-CELLULAR INTERACTIONS

This application is the U.S. National Stage of International Application No. PCT/US2011/054029, filed on Sep. 29, 2011, published in English, which claims the benefit of U.S. Provisional Application No. 61/394,624, filed on Oct. 19, 2010 and U.S. Provisional Application No. 61/387,674 filed, on Sep. 29, 2010.

The entire teachings of the above applications are incorporated herein by reference.

GOVERNMENT SUPPORT

This invention was made with Government support under Grant Nos. NS041590, NS045523, and NS049553 awarded by the National Institutes of Health and under Grant No. EFRI-0735997 awarded by the National Science Foundation. The Government has certain rights in the invention.

BACKGROUND OF THE INVENTION

The study of cellular interactions is important to understand the development of a number of diseases. Devices for investigation of cellular interactions typically allow cells to grow on a horizontal monolayer over a sheet of collagen or other biocompatible gel. Such devices can be used, for example, with endothelial cells that eventually form blood vessels that grow downward. Adding drugs to these devices allow a qualitative assessment of the effect of the drug on the formation of blood vessels from the top of the device, where the blood vessels appear as holes in the gel. However, it is not possible to image the blood vessels from the side.

Thus, there is a need for improved devices that allow for the study of cellular interactions.

SUMMARY OF THE INVENTION

Described herein are cell assay devices that can be used to screen for agents that have an effect on living cells. For example, the device can be used to screen for anti-angiogenesis agents, anti-metastasis agents, wound healing agents and tissue engineering agents. In one aspect, the device allows blood vessels to be seen from the side, not as holes but as cones, enabling a more detailed analysis of the effects of agents (e.g., drugs) on the growth of cells (e.g., invasion of cancer cells).

In particular aspects, the device is a 3D Scaffold Microfluidic Device that can be used in a high throughput manner for investigations of multi-cellular interactions (e.g., high throughput anti-cancer drug screening). The device can be used for drug discovery and personalized medicine. For example, the device can be used as an in-vitro test for new drugs that may help stop the spread of cancer in the human body in a research setting, and to match the best anti-cancer spreading drug to a particular patient in a hospital setting. This device is an improvement over current devices in that it allows easy imaging and quantitative, not just qualitative, results.

In one aspect, the device comprises a substrate comprised of an optically transparent material and (i) one or more fluid channels; (ii) one or more fluid channel inlets; (iii) one or more fluid channel outlets; (iii) one or more gel cage regions; and (iv) a plurality of posts; wherein all or a portion of each gel cage region is flanked by all or a portion of one or more fluid channels, thereby creating one or more gel cage region-fluid channel interface regions; and each gel cage region comprises at least one row of posts which forms the gel cage region.

In another aspect, the device further comprises at least two gel cage regions wherein the gel cage regions are arranged in series to one another in the device. In another aspect, the device further comprises at least two gel cage regions wherein the gel cage regions are arranged in parallel to one another in the device.

In another aspect, the device comprises (i) a first fluid channel; (ii) a second fluid channel; (iii) one or more fluid inlets; (iv) one or more fluid outlets; (v) a gel cage region which forms a gel channel; (vi) a gel channel inlet; and (vii) a plurality of posts. In this device all or a portion of one side of the gel channel is flanked by, and parallel to, all or a portion of the first fluid channel thereby creating a first gel channel-fluid channel interface region; and all or a portion of the other side of the gel channel is flanked by, and parallel to, all or a portion of the second fluid channel thereby creating a second gel channel-fluid channel interface region. The gel channel comprises two parallel rows of posts, in which each row of posts is along the length of the gel channel and one row is along one side of the gel channel at the first gel channel-fluid channel interface, and the other row is along the other side of the gel channel at the second gel channel-fluid channel interface, thereby forming a gel cage region along the length of the gel channel; and each post forms a triangle, a trapezoid or a combination thereof.

In yet another aspect, the device comprises the device comprises (i) a first fluid channel; (ii) a second fluid channel; (iii) one or more fluid inlets; (iv) one or more fluid outlets; (v) a first gel cage region which forms a first gel channel; and (vi) a plurality of posts. In this device all or a portion of one side of the first gel channel is flanked by, and parallel to, all or a portion of the first fluid channel thereby creating a first gel channel-fluid channel interface region; and all or a portion of the other side of the first gel channel is flanked by, and parallel to, all or a portion of the second fluid channel thereby creating a second gel channel-fluid channel interface region. The first gel channel comprises two parallel rows of posts, in which each row of posts is along the length of the first gel channel and one row is along one side of the first gel channel at the first gel channel-fluid channel interface, and the other row is along the other side of the first gel channel at the second gel channel-fluid channel interface, thereby forming a first gel cage region along the length of the gel channel. The device further comprises (vii) a second gel cage region in the form of a gel channel, thereby forming a second gel channel; and (viii) a third gel cage region in the form of a gel channel, thereby forming a third gel channel. All or a portion of one side of the second gel channel is flanked by, and parallel to, all or a portion of the first fluid channel thereby creating a third gel channel-fluid channel interface region; and all or a portion of the other side of the second gel channel, is flanked by, and parallel to, all or a portion of the second fluid channel thereby creating a fourth gel channel-fluid channel interface region. The second gel channel comprises two parallel rows of posts, in which each row of posts is along the length of the second gel channel and one row is along one side of the second gel channel at the third gel channel-fluid channel interface, and the other row is along the other side of the second gel channel at the fourth gel channel-fluid channel interface, thereby forming a gel cage region along the length of the second gel channel. In addition, all or a portion of one side of the third gel channel is flanked by, and parallel to, all or a portion of the first fluid channel thereby creating a fifth gel channel-fluid channel interface region; and all or a portion of the other side of the third gel channel, is flanked by, and parallel to, all or a portion of the second fluid channel thereby creating a sixth gel channel-fluid channel interface region. The third gel channel comprises two parallel rows of posts, in which each row of posts is along the length of the third gel channel and one row is along one side of the third gel channel at the fifth gel channel-fluid channel interface, and the other row is along the other side of the third gel channel at the sixth gel channel-fluid channel interface, thereby forming a gel cage region along the length of the third gel channel. The first gel cage region, the second gel cage region and the third gel cage region are in series to one another. Each post in the device forms a triangle, a trapezoid or a combination thereof. Thus, in this embodiment, each gel cage region is in contact with the first fluid channel and the second fluid channel.

In another aspect, the device comprises a substrate comprised of an optically transparent material and (i) at least three fluid channels; (ii) at least one fluid channel inlet; (iii) at least one fluid channel outlet; (iii) at least two gel cage regions; and (iv) a plurality of posts, wherein the gel cage regions are arranged in parallel to one another. All or a portion of each gel cage region is flanked by all or a portion of one a fluid channel, thereby creating a first gel cage region-fluid channel interface region, a second gel cage region-fluid channel interface and a third gel cage region-fluid channel interface region; and each gel cage region comprises at least one row of posts which forms the gel cage region. In a particular aspect, each gel cage region forms a gel channel and each gel channel comprises two parallel rows of posts, in which each row of posts is along the length of each gel channel and one row is along one side of the gel channel, and the other row is along the opposite side of the gel channel thereby forming a gel cage region along each length of each gel channel.

In another aspect, the device comprises a substrate comprised of an optically transparent material and (i) one or more fluid channels; (ii) one or more fluid channel inlets; (iii) one or more fluid channel outlets; (iii) one or more gel cage regions; (iv) one or more gas channels wherein all or a portion of the one or more gas channels flanks at least one side of the one or more fluid channels, the one or more gel cage regions or a combination thereof; and (v) a plurality of posts. All or a portion of each gel cage region is flanked by all or a portion of one or more fluid channels, thereby creating one or more gel cage region-fluid channel interface regions; and each gel cage region comprises at least one row of posts which forms the gel cage region. The one or more gas channels allows flow of a (one or more) gases (e.g., nitrogen, hydrogen, helium, nitrogen oxide, carbon monoxide) through the device e.g., to remove oxygen.

In another aspect, the device comprises a substrate comprised of an optically transparent material and (i) one or more fluid channels; (ii) one or more fluid channel inlets; (iii) one or more fluid channel outlets; (iii) one or more gel cage regions; (iv) a membrane that is impermeable to cells and permeable to molecules secreted by cells wherein one side of the membrane is in contact with the one or more fluid channels, the one or more gel channels or a combination thereof; and (v) a plurality of posts. All or a portion of each gel cage region is flanked by all or a portion of one or more fluid channels, thereby creating one or more gel cage region-fluid channel interface regions; and each gel cage region comprises at least one row of posts which forms the gel cage region. The device can further comprise a (one or more) capture agent that specifically binds one or more molecules secreted by a (one or more) cell and the capture agent is on the opposite side of the membrane and cannot pass through the membrane.

In another aspect, the device comprises a substrate comprised of an optically transparent material and (i) one or more fluid channels; (ii) one or more fluid channel inlets; (iii) one or more fluid channel outlets; (iii) one or more gel cage regions; and (iv) a plurality of posts; wherein a portion of each fluid channel is in contact with a portion of each gel cage region and the remaining portion of each fluid channel extends away from the one or more gel cage regions. Each gel cage region comprises three posts which form a "T-shaped" gel cage region.

In another aspect, the device comprises (i) a first fluid channel; (ii) a second fluid channel; (iii) a third fluid channel; (iv) one or more fluid inlets; (v) one or more fluid outlets; (vi) a gel cage region which forms a T-shaped gel; and (vii) a plurality of posts. In this device a portion of each fluid channel is in contact with a portion of the gel cage region and the remaining portion of each fluid channel extends away from the gel cage region. Each gel cage region comprises three posts which form a "T-shaped" gel cage region. In one aspect, each post forms a square. In particular aspects, the fluid channels are in the shape of a "C", a "V", a "U" or a combination thereof, wherein a middle region of each fluid channel contacts the gel cage region and each end of the fluid channels extend away from the gel cage region (e.g., extend radially away from the gel cage region).

In another aspect, the device comprises (i) a first fluid channel; (ii) a second fluid channel; (iii) one or more fluid inlets; (iv) one or more fluid outlets; (v) an elliptical gel cage region; and (vi) a plurality of posts, wherein one side of the gel cage region is flanked by the first fluid channel thereby creating a first gel cage region-fluid channel interface, and the other side of the gel cage region is flanked by the second fluid channel thereby creating a second gel cage region-fluid channel interface. The gel cage region comprises two parallel rows of posts centrally located in the gel cage region, thereby creating a central gel chamber, a row of posts arranged in a semicircle along the first gel cage region-fluid channel interface, thereby creating a first gel chamber that flanks one side of the central gel chamber on one side; and a row of posts arranged in a semicircle at the second gel cage region-fluid channel interface, thereby creating a second gel chamber that flanks the other side of the central gel chamber.

In another aspect, the invention is directed to a method of making a device comprising etching one or more fluid channels and one or more gel cage regions into a first portion of the optically transparent material and creating one or more inlets to allow flow through the one or more fluid channels and the one or more gel cage regions, thereby creating a roof and walls of the device; and bonding the first portion of the optically transparent material to a second portion of the optically transparent material that forms a floor of the device.

In another aspect, the invention is directed to a method of identifying whether an agent is angiogenic or anti-angiogenic comprising (a) introducing an agent to be assessed into the one or more fluid channels of the device as described herein, wherein one or more fluid channels of the device comprises endothelial cells and one or more gel cage regions of the device comprises a gel that forms a gel region within the gel cage region of the device; and maintaining the device under conditions in which the endothelial cells are encouraged to adhere to the gel region at the one or more gel cage region-fluid channel interface regions. Whether creation of create cone-like protrusions that are lined with endothelial cells into the gel region are enhanced or inhibited in the presence of the agent are determined and compared to a control; wherein if creation of cone-like protrusions that are lined with endothelial cells into the gel region is enhanced in the presence of the agent compared to the control, then the agent is angiogenic, and if creation of cone-like protrusions that are lined with endothelial cells into the gel is inhibited in the presence of the agent compared to the control, then the agent is anti-angiogenic.

In another aspect, the invention is directed to a method of identifying whether an agent can be used to metastasis comprising (a) introducing an agent to be assessed into the one or more fluid channels of the device described herein, wherein one or more fluid channels of the device comprises endothelial cells, one or more fluid or gel cage regions of the device comprise cancer cells, and one or more cage regions of the device comprises a gel that forms a gel region in the gel cage region of the device; and (b) maintaining the device under conditions in which the endothelial cells are encouraged to adhere to the gel region at the one or more gel cage region-fluid channel interface regions, thereby forming an endothelial layer of cells. Whether the cancer cells disperse in the gel, migrate toward and across the endothelial layers of cells or a combination thereof in the presence of the agent is determined; wherein if the cancer cells have not dispersed in the gel, migrated toward the and across the endothelial layer of cells or a combination thereof, then this indicates that the agent can be used to inhibit metastasis.

In another aspect, the invention is directed to a method of growing blood vessels in vitro comprising (a) introducing endothelial cells into one or more fluid channels of the device, wherein one or more gel cage regions of the device further comprises a gel that forms a gel cage therein; and (b) maintaining the device under conditions in which the endothelial cells are encouraged to adhere to the gel cage at the gel cage region-fluid channel interface region and create cone-like protrusions that are lined with endothelial cells into the gel cage, thereby growing blood vessels in vitro.

In another aspect, the invention is directed to a method of identifying whether an agent is chemoattractive agent or a chemorepulsive agent of neuronal cells comprising (a) introducing an agent to be assessed and neuronal cells into the one or more fluid channels of the device described herein, the one or more gel cage regions of the device described herein, or a combination thereof; wherein the one or more cage regions of the device comprises a gel that forms a gel region within the gel cage region of the device; and (b) maintaining the device under conditions in which the neuronal cells proliferate in the gel cage region. Whether the neuronal cells proliferate toward the agent or away from the agent; wherein if the neuronal cells proliferate toward the agent, then the agent is a chemoattractive agent of neuronal cells, and if the neuronal cells proliferate away from the agent, then the agent is a chemorepulsive agent of neuronal cells.

In another aspect, the invention is directed to a method of identifying whether an agent can be used to treat cancer comprising (a) introducing an agent to be assessed into the one or more fluid channels of the device described herein, wherein one or more gel cage regions of the device comprises a gel that forms one or more gel cages, and the gel cage further comprises a biopsy of a cancerous tissue; and (b) determining whether motility of the cancerous tissue is inhibited in the presence of the agent; wherein if motility of the cancerous tissue is inhibited, then the agent can be used to treat cancer.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 10A-10B: Cell seeding in the microfluidic device. (10A) Fluorescent microscopy image of rhodamine-stained neurons attached on glass coverslip in the cell channel before external intervention. (10B) A pressure differential created by emptying media channel in the left and chemoattractant channel in the right, resulted in a strong flow through the cell channel and a small flow through the gel, progressively packing cells onto the gel. Fluorescence microscopy image of axons growing into 3D collagen gel and neurons packed on the surface of the gel, 12 h after seeding.

FIGS. 22A-22D: Cancer metastasis system within 3D CGS at 96 h after initial seeding of HUVECs. (22A-22D) Phase contrast of microscopic images and time-lapse mosaic imaging with live confocal microscopy, showing vascular network formation of HUVECs within 3D CGS (2.5 mg/ml) and also migration of A549 from 2D channels. (22C)-(22D) 3D visualization imaging with IMARIS, showing initiation of lumen formation and intravasation. Scale bars, (22A-22B) (250 μm); (22C) (100 μm); (22D) (50 μm).

FIGS. 23A-23D: Migration of A549 to CGS2 with or without GM6001. (23A-23D) and (23C-23D) Live confocal time-lapse images at 6 h and 18 h without and with GM6001, respectively. Migration of A549 is marked in yellow lines.

DETAILED DESCRIPTION OF THE INVENTION

Figure 1:
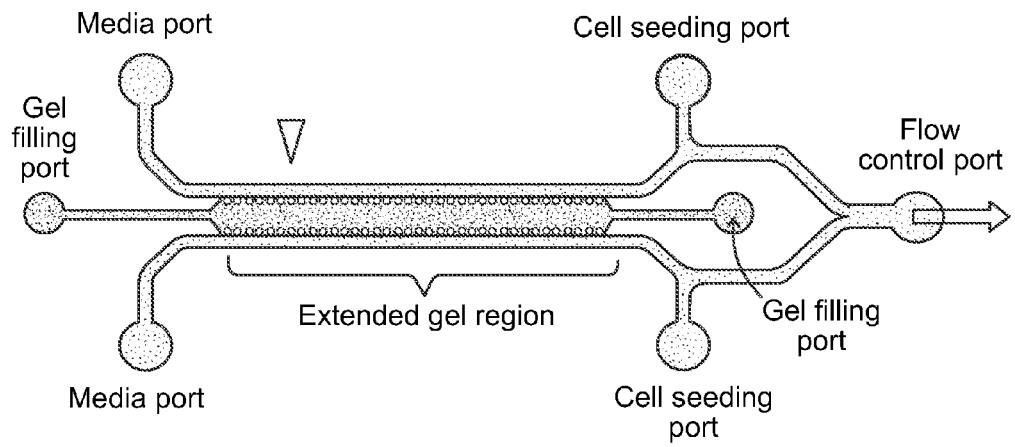
FIG. 1 shows an overhead view of one embodiment of the device. For the particular embodiment shown, measurements are approximately 25 mm by 75 mm by 1 mm. Endothelial cells are seeded in the top channel, and form small blood vessels reaching towards the bottom channel. This arrangement allows easy microscope imaging of neovascularization or cancer cell inter/extravascularization.
Figure 1:
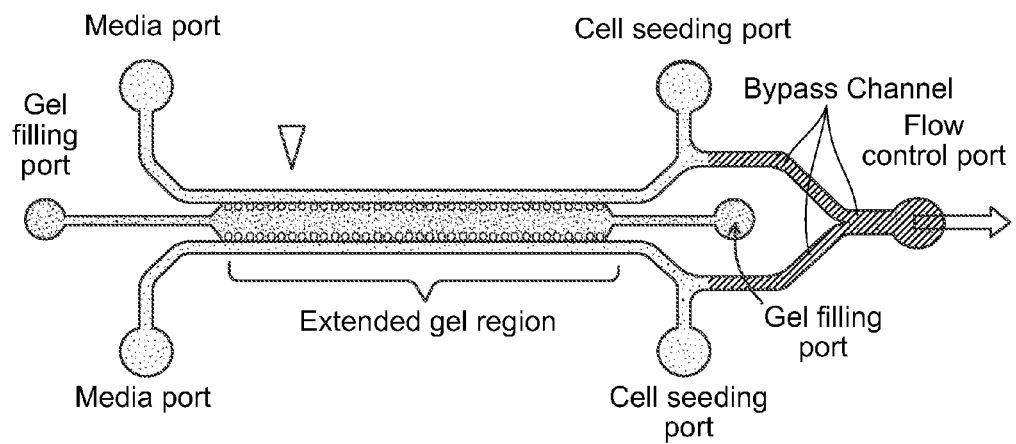
Figure 1:
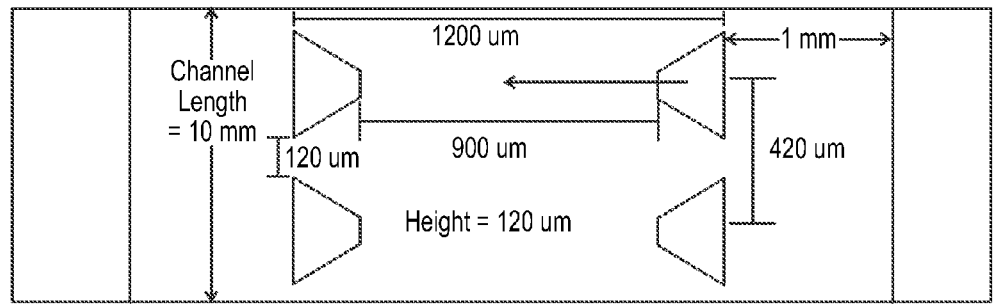

Provided herein are microfluidic devices that can be used as a 3D bioassay, e.g., for drug screening, personalized medicine, tissue engineering, wound healing, and other applications. The device has a series of channels (e.g., small fluid channels) in a small polymer block wherein one or more of the channels can be filled with a biologically relevant gel, such as collagen, which is held in place by posts. As shown herein, when the device is plated with cells such as endothelial cells, new blood vessels grow in the gel, which is thick enough for the cells to grow in three dimensions. Other channels, e.g., fluid channels, allow drugs or biological material to be exposed to the 3D cell growth. Cells, such as endothelial cells, can be cultured and observed as they grow on the surface of a 3D gel scaffold, where e.g., rates of angiogenesis can be measured, as well as intervascularization and extravascularization of cancerous cells.

Thus, in particular embodiments, the device can be used to grow a new blood vessel in vitro, and easily modify the microenvironment in which the new blood vessel forms for a variety of purposes. This can be useful in anti-cancer spreading drug discovery applications, anti-cancer growth drug discovery, tissue engineering and wound healing drug discovery, identifying chemoattractive and/or chemorepulsive agents, and matching the correct dose and combination of above drugs to a patient, among other applications. For example, in order to fit the best drug to the individual patient, a tissue biopsy of the patient's tumor can be placed in the device, with either a culture of the patient's endothelial cells or cells from an endothelial cell line. Different anti-angiogenesis and anti-metastasis drugs may also be placed in the device, and the device may help determine the extent to which the individual's cancer responds to the drugs. By linking several of these devices together in series or in parallel e.g., on the same chip, with either independent or shared fluid channels, a high throughput device can be obtained. Further modifications allow for placement of whole tissues samples, such as biopsied cancer or human tissue samples, either by injection, by hypodermic syringe or placement by micromanipulators through a port. The device may also be used for controlled development of tissues in vivo, such as vascularized muscle.

Accordingly, in one aspect, the invention is directed to a microfluidic device comprising a substrate comprised of an optically transparent material. The substrate comprises one or more fluid channels; one or more fluid channel inlets; one or more fluid channel outlets; one or more gel cage regions; and a plurality of posts. In the device all or a portion of each gel cage region is flanked by all or a portion of at least one of the one or more of the fluid channels, thereby creating one or more gel cage region-fluid channel interface regions; and the plurality of posts are in the one or more gel cage regions or in the one or more gel cage region-fluid channel interface regions. In other aspects, the sum of the contact angle of a gel on the surface of the substrate and the internal angle of a (one or more) corner of a post is about 180°.

As used herein, a "microfluidic device" refers to a device with regions, channels and/or chambers for the flow and/or containment of fluids and/or gels, typically on a miniaturized scale (e.g., microliter, nanoliter, picoliter). In order to facilitate visualization, the microfluidic device is typically comprised of a substrate that is transparent to light, referred to herein as "an optically transparent material". As will be appreciated by those of skill in the art, suitable optically transparent materials include polymers, plastic, and glass. Examples of suitable polymers are polydimethylsiloxane (PDMS), poly(methyl methacrylate) (PMMA), polystyrene (PS), SU-8, and cyclic olefin copolymer (COC). In particular embodiments, all or a portion of the device is made of a biocompatible material, e.g., the material is compatible with, or not toxic or injurious to, living material (e.g., cells, tissue).

Regions, Channels, Chambers

The optically transparent material further comprises one or more defined regions, channels and/or chambers for containment of a fluid, gel or the like. In one embodiment, the device comprises 1, 2, 3, 4, 5, 6, 7, 8, 9, 10, 11, 12, 13, 14, 15, 16, 17, 18, 19, 20, 30, 40, 50, 60, 70 80, 90, 100, etc. or any number of channels suitable for the intended use of the device. Some regions, channels and/or chambers can be used to contain a (one or more) fluid (e.g., cell culture media), cellular material, tissue and/or compounds (e.g., drugs) to be assessed, while others may be used to contain a gel (e.g., biologically relevant gel, such as collagen or Matrigel™).

In one aspect, the device comprises one or more fluid channels, wherein each fluid channel has a primary flow direction (a direction in which the fluid primarily flows). The one or more fluid channels can have the same primary flow direction or different primary flow directions. As will be appreciated by those of skill in the art, the number of fluid channels will vary depending upon the intended use. In one embodiment, the device comprises 1, 2, 3, 4, 5, 6, 7, 8, 9, 10, 11, 12, 13, 14, 15, 16, 17, 18, 19, 20, 30, 40, 50, 60, 70 80, 90, 100, etc. or any arbitrary number of fluid channels. In one aspect, there is 1 fluid channel. In another aspect, there are 2 fluid channels. In yet another aspect, there are 3 fluid channels.

In yet another aspect, the device comprises a (one or more; multiple) high fluidic resistance bypass channel (or "equalization channel") that connects to other regions or channels within the device for hydrostatic pressure equalization (e.g., see FIG. 1). The bypass channel can be included to help equalize pressure, for example, when one channel has a larger drop of fluid remaining on its inlet port after filling than another. Without the bypass channel, all fluid that will move to equalize pressure between the two channels will move through the collagen, pushing a good number of cells into the collagen. While a certain amount of this pushing due to hydrostatic pressure differences is useful in seeding cells (e.g., endothelial cells making a confluent monolayer on a gel-media interface) in a gel, in some instances, too much can start pushing several layers of endothelial cells on a gel cage region-fluid channel interface. With several layers, the endothelial cells do not act as they would in a natural environment. A bypass channel can provide an initial burst of hydrostatic pressure to push an initial layer of endothelial cells onto the gel, but then equalizes the pressure before another layer is formed. The "bypass" channel is thus useful to equalize upstream pressure to reduce/eliminate interstitial flow through the collagen matrix. The bypass channel may or may not have a flow control port. A flow control port can allow the bypass channel to act as a collector for media when one or more media ports have constant flow input (e.g., media pumped into one or more media ports, flows out of a single flow control port).

The main utility of the high resistance "bypass" channel is to reduce the interstitial flow during long term experiments with flow in the main media channels. Due to minor impedance asymmetry in the flow channels, media reservoirs at the inlet ports may drain at different rates, which alter the pressure head they are supplying to the channel over time. The "bypass" channel helps enforce symmetric pressure and flow rate boundary conditions where a flow channel-gel cage region interface occurs in the device.

As will be appreciated by those of skill in the art, the fluid channel can be formed into a variety of shapes and will depend on the intended use of the device. For example, all or a portion of a (one or more) fluid channel can be linear, curved (e.g., serpentine or S-shaped), radial (e.g., radiating away from, or converging toward, a central point or region, such as in a V-shape, U-shape, C-shape), elliptical (e.g., circular), rectangular (e.g., square), etc or combinations thereof.

In some aspects in which the device comprises more than one fluid channel, the fluid channels can run parallel to one another for all or a portion of their length. In other aspects, the fluid channels can merge toward and/or away from one another for all or a portion of their length. In other aspects, the fluid channels are physically connected along all or a portion of their length. In other aspects, one or more flow channels can be connected (e.g., either via merging, or via narrower, high resistance channels) to help establish a more symmetrical fluid flow through the device. In yet other embodiments, the fluid channels are not physically connected along their length; that is, the fluid channel are independent of one another. In additional aspects, a device comprising one or more fluid channels can be maintained in either a static or a dynamic fluid (e.g., media) flow condition.

The device further comprises one or more fluid inlets and one or more fluid outlets. As will be appreciated by those of skill in the art, each fluid channel can have its own fluid channel inlet and/or fluid channel outlet, or in the alternative, one or more fluid channels can share a fluid channel inlet and/or fluid channel outlet. In addition, the device can also comprise a single fluid channel inlet and/or a single fluid channel outlet.

The device can also comprise one or more gel cage regions, and as will also be appreciated by those of skill in the art, the number of gel cage regions will vary depending upon the intended use. In particular aspects, the device comprises 1, 2, 3, 4, 5, 6, 7, 8, 9, 10, 11, 12, 13, 14, 15, 16, 17, 18, 19, 20, 30, 40, 50, 60, 70 80, 90, 100, etc. or any arbitrary number of gel channels. In a particular aspect, the device comprises 1 gel cage region. In other aspects, the device comprises 2 cage regions. In yet other aspects, the device comprises three gel cage regions. Multiple gel cage regions within a device can be organized in a variety of ways. For example, multiple gel cage regions within a device (e.g., a single microfluidic device) can be arranged in series and/or in parallel to one another.

As with the fluid channel, the gel cage region can be formed into a variety of shapes and will depend on the intended use of the device. For example, all or a portion of a (one or more) gel cage region be linear (e.g., a gel channel), curved (e.g., serpentine or S-shaped), radial (e.g., radiating away from, or converging toward, a central point or region, such as in a V-shape, U-shape, C-shape), elliptical (e.g., circular), rectangular (e.g., square), etc. or combinations thereof. In one aspect, the gel cage region is in the form of a gel channel. In other aspects, the gel cage region is in the form of a "T". In yet other aspects, the gel cage region is in the form of a square. In yet other aspects, the gel cage region is in the form of a crescent (e.g., half-moon).

Optionally, the device can further comprise one or more gel cage region inlets and/or one or more cage region outlets. As with the fluid channels, each cage region can have its own cage region inlet and/or cage region outlet, or in the alternative, one or more gel cage regions can share a cage region inlet and/or cage region outlet. In addition, the device can also comprise a single gel channel inlet and/or a single cage region outlet.

In particular embodiments, all or a portion of each cage region is flanked by all or a portion of at least one of the one or more of the fluid channels, thereby creating one or more "gel cage region (e.g., gel channel)-fluid channel interface regions". As used herein, "flanked by" refers to a gel cage region which has all or a portion of a (one or more) fluid channel at one, or each (e.g., both), of it's sides; that is, all or a portion of a fluid channel is situated at one or each side of a cage region (e.g., all or a portion of a first fluid channel runs along side all or a portion of one side of a first gel cage region; all or a portion of a first fluid channel runs along side all or a portion of one side of a first gel cage region and all or a portion of a second fluid channel runs along side the other side of the first gel cage region). In particular embodiments, all or a portion of the one or more fluid channels is in contact (e.g., direct contact) with all or a portion of the one or more cage regions. In particular aspects, all that separates the fluid channel(s) from the gel channel(s) (or delineates the fluid channel(s) from the gel channel(s)) are one or more posts. Thus, when a gel is present in the one or more gel cage regions, the gel(s) can be contacted with any fluid present in the one or more fluid channels. In particular embodiments, each side of a gel cage region is in contact with a fluid channel. In other embodiments, all or a portion of a (one or more) gel cage region is flanked by all or a portion of another (one or more) gel cage regions, thereby creating one or more "gel cage region-gel cage region interface regions". As one of skill in the art will appreciate, depending upon the intended use, there can be a variety of interface regions such as a (one or more) gel cage region-fluid channel interface region, a gel cage region-gel cage region interface region, a fluid channel-fluid channel interface region, and multiples thereof (e.g., fluid channel-gel channel-fluid channel; fluid channel-fluid channel-gel channel-fluid channel-gel channel; fluid channel-gel channel-gel channel-fluid channel; fluid channel-gel channel-fluid channel-gel channel; etc.).

In one aspect, the entire (full) length (or a substantial portion of the length) of one or more gel cage region is flanked by the entire (full) length (or a substantial portion of the length) of one or more the fluid channels. In another embodiment, all or a portion of one or more gel cage regions is parallel to all or a portion of one or more fluid channels. In other aspects, a substantial portion of the length of one or more gel cage regions is not flanked by a substantial portion of the length of one or more the fluid channels. In yet other aspects, the one or more fluid channels and the one or more gel cage regions converge (e.g., are physically connected) on each other at an interface (e.g., a gel-fluid interface region).

Posts

Within one or more gel cage regions and/or at the boundary of one or more gel cage region-fluid channel interface regions (e.g., as they run parallel to each other) are a plurality of "posts" or "micro-posts" (e.g., around 0.1 mm wide, 0.1 mm long, and 0.25 mm high). Important features of the posts include their shape, dimension, and spacing. Shape, because it affects the orientation of the gel-liquid interface (e.g., whether it can be made to be flush with the outside of the posts and flat vs. curved), dimension since it affects the difficulty with which the devices can be fabricated, and spacing because it affects the pressure that can be supported across the gel-liquid interface during gel filling.

There were two primary objectives in designing the device, particularly for use as a high throughput device (HTD): extending the length of gel region and achieving a uniform gel-fluid interface region. A longer gel region enables the formation of a longer monolayer in the device. This, in turn, enables a larger number of cellular observations in the device (hence HTD), which can yield more statistically significant results. Non-uniformities in the gel-cage region-fluid region interface can result in irregularities in the field, which result in uncontrollable cellular observations. As described herein, these two objectives were addressed via post design.

The extended gel region can be attained by optimizing the shape and spacing of the gel posts that cage the gel matrix. There is an inherent trade-off in the gel post optimization problem. One the one hand, using tightly spaced posts results in a robust gel cage, but decreases the effective area of the device, and consequently its throughput. Using widely spaced posts, while is desirable from a throughput perspective, can result in devices that are prone to gel breakage, and potentially wasteful. As further described herein, the shape of the posts were optimized to minimize gel curvature and bulging effects so as to provide a uniform surface for experimental observations.

The footprint of the posts was decreased as much as possible since the posts decrease the usable gel length of the device. However, the posts cage a gel (e.g., a collagen solution) when present in the device. Overall, there are 3 main aspects influencing post performance: overall shape, corner angles, and roughness of the surface. Surface roughness is dependent on the fabrication process.

Overall Post Shape

The post can be formed into a variety of shapes and will depend on the intended use of the device. For example, the post can be in the form of an ellipse (e.g., circle), a rectangle (e.g., square), a triangle, a trapezoid a hexagon, a teardrop etc or combinations thereof. In a particular aspect, the post shape is in the shape of a square. In another aspect, the post is in the shape of a triangle. In yet another aspect, the post is in the shape of a trapezoid. In particular aspects, the height-to-width ratio of each post is from about 1 to about 4.

As discussed herein, depending on the dimensions of the device, the post shape can be square (see, for example, the Spider device described herein). However, in some devices, square posts (e.g., around 100 micrometers (um) by 100 micrometers, with a height of around 120 um) posed problems. It was easy to overfill the gel region, causing one or more gel-media interface regions (between the posts) to spill out into the media channel. This could often be severe enough to occlude the entire media channel, ruining the device. A more common occurrence even in proper filling was a small bulge caused by surface tension. This had the least impact on experiments, as the cells could still form a monolayer over it, but it was an annoyance. Another common problem was in underfilling. This would create a "cave" for the cells to aggregate in. An aggregation of cells would form a thick multilayer coat of cells, ruining that gel-media interface region.

Even under proper conditions, bulges still predominated. As shown herein, the curvature of the gel could be flattened out if a post would conform better to the natural shape of a droplet of gel on a surface. Forming a post around a drop of gel necessitated acute angles (less than 90 degrees), therefore, triangular shapes and variant shapes thereof were examined. This of course did not provide an exact angle—the size of the drop, and therefore the angle which is used, is dependent on how big the drop is.

Figure 3:
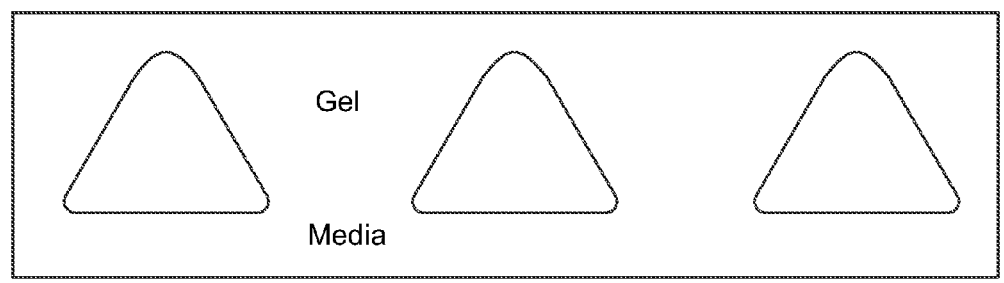
FIG. 3 illustrates trapezoidal posts and how a post conforms to a droplet of gel using acute angles; putting two droplets on both sides of a post suggests a triangular post; the angle of the post is determined by contact angle by gel on the surface of the substrate.
Figure 3:
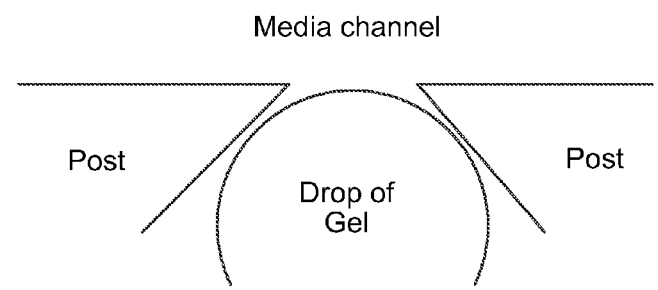
Figure 3:
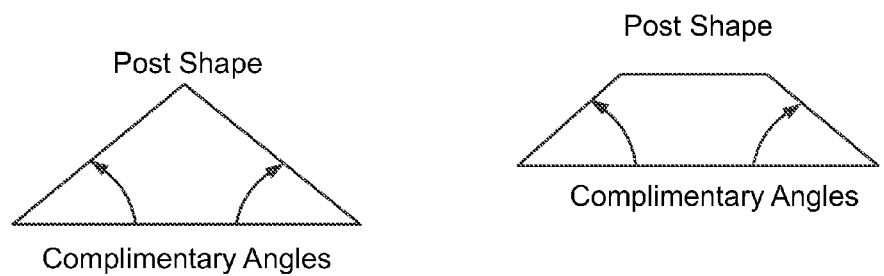
Figure 3:
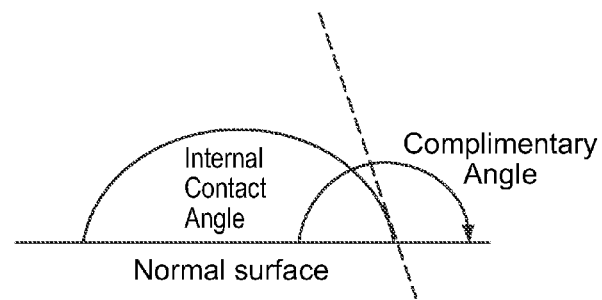

See FIG. 3 which illustrates conforming a post to a droplet of gel which necessitated using acute angles. As shown in FIG. 3 putting 2 droplets on both sides of a post indicates a triangular post shape. The exact angle of the post is determined by the contact angle of the gel on the surface of the substrate.

As used herein, a "contact angle" is the angle at which a liquid/vapor interface meets a solid surface (FIG. 3). The contact angle is specific for any given system and is determined by the interactions across the three interfaces. Most often the concept is illustrated with a small liquid droplet resting on a flat horizontal solid surface. The shape of the droplet is determined by the Young's relation. The contact angle plays the role of a boundary condition. Contact angle is measured using a contact angle goniometer. The contact angle is not limited to a liquid/vapour interface; it is equally applicable to the interface of two liquids or two vapours.

For purposes herein, consider a liquid drop on a solid surface. If the liquid is very strongly attracted to the solid surface (for example water on a strongly hydrophilic solid) the droplet will completely spread out on the solid surface and the contact angle will be close to 0°. Less strongly hydrophilic solids will have a contact angle up to 90°. On many highly hydrophilic surfaces, water droplets will exhibit contact angles of 0° to 30°. If the solid surface is hydrophobic, the contact angle will be larger than 90°. On highly hydrophobic surfaces the surfaces have water contact angles as high as ~120° on low energy materials e.g. fluorinated surfaces. However some materials with highly rough surface may have water contact angle greater than 150°.

Corner Angles of the Post

As described herein, optimum post shapes for particular microfluidic device were determined. It was discovered that the acute angle for the corners of posts and the contact angle formed between the gel and the surface of the substrate should form a pair of supplementary angles wherein the sum of the degree measurement of these two angles equals 180°. See FIG. 3. That is, the correct acute angle for the corners of posts is the angle that is the supplement of the contact angle formed between the gel and the surface of the substrate. In particular embodiments, triangular and/or trapezoidal posts, with such specific acute angles are used. In other embodiments, square posts are used (e.g., the Spider device). However, as will be appreciated by those of skill in the art, although particular devices have been exemplified with particular posts herein, different posts shapes can be used if desired.

As discussed above, in general a contact angle is the angle at which a droplet of a liquid meets a surface that it is resting on. Hydrophobic surfaces will cause the water droplet to "ball up", while hydrophilic surfaces will cause the droplet to spread out. A gel is primarily water, so hydrophobicity of the substrate impacts the angle at which a droplet of the gel meets the surface of the substrate. The angles of the posts that lie on the gel-liquid interface of the substrate and the internal contact angle of a drop of gel as it lies on the substrate are supplementary angles (i.e., the degree measurement of the sum of these two angles is 180°). This means that the internal angles of the post which meet at the gel-fluid interface used depends on the material used, and the surface treatment of the substrate, such as exposure to a plasma channel or coating with a chemical or protein such as Poly-D-Lysine, of the gel composition. The internal angles of any corner of a post are where the corner of the post meets a gel-fluid interface. In this case, the angles of e.g., a trapezoid, that face "in" towards the center of the gel channel "see" only gel, while the other two internal angles "see" gel and media. Using the correct angle for the post makes gel filling much easier, and enables a flat collagen-media interface that is very difficult to achieve with square posts, or other shapes. In one embodiment, the internal angle is less than or equal to about 90°, about 80°, about 70°, about 60°, about 50°, about 40°, about 30°, about 20°. In a particular embodiment, the internal angle is about 60°.

In one embodiment, triangular shapes, forming the supplementary angles mentioned above for 2 out of the 3 angles of a triangle are used for the posts. In another embodiment, trapezoidal shapes, which allow better gel flow when loading the device with gel are used for the posts. In particular, the one or more posts are in the shape of an isosceles triangle, an isosceles trapezoid or a combination thereof.

Thus, the contact angle depends on substrate material (what the device is made of) and surface treatment. For example, using PDMS, with a surface treatment of exposure to pink plasma for 1.5 minutes, followed by coating with Poly-D-Lysine (a kind of "cell glue), and a rinsing and baking procedure for the device, will yield a contact angle of about 121°, which indicates that a supplementary angle of about 59° for the internal angle of a post corner that will converge at a gel-fluid interface in the device. Poly-D-Lysine is a polypeptide that absorbs easily to most hydrophilic surfaces, and binds non-specifically to cells. It promotes adhesion of collagen to the substrate. This device is a hydrophobic surface; water will try to become very ball-like on this treated surface. As will be apparent to one of skill in the art, the supplementary angle can be rounded to about 60° for production purposes.

Theoretically, if a substrate were given a surface treatment that was designed to have a contact angle of 90°, a square post would suffice. This would be at the limit of this gel caging concept. However, a triangular or trapezoidal shape was chosen as it allows gel to better flow through a channel. Narrow gel channels are harder to flow through, but cutting off the inward facing tip of the triangle, the effective width of the channel was increased. The correct post coupled with proper surface treatment can lead to a flat gel-interface boundary.

In particular embodiments, triangular posts with each side being around 0.1 mm are common, as are trapezoidal posts. However, as described herein, posts for other devices, such as the spider device or the biopsy (half moon) device embodiments can be any shape, e.g., circular, square, bell and other arbitrary shapes. The microposts may be 0.2 mm apart, though this can be longer or shorter depending on gel thickness, device construction material properties, device surface modification, and many other factors. The posts or microposts form a kind of "gel cage" along the length of a gel cage region. The mposts are designed to allow the filling of the device with a biologically relevant gel, such as collagen or any other kind of gel. Surface tension of the gel between the micro-posts keeps the gel contained within the posts. Trapezoidal and triangular shapes have been found to be the most effective in particular devices, generally with their "sharp" ends pointed away from the cells and towards the gel. The sharp ends are the internal angles that are dependent on surface contact angle, and that these ends point out towards the media channel. In some aspects, the posts will generally line the boundary between two connected, parallel channels, of which one channel is reserved for fluid e.g., culture media or cellular material, while the other channel will be filled with any biologically relevant gel. The shape made by the pattern of posts, in other words the shape of the gel cage, may vary. Some aspects of the device will contain two parallel rows of triangular shaped posts, to separate the lengths of channels that run parallel to each other, forming a rectangle with the channel inlets and outlets constituting the remaining two sides. Other shapes, such as circles and semi-circles, may be formed by the posts, and any other arbitrary shape of microposts, themselves of arbitrary shapes, may be used.

In particular embodiment, the posts are oriented such that the distance between the posts is closer at the edge of the gel cage region (at the gel-fluid (gel cage region-fluid channel) interface) than it is towards the center of the gel cage region in order to maximize the sustainable pressure drop between the gel-fluid boundary during filling. Examples include a device with triangular or trapezoidal posts, wherein the top or tip of the posts point in towards the center of the gel cage region and the base of the post is at the fluid-gel interface.

The pressure drop across an air-gel interface is given by: $\Delta P = \gamma(1/R_x + 1/R_z)$, where $\Delta P$ is the pressure drop, $\gamma$ is the surface tension, and $R_x$ and $R_z$ are the radii of curvature of the gel interface. A gel interface that is robust to pressure perturbations during the filling process is one that can carry a large $\Delta P$. Therefore it is desirable to choose $\gamma$, $R_x$ and $R_z$ that maximize $\Delta P$. Since $\gamma$ is a gel fluid property, it cannot be modified significantly. Since $R_z$ is dependent on the height of the channel, $R_x$ is the only remaining parameter that can be related to post spacing. Thus, it is desirable to minimize $R_x$, which is equal to twice the post spacing at the nearest points between two adjacent posts.

A converging geometry leads to a smaller radius, giving a higher pressure drop, for better containment during filling. As used herein, "converging" refers to when, as the gel flows from the center of the gel channel towards the outside of the gel channel, the spacing between posts that the gel contacts decrease. After filling, the contact angle will produce a flat(ter) gel-fluid interface. A diverging geometry produces a larger radius, which cannot sustain high pressure for filling.

The desired property here is that, for hydrophobic surfaces, the geometry of the posts should be converging as we move from the center of the gel region to the fluid region. This is important because it makes gel filling a stable process. Triangular and trapezoidal posts are examples of posts that achieve this effect in particular devices. During filling bulges occur at the upstream end of the device, decreasing along the length of the device. After filling (static fluid) pressure equilibrates and extra bulge volume is spread throughout the device.

Surface Roughness

Surface tension keeps the gel within the boundaries of the gel channel. A rough surface of a post can cause small stress points on the surface of the gel as it tries to conform to the rough post at the meeting point of the post, gel, and media (the outer corner of the post). This has the effect of lowering the overall pressure that can be applied to the gel during the injection phase without causing the surface tension to "break" from the post and spill into the media channel. In other words, rough surfaces make it much harder to properly fill a gel channel. In a particular embodiment, the posts are made of the same material as the substrate.

Arrangement of Posts

The plurality of posts in the device can be arranged in a variety of orientations within a device and will depend upon the intended use for the device. For example, all or a portion of the plurality of posts in a device can be arranged in a single row, two or more parallel rows, a "T" shape, a circle, a semicircle, a rectangle, etc, or combinations thereof.

In particular aspects, each gel cage region-fluid channel interface region or each gel cage region comprises two parallel rows of posts in which each row of posts is along the length of each gel cage region-fluid channel interface region, and one row is along the inner boundary of a gel cage region and the other row is along the outer boundary of the gel channel, thereby forming a gel channel. The gel region of the device is formed by a cage comprising 2 rows of posts, with one row forming one boundary between a fluid-gel or gel-gel interface, and another forming a distinct boundary between another distinct fluid-gel or gel-gel interface. The size and shape of the posts can vary to maximize their effectiveness. Furthermore, the dimensions of the posts, their spacing, and their shapes are chosen to enable gel filling in the gel region The devices provided herein can have, for example, 66 sites (66 areas between posts), with a post spacing of 0.125 mm, yielding a total gel region (e.g., total linear region) of 8.25 mm. Previous devices can only display 0.9 mm of gel-fluid interface to any one channel, however, the devices described herein can display e.g., 4.125 mm for any one gel channel which is about a 458% increase in total gel-fluid surface area compared to previous devices. In some aspects, the total gel region is about 1.5 mm, 2 mm, 2.5 mm, 3 mm, 3.5 mm, 4 mm, 4.5 mm, 5 mm, 5.5 mm, 6.0 mm, 6.5 mm, 7.0 mm, 7.5 mm, 8.0 mm, 8.5 mm, 9.0 mm, 9.5, 10 mm, 15 mm, 20 mm, 25 mm etc. In other aspects, the devices provided herein can provide a total gel-fluid surface area that is about a 50%, 75%, 100%, 125%, 150%, 175%, 200%, 225%, 250%, 275%, 300%, 325%, 350%, 375%, 400%, 425%, 450%, 475%, 500%, 525%, 550%, 575%, 600%, 625%, 650%, 675%, 700%, 725%, 750%, 775%, 800%, 825%, 850%, 875%, 900%, 925%, 950%, 975%, 1000% etc. increase compared to previous devices. In yet other aspects, the total gel region (e.g., total linear gel region), defined as post-to-post distance×the tnumber of sites, can be from about 100 micrometer (μm) to 10 meters (m), from about 1 micrometer to about 1 millimeter (mm), from about 1 mm to 1 meter, etc.

Gel Cage Region Properties

After the proper post shape was obtained, the proper gel cage region properties were determined. The distance between successive posts in a gel cage, the height and width of a gel cage (e.g., channel), and the length of a gel cage region determine the probability of successfully filling the gel cage region, and therefore manufacturing the device.

Even with a proper post shape, gel filling is dependent on other factors. Generally gel filling is guided by the premise that the pressure applied to inject the gel must always be less than the surface tension at any point along the entire gel-media interface. If, for example, one post is defective and causes a local high stress point, then as soon as the pressure of injection is greater than the maximum surface tension possible at that point, the gel will spill out of the gel channel at that point, ruining the device.

Overall, a low injection pressure will flow gel a few millimeters up a gel channel, but as the filled portion of the channel grows, the resistance to flow is greater, and a greater pressure is needed at the injection site to continue filling the device. A long device will need a great pressure to fully inject, meaning that there is a greater chance that at any point, the injection pressure is higher than the local surface tension, causing a spill. A few factors can be modified to lessen the probability of a spill. See FIG. 1 for an example of dimensions of a device. This is a reference only, and does not reflect final dimensions of a production model.

Distance Between Posts

Closer post spacing creates a stronger surface tension between the posts. This means that, all other things being equal, a channel with very closely spaced posts can be filled a greater distance than one with widely spaced posts. However, closely spaced posts limit the amount of gel-media interaction, and make it hard for cells to grow into the 3D gel matrix. There is a tradeoff between device quality to the user (who wants wider gel regions) and manufacturability (as wide gel regions make it harder to successfully fill the device). In one embodiment, the post-to-post spacing is from about 1 micrometer to about 500 micrometers, 5 micrometers to about 450 micrometers, about 10 micrometers to about 400 micrometers, or about 50 micrometers to about 300 micrometers wide. In other embodiments, the spacing between posts is about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 micrometers. In a particular embodiment, each post is about 300 micrometers wide, which gives a gel-media interface region of around 120 micrometers. In a particular embodiment, the post-to-post spacing is about 420 micrometers.

Height of Gel Cage Region

The height of a channel is linked to the post spacing. In one aspect, the channel height is approximately equal to the amount of space between posts. Even with a relatively straight gel-media interface when viewed from the top, there will still be some curvature, even if it is just when viewed from the side. The gel still contacts the top "ceiling" and bottom "floor" of the device, and those are not angled correctly for a flat interface in the top-bottom dimension. In the event of a bulge when viewed from the top, it is desired that this be the same bulge (same curvature) as when viewed from the side. This is more important on some devices when bulges were more common, but still retained in the high throughput device.

Figure 4:
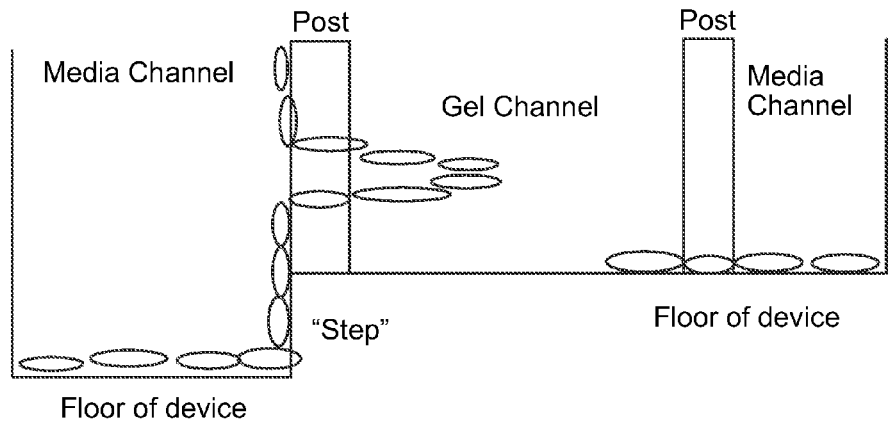
FIG. 4 illustrates a device with gel channels and fluid channels having different heights.

A higher device is also more conducive to better experimental results. Cells tend to like to grow along surfaces, such as the top and bottom ceiling and floor of the device. A higher gel region encourages cells to explore the 3D gel, rather than stick to the top and bottom surfaces. In a particular embodiment, the device can also comprise a step up from a media channel to a gel cage region (e.g., a stepped device). In one aspect, the step between the fluid channel and the gel cage region is about a 2-fold step, a 3-fold step, a 4-fold step, etc. For example, the device could comprise a high media channel of about 200 um, and a high gel channel of about 400 um. In other embodiments, the one or more fluid channels has a height of about 10 µm, 20 µm, 50 µm, 100 µm, 125 µm, 150 µm, 175 µm, 200 µm, 225 µm, 250 µm, 300 µm, 350 µm, 400 µm, and 500 µm; and the one or more gel channels has a height of about 20 µm, 40 µm, 80 µm, 100 µm, 150 µm, 200 µm, 250 µm, 300 µm, 400 µm, 500 µm, 600 µm, 700 µm, 800 µm, 900 µm, and 1000 µm. A shorter media channel allows the use of less media, which saves costs when rare and expensive media reagents are used. The higher gel regions allow freer movement and less interaction and interference from the mechanically stiff "ceiling" and "floor" of the device (e.g., see FIG. 4).

Width of a Gel Channel

Typically, wider gel channels are easier to fill, and narrower channels have higher resistance, and therefore require more pressure to fill. Fluidic resistance depends on both the width and the length of a channel. As long as the pressure necessary to fill a device is less than the surface tension of an inter-post gel-media interface, the gel will continue to fill and not spill. As the filled gel region becomes longer, the required pressure to fill increases, and will eventually match the surface tension of a inter-post region, causing a spill. This means that in order to fill a long channel, either the gel channel must be wider (to reduce resistance), or the post spacing shorter (to increase surface tension). There is interplay between post spacing, channel width, and the maximum fillable channel length.

Gel Cage Region

Other versions of the microdevices use a random arrangement of posts, as at that time it was not known what arrangement was best. Posts were located both inside the cage and along the perimeter. For example, a 3-channel device had 4 distinct gel cages, each with 2 posts. In contrast, the device described herein can comprise two parallel rows of posts, with the gel filling port outlets forming the other two walls of a rectangular gel cage.

Gel

As shown herein, the device can further comprise a gel in the gel channel, thereby forming a gel region in the device. Any relevant gel that would act as an extra-cellular matrix can be used, such as collagen, Matrigel™, fibronectin and the like.

In some aspects, the length of the gel region (a single gel region) can be about 100 micrometers to about 100,000 micrometers. In other aspects, the gel region is about 500 micrometers; 1000 micrometers; 5000 micrometers; 10,000 micrometers; 15,000 micrometers; 30,000 micrometers; 50,000 micrometers; or 100,000 micrometers. As will be appreciated by one of skill in the art, the device can have multiple gel cage regions (e.g., in series to one another, in parallel to one another or a combination thereof), thereby increasing the total length of the gel regions in a single device (e.g., increasing the observational area). In addition, the multiple gel cage regions can have the same or similar gels in each gel cage region, or, alternatively, the multiple gel cage regions can have different gels (e.g., gels that differ in composition; gels that differ in properties (e.g., stiffness) etc. and combinations thereof).

Thus, in other aspects, the device is of a high throughput nature. The high-throughput device addresses the need for increased experimental observations given particular cellular conditions. Increasing the number of observations made in parallel or in series has the important benefit of obtaining statistically meaningful cell culture metrics without having to build too many devices, thereby expediting the experimental investigations and the screening process. Additionally, increasing the number of observations on a single device minimizes that additional variance induced by device-to-device variations.

The number of experimental observations under a given set of conditions is directly proportional to the number of cell growth regions (e.g., channels) in the device, or alternatively, to the surface area of the monolayer formed by the cells under culture. The high-throughput devices described herein achieve this increase in area by allowing for a gel region of extended length to be placed in between channels.

To make this device truly high throughput, several of these gel regions can be placed in series or parallel to each other, and fluid channels, either separate, connected, or a mix of connectivities, can be run to and from the gel regions.

Other embodiments include circular gel cage regions for the placement of biopsied tissue. This tissue can be placed in contact with the gel region, and allow emitted chemical signals to penetrate the gel, and to expose the tissue to experimental or clinically relevant drugs. The gel and/or fluid channels can further comprise cellular material, e.g., cells, cell culture media, tissue, growth factors, drugs (therapeutic drug, diagnostic drug), or a combination thereof. In particular embodiments, the gel cage region (e.g., gel channel) and/or fluid channel can further comprise cells e.g., a suspension of cells. Examples of such cells include cancer cells, neurons, endothelial cells, smooth muscle cells, stem cells, epithelial cells or a combination thereof. In particular embodiments, the cell are stained with a marker to enhance the imaging process. Suitable markers include fluorescent markers, such as rhodamine-phalloidin (Invitrogen) to visualize actin filaments of any cell type, VE-Cadherin antibodies to visualize endothelial cell-cell junctions, DAPI to visualize nuclei, and cell lines that express constitutively GFP-cytosolic proteins to allow for real-time imaging.

Another application would be to use encapsulated cells that can be inserted into the fluid (e.g., media) channels. The benefit is that the factors secreted by the cells can act on another cell population while the cells are prevented from migrating together to become intermixed.

Adding drug/agent reservoirs and/or the necessary channels for mixing them on the device (e.g., on-chip) are also encompassed.

Specific Embodiments of the Device

Provided herein are microfluidic devices comprised of an optically transparent material and further comprising one or more fluid channels, one or more gel cage regions and a plurality of posts that can be used, for example, to study cell migration, cancer metastasis, angiogenesis, whole tissue biopsies and to discover agents that can be used in would healing, cancer (e.g., metastasis) and tissue (e.g., neural) engineering. In these alternative devices, the gel cage regions and fluid channels are arranged to facilitate the particular uses for which they are designed and are less dependent on the post shape.

High Throughput Device

In one aspect, the device comprises a substrate comprised of an optically transparent material and (i) one or more fluid channels; (ii) one or more fluid channel inlets; (iii) one or more fluid channel outlets; (iii) one or more gel cage regions; and (iv) a plurality of posts; wherein all or a portion of each gel cage region is flanked by all or a portion of one or more fluid channels, thereby creating one or more gel cage region-fluid channel interface regions; and each gel cage region comprises at least one row of posts which forms the gel cage region (e.g., see FIG. 1). In another aspect, the device further comprises at least two gel cage regions wherein the gel cage regions are arranged in series to one another in the device. In another aspect, the device further comprises at least two gel cage regions wherein the gel cage regions are arranged in parallel to one another in the device.

In a particular aspect, each gel cage region forms a gel channel and each gel channel comprises two parallel rows of posts, in which each row of posts is along the length of each gel channel and one row is along one side of the gel channel, and the other row is along the opposite side of the gel channel thereby forming a gel cage region along each length of each gel channel.

In another aspect, the device comprises (i) a first fluid channel; (ii) a second fluid channel; (iii) one or more fluid inlets; (iv) one or more fluid outlets; (v) a gel cage region which forms a gel channel; (vi) a gel channel inlet; and (vii) a plurality of posts. In this device all or a portion of one side of the gel channel is flanked by, and parallel to, all or a portion of the first fluid channel thereby creating a first gel channel-fluid channel interface region; and all or a portion of the other side of the gel channel is flanked by, and parallel to, all or a portion of the second fluid channel thereby creating a second gel channel-fluid channel interface region. The gel channel comprises two parallel rows of posts, in which each row of posts is along the length of the gel channel and one row is along one side of the gel channel at the first gel channel-fluid channel interface, and the other row is along the other side of the gel channel at the second gel channel-fluid channel interface, thereby forming a gel cage region along the length of the gel channel; and each post forms a triangle, a trapezoid or a combination thereof.

Serpentine Device

Figure 19A:
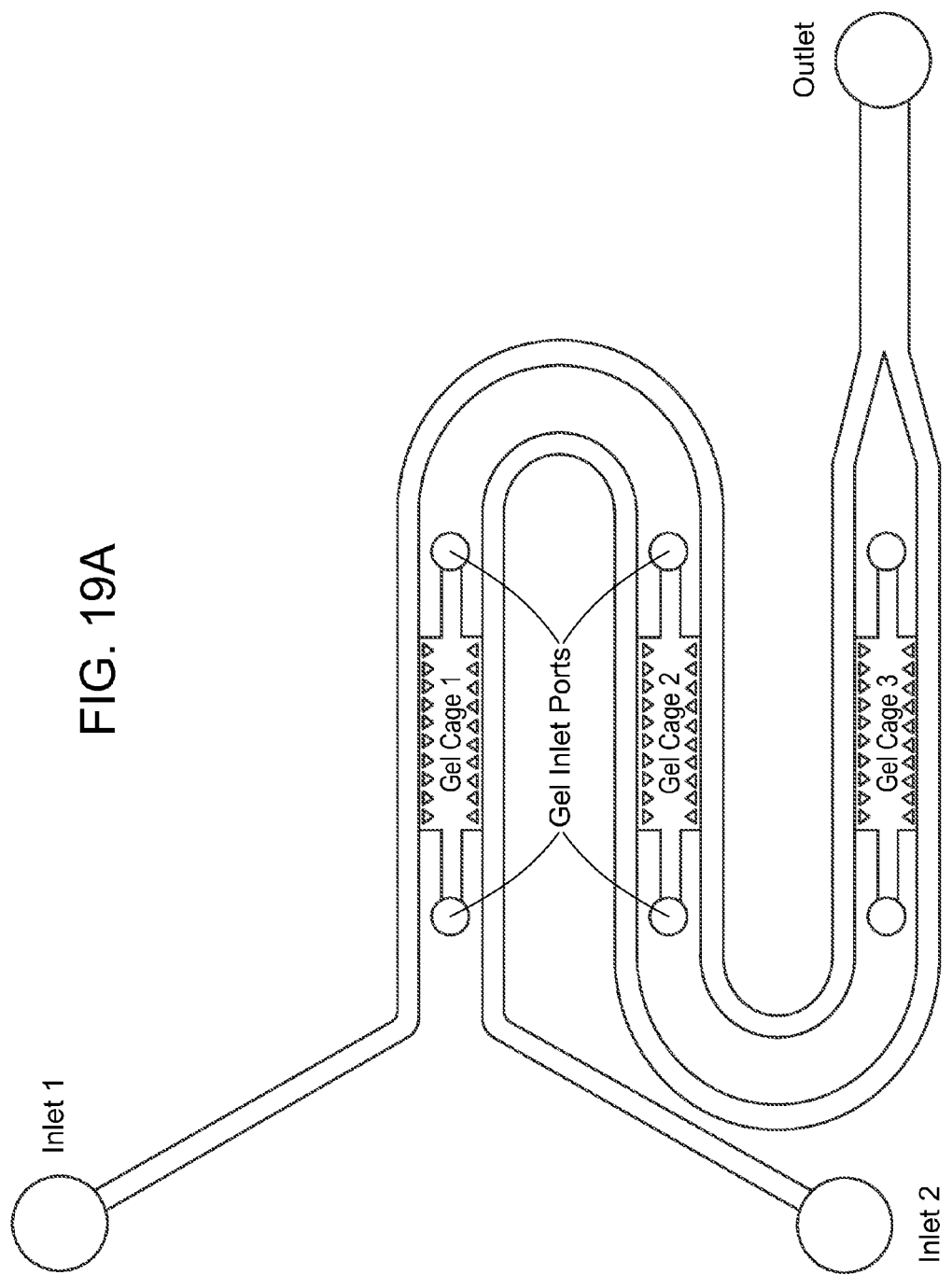
FIGS. 19A-19D: Illustration of the S-shaped or serpentine device, comprising 3 gel regions placed one after the other and sharing the same media channel. Thus, the same media can interact with at least 3 different cell types in the gel. In this embodiment, the two inlet channels merge to a single outlet, which can be useful in constant flow experiments.
Figure 19C:
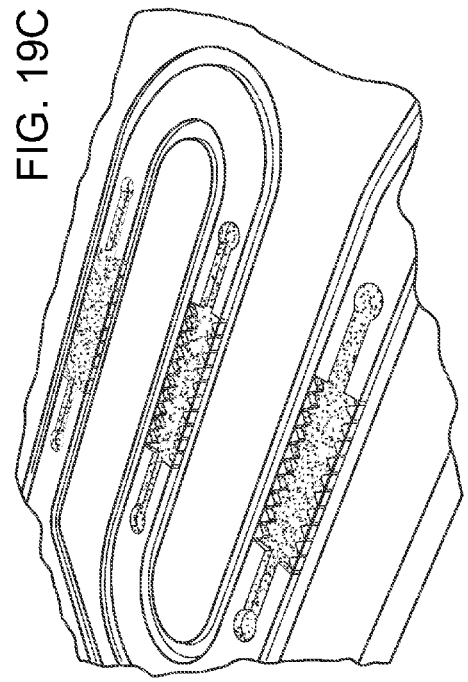

In yet another aspect, the device comprises the device comprises (i) a first fluid channel; (ii) a second fluid channel; (iii) one or more fluid inlets; (iv) one or more fluid outlets; (v) a first gel cage region which forms a first gel channel; and (vi) a plurality of posts (e.g., see FIGS. 19A-19C). In this device all or a portion of one side of the first gel channel is flanked by, and parallel to, all or a portion of the first fluid channel thereby creating a first gel channel-fluid channel interface region; and all or a portion of the other side of the first gel channel is flanked by, and parallel to, all or a portion of the second fluid channel thereby creating a second gel channel-fluid channel interface region. The first gel channel comprises two parallel rows of posts, in which each row of posts is along the length of the first gel channel and one row is along one side of the first gel channel at the first gel channel-fluid channel interface, and the other row is along the other side of the first gel channel at the second gel channel-fluid channel interface, thereby forming a first gel cage region along the length of the gel channel. The device further comprises (vii) a second gel cage region in the form of a gel channel, thereby forming a second gel channel; and (viii) a third gel cage region in the form of a gel channel, thereby forming a third gel channel. All or a portion of one side of the second gel channel is flanked by, and parallel to, all or a portion of the first fluid channel thereby creating a third gel channel-fluid channel interface region; and all or a portion of the other side of the second gel channel, is flanked by, and parallel to, all or a portion of the second fluid channel thereby creating a fourth gel channel-fluid channel interface region. The second gel channel comprises two parallel rows of posts, in which each row of posts is along the length of the second gel channel and one row is along one side of the second gel channel at the third gel channel-fluid channel interface, and the other row is along the other side of the second gel channel at the fourth gel channel-fluid channel interface, thereby forming a gel cage region along the length of the second gel channel. In addition, all or a portion of one side of the third gel channel is flanked by, and parallel to, all or a portion of the first fluid channel thereby creating a fifth gel channel-fluid channel interface region; and all or a portion of the other side of the third gel channel, is flanked by, and parallel to, all or a portion of the second fluid channel thereby creating a sixth gel channel-fluid channel interface region. The third gel channel comprises two parallel rows of posts, in which each row of posts is along the length of the third gel channel and one row is along one side of the third gel channel at the fifth gel channel-fluid channel interface, and the other row is along the other side of the third gel channel at the sixth gel channel-fluid channel interface, thereby forming a gel cage region along the length of the third gel channel. Each post in the device forms a triangle, a trapezoid or a combination thereof. Thus, in this embodiment, each gel cage region is in contact with the first fluid channel and the second fluid channel.

In one aspect, the number of posts for each gel cage region is composed of 10 in the top side and 10 in the bottom side. Thus, in this aspect, the device has total of 60 mechanical posts.

Multiplexed Device

Figure 26A:
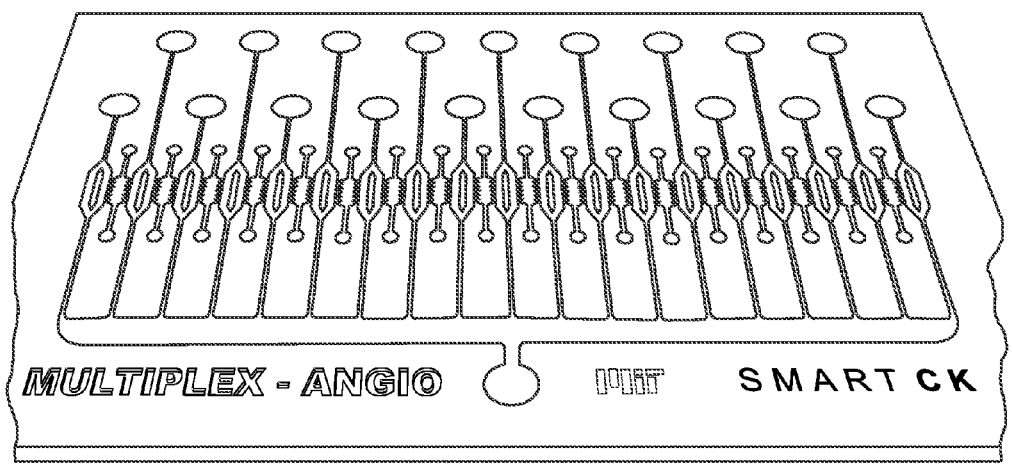
FIGS. 26A-26B: A multiplexed high throughput device in which the gel regions are parallel. This device increases the available gel for a single culture type, or allows different cell types embedded in the gel to be exposed to the same media conditions if the media is injected in a single media port. When injecting media through the many media ports, each gel can be subjected to two different media conditions. In this mode, Gel Region 1 can see Media Condition 1, while Gel Region 2 can see Media Condition 2 and 3, etc. This allows a rapid investigation of the effects of different media conditions (e.g., drugs, pressure differences, etc.) on a cell type while it is suspended in a gel. Partitions in the media channels endure there is no mixing of cellular secretions from the cells in the gel channels.
Figure 26B:
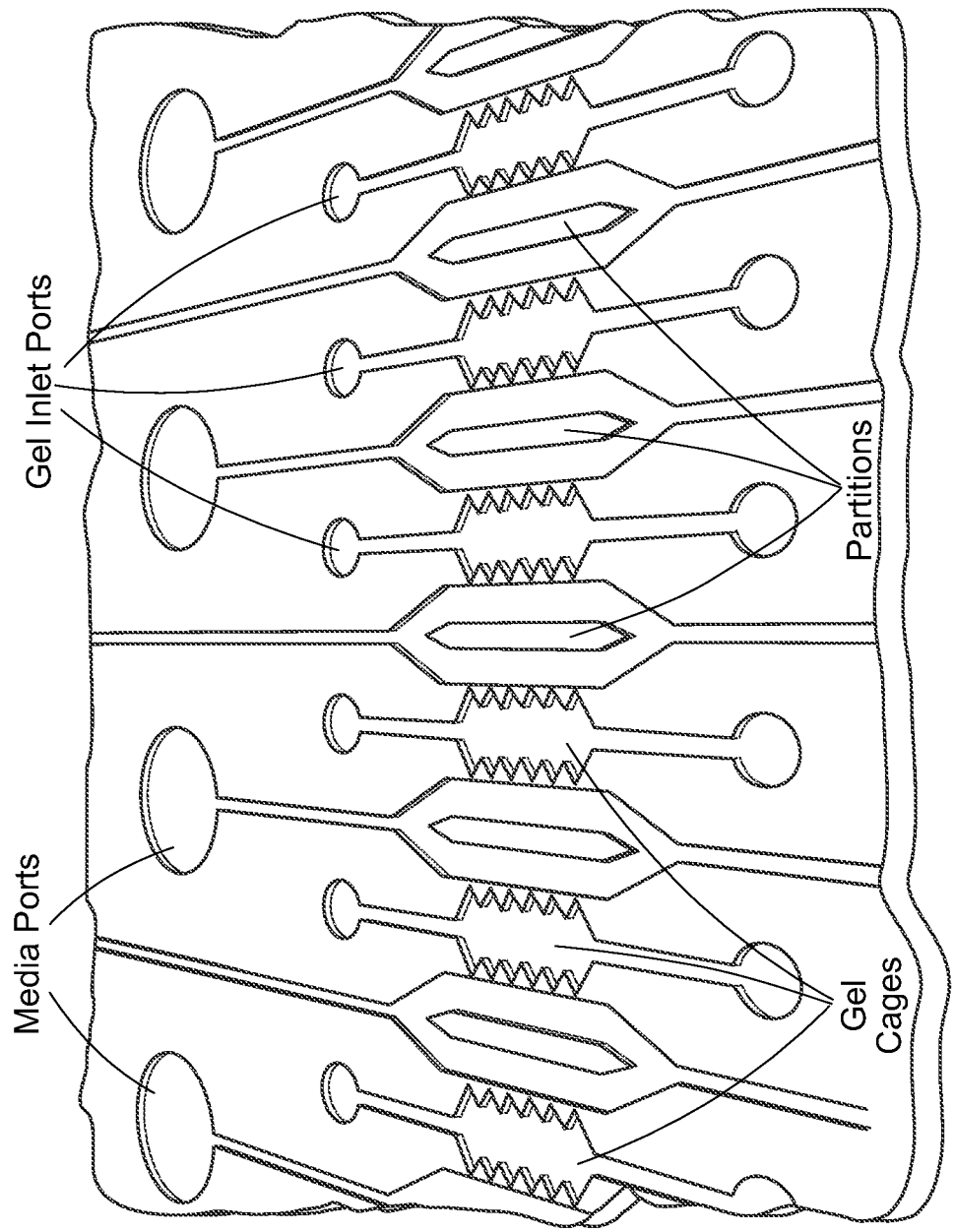

In another aspect, the device comprises a substrate comprised of an optically transparent material and (i) at least three fluid channels; (ii) at least one fluid channel inlet; (iii) at least one fluid channel outlet; (iii) at least two gel cage regions; and (iv) a plurality of posts (e.g., see FIGS. 26A-26B). All or a portion of each gel cage region is flanked by all or a portion of one a fluid channel, thereby creating a first gel cage region-fluid channel interface region, a second gel cage region-fluid channel interface and a third gel cage region-fluid channel interface region; and each gel cage region comprises at least one row of posts which forms the gel cage region. In a particular aspect, each gel cage region forms a gel channel and each gel channel comprises two parallel rows of posts, in which each row of posts is along the length of each gel channel and one row is along one side of the gel channel, and the other row is along the opposite side of the gel channel thereby forming a gel cage region along each length of each gel channel.

In a particular embodiment, the device comprises a substrate comprised of an optically transparent material and (i) a first fluid channels; (ii) a second fluid channel; (iii) a third fluid channel (iv) at least one fluid channel inlet; (v) at least one fluid channel outlet; (vi) a first gel cage region which forms a first gel channel; (vii) a second gel cage region which forms a second gel channel; and (viii) a plurality of posts. All or a portion of one side of the first gel channel is flanked by, and parallel to, all or a portion of the first fluid channel, thereby creating a first gel channel-fluid channel interface region; and all or a portion of the other side of the first gel channel is flanked by, and parallel to, all or a portion of the second fluid channel, thereby creating a second gel channel-fluid channel interface region. The first gel channel comprises two parallel rows of posts, in which each row of posts is along the length of the first gel channel and one row is along one side of the first gel channel at the first gel channel-fluid channel interface, and the other row is along the other side of the first gel channel at the second gel channel-fluid channel interface, thereby forming a first gel cage region along the length of the gel channel. All or a portion of one side of the second gel channel is flanked by, and parallel to, all or a portion of the second fluid channel, thereby creating a third gel channel-fluid channel interface region; and all or a portion of the other side of the second gel channel is flanked by, and parallel to, all or a portion of the third fluid channel, thereby creating a fourth gel channel-fluid channel interface region. The second gel channel comprises two parallel rows of posts, in which each row of posts is along the length of the second gel channel and one row is along one side of the second gel channel at the third gel channel-fluid channel interface, and the other row is along the other side of the second gel channel at the fourth gel channel-fluid channel interface, thereby forming a second gel cage region along the length of the gel channel.

The device can further comprise three fluid channel inlets and one fluid channel outlet. In addition, the device can further comprise a reservoir located in between the three fluid channel inlets and the one fluid channel outlet.

Hypoxia Device

Figure 25:
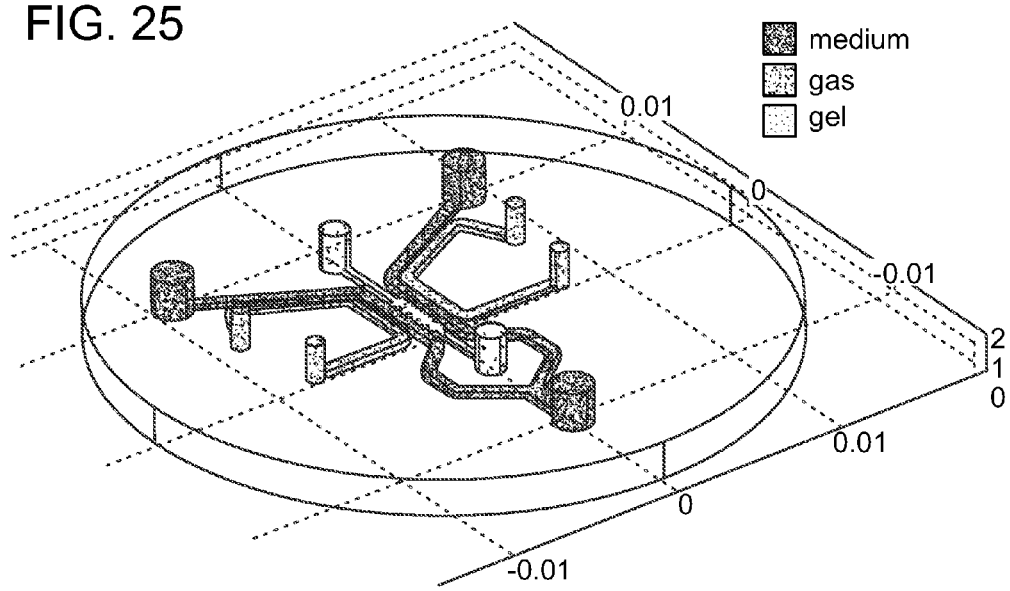
FIG. 25: Illustration of a hypoxia device. In our body, and in microfluidic devices, cells need oxygen to survive. Cells will often respond very differently based on the amount of oxygen they get; too little (hypoxia) and they act abnormally or die off, and too much (hyperoxia) and they can also act abnormally or die. Normal room oxygen concentrations are around 21%, in the body, it's more like 2-5%. Hypoxia devices (which keep oxygen levels to 2-5%) are an up-and-coming field of research. The hypoxia device runs one or more (e.g., two) more channels to the left and/or right of the media channels, and these additional channels are filled with nitrogen gas. For example, a channel sequence can be as shown in the figure: Nitrogen Channel 1→Media Channel 1→Gel Cage→Media Channel 2→Nitrogen Channel 2. By flowing nitrogen gas through these channels at higher than room pressure, the oxygen can continually be forced out of the PDMS, leaving the cells in a hypoxic state. Media can also contain dissolved oxygen, but this can be controlled, or the media can have static (no) flow, so dissolved oxygen in the media is slowly depleted by cells.

In another aspect, the device comprises a substrate comprised of an optically transparent material and (i) one or more fluid channels; (ii) one or more fluid channel inlets; (iii) one or more fluid channel outlets; (iii) one or more gel cage regions; (iv) one or more gas channels wherein all or a portion of the one or more gas channels flanks at least one side of the one or more fluid channels, the one or more gel cage regions or a combination thereof; and (v) a plurality of posts (e.g., see FIG. 25). All or a portion of each gel cage region is flanked by all or a portion of one or more fluid channels, thereby creating one or more gel cage region-fluid channel interface regions; and each gel cage region comprises at least one row of posts which forms the gel cage region. The one or more gas channels allows flow of a (one or more) gases (e.g., nitrogen, hydrogen, helium, nitrogen oxide, carbon monoxide) through the device e.g., to remove oxygen.

Nanofiber Membrane Device

Figure 24:
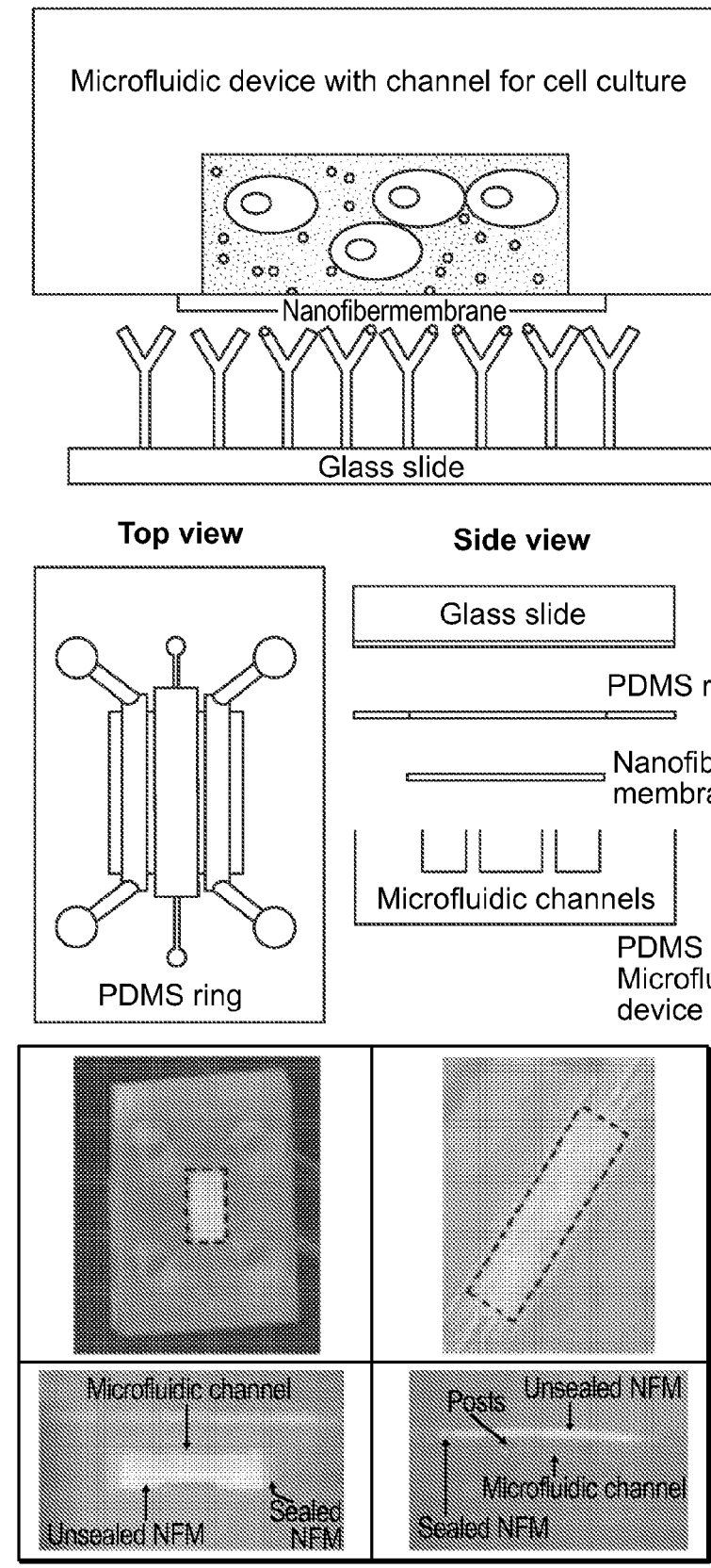
FIG. 24: Illustration of the nonfiber membrane device which allows visualization of secreted molecules from cells; it removes the microscope slide that forms the "floor" of a microfluidic device and replaces it with a standard ELISA assay with a nanofiber membrane to separate cells from the ELISA. The nanofiber membrane is selected to allow the molecule of interest to pass through it, while ensuring that the cells do not foul (contaminate) or otherwise destroy the assay, and for cell adherence. Since the molecule of interest will only leak through the area immediately below a cell, secretion of molecules of interest can be localized. The top figure (upper right and left) show cross sections of the device. A standard high throughput device uses PDMS to form walls and "ceiling" of a microchannel, while a glass coverslip is used for the "floor". ELISA assays can be patterned on glass surfaces, so in order to detect a molecule of interest, the glass coverslip used as the floor of the device can be coated with the appropriate antibodies (blue "Ys" in the upper left hand image). Cells can have difficulty attaching to this surface, and cellular migration and other biological effects may foul or destroy the coating, so a porous membrane is laid down as a "mat" on top of the glass (nanofiber membrane in both upper images). In order to keep the system water tight, a PDMS ring can be included (upper right image). The lower figure shows a fabricated device.

In another aspect, the device comprises a substrate comprised of an optically transparent material and (i) one or more fluid channels; (ii) one or more fluid channel inlets; (iii) one or more fluid channel outlets; (iii) one or more gel cage regions; (iv) a membrane that is impermeable to cells and permeable to molecules secreted by cells wherein one side of the membrane is in contact with the one or more fluid channels, the one or more gel channels or a combination thereof; and (v) a plurality of posts (e.g., see FIG. 24). All or a portion of each gel cage region is flanked by all or a portion of one or more fluid channels, thereby creating one or more gel cage region-fluid channel interface regions; and each gel cage region comprises at least one row of posts which forms the gel cage region. The device can further comprise a (one or more) capture agent that specifically binds one or more molecules secreted by a (one or more) cell and the capture agent is on the opposite side of the membrane and cannot pass through the membrane. As used herein a "capture agent" is an agent that specifically recognizes (e.g., binds to), either directly or indirectly, a molecule secreted by a cell. As will be appreciated by those of skill in the art, capture agents include all or an antigenic portion of an antibody, streptavidin/biotin and the like. In a particular aspect, the capture agent is present on a glass slide. In yet another aspect, the capture agent is able to be separated from the device (e.g., for further analysis).

Spider Device

In another aspect, the device comprises a substrate comprised of an optically transparent material and (i) one or more fluid channels; (ii) one or more fluid channel inlets; (iii) one or more fluid channel outlets; (iii) one or more gel cage regions; and (iv) a plurality of posts; wherein a portion of each fluid channel is in contact with a portion of each gel cage region and the remaining portion of each fluid channel extends away from the one or more gel cage regions (see FIGS. 6A-6C). Each gel cage region comprises three posts which form a "T-shaped" gel cage region.

In another aspect, the device comprises (i) a first fluid channel; (ii) a second fluid channel; (iii) a third fluid channel; (iv) one or more fluid inlets; (v) one or more fluid outlets; (vi) a gel cage region which forms a T-shaped gel; and (vii) a plurality of posts. In this device a portion of each fluid channel is in contact with a portion of the gel cage region and the remaining portion of each fluid channel extends away from the gel cage region. Each gel cage region comprises three posts which form a "T-shaped" gel cage region. In one aspect, each post forms a square. In particular aspects, the fluid channels are in the shape of a "C", a "V", a "U" or a combination thereof, wherein a middle region of each fluid channel contacts the gel cage region and each end of the fluid channels extend away from the gel cage region (e.g., extend radially away from the gel cage region).

Biopsy or Half-Moon Device

In another aspect, the device comprises (i) a first fluid channel; (ii) a second fluid channel; (iii) one or more fluid inlets; (iv) one or more fluid outlets; (v) an elliptical gel cage region; and (vi) a plurality of posts, wherein one side of the gel cage region is flanked by the first fluid channel thereby creating a first gel cage region-fluid channel interface, and the other side of the gel cage region is flanked by the second fluid channel thereby creating a second gel cage region-fluid channel interface (see FIG. 16A). The gel cage region comprises two parallel rows of posts centrally located in the gel cage region, thereby creating a central gel chamber, a row of posts arranged in a semicircle along the first gel cage region-fluid channel interface, thereby creating a first gel chamber that flanks one side of the central gel chamber on one side; and a row of posts arranged in a semicircle at the second gel cage region-fluid channel interface, thereby creating a second gel chamber that flanks the other side of the central gel chamber.

Thus, in some aspects, this device comprises 3 adjacent zones: (1) a central gel chamber; (2) two target tissue chambers (and/or gel chambers) flanking the central chamber; and (3) at least two media channels flanking the gel region (e.g., and can be accessible from the top surface of the device. cells can be seeded into the central gel chamber using, for example, lateral openings to the target tissue chambers. As shown in Example 3, neurons packed in the bottom channel onto the collagen gel surface extended their axons into the gel in three dimensions, and the growing axons were exposed to a chemogradient orthogonal to the direction of their growth to quantify their response and turning. Experimental and computational studies showed that a linear stable chemogradient could be established in these devices within 30 min, and lasting for up to 48 h. Cell culture studies revealed the dramatic effect of chemoattractive (netrin-1, brain pulp) and chemorepulsive (slit-2) gradients on the migration and axonal guidance of hippocampal and dorsal root ganglion neurons cultured in these devices. The stable chemogradients in these 3-channel devices could not only be used to screen potential drugs suitable for neuron pathway regeneration under disease/injury conditions, but also to study cancer cell migration and cell-cell interactions.

In a particular aspect, each gel cage region in the device can comprise 58 trapezoidal posts in two parallel rows of 29 (e.g., the high throughput device, the nanofiber membrane device). In another aspect, each gel cage region in the device comprises 40 trapezoidal posts in 2 rows of 20. In another aspect, each gel cage region in the device comprises 20 trapezoidal posts in 2 rows of 10 (e.g., the serpentine device). In another aspect, each gel cage region in the device comprises 14 trapezoidal posts in 2 rows of 7 (e.g., the hypoxia device). In another aspect, each gel cage region in the device comprises 10 trapezoidal posts in 2 parallel rows of 5 (e.g., the multiplexed device). In another aspect, each gel cage region of the device comprises 16 posts, with a configuration as follows: 5 posts form a half a circle around the left side of the central gel cage, 3 posts form the left side of the central gel cage, 3 posts form the right side of the central gel cage, and 5 posts form half a circle around the right side of the gel cage. The posts can be square, or the posts in the semi-circle can have rounded outer faces with a radius equal to the radius of the semicircle (e.g., the biopsy or half-moon device). In another aspect, each gel cage of the device comprises 3 square posts (e.g., the spider device).

Optional Components

One of the modifications that can be done to most devices is the addition of one or more gel channels, e.g., a second gel channel next to the first gel channel. Pictured in FIG. 5, the second gel channel allows for cells, such as endothelial cells, to be cultured in Media Channel 1, while Gel Channel 1 filled and Media Channel 2 are dry or temporarily filled with cell culture medium. This technique allows cells to form a monolayer on a gel surface without having to fill the other channels. This is useful if the endothelial cells require several days to form a monolayer, while any cells placed in the second gel or media channel would need to be seeded in the presence of a fully formed monolayer. A second gel channel can be added to most devices in one way or another.

Additionally, the device could be multiplexing to allow multiple devices to draw media from one reservoir, or multiple reservoirs. This allows multiple devices to be fed from a common source, or perhaps for a gradient of two different drugs to be set up. Different drug concentration combinations can then be "plucked" from the gradient and fed to a different cell-culturing site.

In addition, a biopsy and/or tissue specimen can be placed either in the media channel or the gel region. In a particular embodiment, the biopsy specimen is placed in the gel region. Also, when these "biopsy" devices are used, they usually contain several posts that are needed to hold the biopsy specimen in a particular location while the system is being filled or media being replaced. In such embodiments, a circular or half-circular gel cages can be used.

Methods of Making

In another aspect, the invention is directed to methods of producing the device and devices produced by the methods. In one embodiment, the device is manufactured in two pieces. The top piece (e.g., of polymer, glass or plastic) has micro-channels etched into it. This etching can be done, for example, with micro-machining, photolithography, hot embossing, soft lithography, microinjection molding, or any other manufacturing technique. The etched channels make the "roof" and "walls" of the channel. The "floor" of the channel is comprised of a simple flat piece (e.g., of polymer, glass, or plastic) that is bonded to the top piece. The "floor" of the device be either made of the same or a similar material as used for the "roof" and "walls" of the device, or made of a different material. Bonding can be done in a variety of ways, such as epoxies or, in the case of PDMS and glass, by exposing both pieces to pink plasma and then simply placing them in contact with each other.

Holes are created in the top piece to allow fluid flow through the micro-channels. These holes can be placed at the ends of the micro-channels, or anywhere along their length. After the top and bottom pieces are bonded, it may or may not be necessary to flow a coating chemical through the channels. Poly-d-lysine, or other chemicals, may be washed through the channels to promote cellular adhesion and stabilize the gel. This may or may not be used to control the device's hydrophobicity, as some materials require additional surface treatments in order to allow cell media to flow through them.

The device can then be filled with the gel. The gel will fill the "gel cage" or "gel cage region" completely. Surface tension will keep the gel from spilling out of the gel cage. Gel is injected into the device via the gel filling port (see FIG. 1). Different pressure-time injection profiles for gel insertion may be used to improve the quality of the injected gel. The gel may require an initial burst of injection pressure to get into the channel, then a sustained lower pressure to finish the gel filling. Alternatively, gel may be injected from both ends of the gel cage simultaneously. The gel is then allowed to harden (e.g., for one hour in a cell culture incubator). The device is then ready for cell seeding.

Accordingly, in one aspect, the invention is directed to a method of making a device comprising etching one or more fluid channels and one or more gel cage regions into a first portion of the optically transparent material and creating one or more inlets to allow flow through the one or more fluid channels and the one or more gel cage regions, thereby creating a roof and walls of the device; and bonding the first portion of the optically transparent material to a second portion of the optically transparent material that forms a floor of the device. The method can further comprise introducing a coating agent through the channels. Examples of coating agents include Poly-D-lysine, Poly Ornathene, lamin, collagen or a combination thereof. The method can further comprise contacting the surface of the device with an agent that renders the surface hydrophobic. Examples of such agents include plasma. The method can further comprising introducing a gel into the one or more gel cage regions, thereby creating one or more gel regions in the device.

Device Usage

The devices provided herein can be used for a variety of purposes. As described herein, an example of the device can be seen in FIG. 1. A first fluid channel runs parallel to, and is in contact with, the gel channel. The gel channel has two parallel rows of triangular posts (also referred to herein as micro-posts) to contain the gel, on the boundaries between the gel and fluid channels. The gel channel runs parallel to both the first and second fluid channels. The second fluid channel is also in contact with the gel channel. Outlets are drilled or otherwise created to allow fluids to flow into and out of the device.

Cells (e.g., endothelial cells) can be introduced (e.g., injected) into the first fluid channel by one of its fluid ports. The endothelial cells would be encouraged to adhere to wall of the gel-fluid channel boundary by raising the hydrostatic pressure of the first fluid channel, causing a pressure gradient across the gel channel. Fluid would percolate through the gel channel, sweeping endothelial cells with them onto the gel wall. The cells would be cultured for the desired number of days (e.g., between 3 to 7 days) of either a longer or shorter duration. As shown herein endothelial cells created "sprouts", which were 3 dimensional cone-like protrusions into the gel from the first fluid channel. These sprouts were eventually lined with endothelial cells, mimicking a blood vessel wall. Drugs can be applied to another (e.g., a second) fluid channel to attempt to retard the appearance or growth of sprouts, or to enhance sprouting frequency and size. Retardation or cessation of sprouting would indicate that the drug is a viable anti-angiogenesis drug, and would be a target for continued anti-cancer analysis. Acceleration of sprouting would indicate a good drug candidate for neovascularization, which has applications in wound healing and tissue engineering.

Furthermore, cancer cells (e.g., disassociated cells from a cancer patient's cancer biopsy) can be injected, along with a (one or more) potential anti-cancer spreading drugs or combinations of anti-cancer drugs, into another fluid channel. If, after culturing the device for several days, the cancer cells have not penetrated the endothelial layer into a region or channel (e.g., gel cage region; gel channel), then the drug or drug combination is not an anti-cancer drug. In the aspect in which the cancer cells are disassociated cells from a cancer patient's cancer biopsy, then the drug or drug combination is not appropriate to stop the spread of (or treat) that patient's cancer. For example, if cancer cells are noted in the first fluid channel, then that drug or drug combination, while possibly effective in other people, is not suitable for that individual patient.

As will be appreciated by those of skill in the art, the embodiments of the devices described herein can be produced. For example, a circular gel cage with a large port drilled into it may be suitable for placement of a whole cancer biopsy. There may be an arbitrary number of fluid channel-gel channel pairings, either all in series or all in parallel, in series and in parallel, connected to each other, and/or separated. For example, a device with a first fluid channel, a first gel channel, a second fluid channel, a second gel channel, and finally a third fluid channel, each channel separated by micro-posts, is relevant. Several gel cages may be linked together in series or parallel, with separate or common fluid channels among them. This will allow multiple cancer drugs to be tested at once, or perhaps allow one tissue biopsy to be tested with many non-interfering anti-metastasis drugs as possible. As shown herein, channels are not necessarily straight, and can (or cannot) taper off or widen throughout their length. Channel height may be quite variable, as well as the number of input ports and outlet ports.

Cancer generally begins at a specific site in the body. When it grows, it must feed itself, and to do that, induces new blood vessels to grow within it, in a process called angiogenesis. When cancer spreads, in a process known as metastasis, individual cancer cells will detach from the primary tumor and use the blood and lymphatic vessels to migrate to other parts of the body. In order to get into the blood stream, cancer cells must burrow through the blood vessel walls, particularly through endothelial cells, which line the blood vessel wall. This is known as extravasation. The cancer cells must burrow back through the blood vessel walls to get into the body's tissue after traveling, called intravasation. Angiogenesis, extravasation, and intravasation are all targets for anti-cancer drugs.

The devices described herein can be used in a variety of in-vitro assay that allow, for example, endothelial cells to form new blood vessel sprouts in a 3D gel under regulated bio-chemical conditions. A central channel allows endothelial cells to be seeded and grown. The channels next to the central channel can previously be filled with collagen (e.g., the biopsy device). The endothelial cells can grow into a monolayer on the collagen-made side walls of the central channel. New blood vessels can then sprout into the collagen from the center channel. Such devices allows very easy imaging of the extent the new drug may retard new blood vessel formation, or the extent of cancer cell infiltration into the blood vessel with and without the presence of an anti-intra- or extravascularization drug.

In the anti-angiogenesis drug discovery embodiment, new anti-intravasation drugs may be placed in one of the outer channels, and standard cell culture media in the other outer channel as a control. The device allow for quantitative assessment of the drug's efficacy. In the anti-metastasis drug discovery embodiment, the device can be treated as above, but with a cancer cells, either from a cell line or from a biopsy, to be seeded. The devices then allow easy imaging and, via downstream image processing, quantitative analysis of the number of cancer cells that have burrowed through the newly formed blood vessel sprouts, and how the process is retarded with potential anti-metastasis drugs.

In the personalized medicine embodiment, biopsied cancer cells can be placed in the device after endothelial cells, from either the patient or a cell line, are allowed to form new blood vessels. Several anti-intravascularization drugs or anti-angiogenesis drugs can then be tested in these devices. Since it appears that different patients respond to different antimetastasis drugs, these devices can be used to detect what drugs stop intravascularization and angiogenesis for that patient, and what drugs do not.

Accordingly, in one aspect, the invention is directed to a method of identifying whether an agent is angiogenic or anti-angiogenic comprising (a) introducing an agent to be assessed into the one or more fluid channels of the device as described herein, wherein one or more fluid channels of the device comprises endothelial cells and one or more gel cage regions of the device comprises a gel that forms a gel region within the gel cage region of the device; and maintaining the device under conditions in which the endothelial cells are encouraged to adhere to the gel region at the one or more gel cage region-fluid channel interface regions. Whether creation of create cone-like protrusions that are lined with endothelial cells into the gel region are enhanced or inhibited in the presence of the agent are determined and compared to a control; wherein if creation of cone-like protrusions that are lined with endothelial cells into the gel region is enhanced in the presence of the agent compared to the control, then the agent is angiogenic, and if creation of cone-like protrusions that are lined with endothelial cells into the gel is inhibited in the presence of the agent compared to the control, then the agent is anti-angiogenic. In a particular aspect, the endothelial cells are encouraged to adhere to the gel region at the gel cage region-fluid channel interface region by raising hydrostatic pressure of the fluid channel comprising the endothelial cells. In another aspect, the endothelial cells create cone-like protrusions that are lined with endothelial cells into the gel region in the presence of the agent is determined using an imaging technique.

In another aspect, the invention is directed to a method of identifying whether an agent can be used to metastasis comprising (a) introducing an agent to be assessed into the one or more fluid channels of the device described herein, wherein one or more fluid channels of the device comprises endothelial cells, one or more fluid or gel cage regions of the device comprise cancer cells, and one or more cage regions of the device comprises a gel that forms a gel region in the gel cage region of the device; and (b) maintaining the device under conditions in which the endothelial cells are encouraged to adhere to the gel region at the one or more gel cage region-fluid channel interface regions, thereby forming an endothelial layer of cells. Whether the cancer cells disperse in the gel, migrate toward and across the endothelial layers of cells or a combination thereof in the presence of the agent is determined; wherein if the cancer cells have not dispersed in the gel, migrated toward the and across the endothelial layer of cells or a combination thereof, then this indicates that the agent can be used to inhibit metastasis. In one aspect, whether the cancer cells have dispersed in the gel, migrated toward and across the endothelial layer of cells or a combination thereof in the presence of the agent is compared to a suitable control. In another aspect, the cancer cells are dissociated cells from a cancer patient's cancer biopsy.

In another aspect, the invention is directed to a method of growing blood vessels in vitro comprising (a) introducing endothelial cells into one or more fluid channels of the device provided herein, wherein one or more gel cage regions of the device further comprises a gel that forms a gel cage therein; and (b) maintaining the device under conditions in which the endothelial cells are encouraged to adhere to the gel cage at the gel cage region-fluid channel interface region and create cone-like protrusions that are lined with endothelial cells into the gel cage, thereby growing blood vessels in vitro. In one aspect, the one or more fluid channels into which the endothelial cells are introduced is central to the one or more gel cage regions in the device.

In another aspect, the invention is directed to a method of identifying whether an agent is chemoattractive agent or a chemorepulsive agent of neuronal cells comprising (a) introducing an agent to be assessed and neuronal cells into the one or more fluid channels of the device described herein, the one or more gel cage regions of the device described herein, or a combination thereof; wherein the one or more cage regions of the device comprises a gel that forms a gel region within the gel cage region of the device; and (b) maintaining the device under conditions in which the neuronal cells proliferate in the gel cage region. Whether the neuronal cells proliferate toward the agent or away from the agent; wherein if the neuronal cells proliferate toward the agent, then the agent is a chemoattractive agent of neuronal cells, and if the neuronal cells proliferate away from the agent, then the agent is a chemorepulsive agent of neuronal cells.

In another aspect, the invention is directed to a method of identifying whether an agent can be used to treat cancer comprising (a) introducing an agent to be assessed into the one or more fluid channels of the device described herein, wherein one or more gel cage regions of the device comprises a gel that forms one or more gel cages, and the gel cage further comprises a biopsy of a cancerous tissue; and (b) determining whether motility of the cancerous tissue is inhibited in the presence of the agent; wherein if motility of the cancerous tissue is inhibited, then the agent can be used to treat cancer. In one aspect, the biopsy is from cancerous tissue of an individual cancer patient and the agent can be used to treat the cancerous tissue of the cancer patient.

EXEMPLIFICATION

Example 1

Testing Concentrations of Anti-Metastatic Drugs to Keep Cancer Clusters from Migrating Methods Red colure cells are from Human Lung Cancer Cell Line A549 were transfected with H2B protein (m-Cherry), and partially disassociated, yielding cell aggregates of random sizes, between 40 um and 70 um. This was aspirated through a 100 micrometer strainer, yielding a media with cell aggregates with radii under 100 micrometers. This was poured through a second 40-micrometer filter, yielding a media with A549 aggregates between 40 and 100 micrometers. The cells were then centrifuged at 800 rpm for 2 minutes, and the media aspirated.

Collagen gel was prepared by adding 9 microliters of 1 M NaOH to 20 microliters of Phosphate Buffered Solution (BD Bioscience), and then adding 46 microliters of ultrapure H2O. Finally, 125 microliters of Type I Rat Tail Collagen at 2.5 mg/mL (BD Biosciences) were added, and mixed thoroughly.

Figure 2:
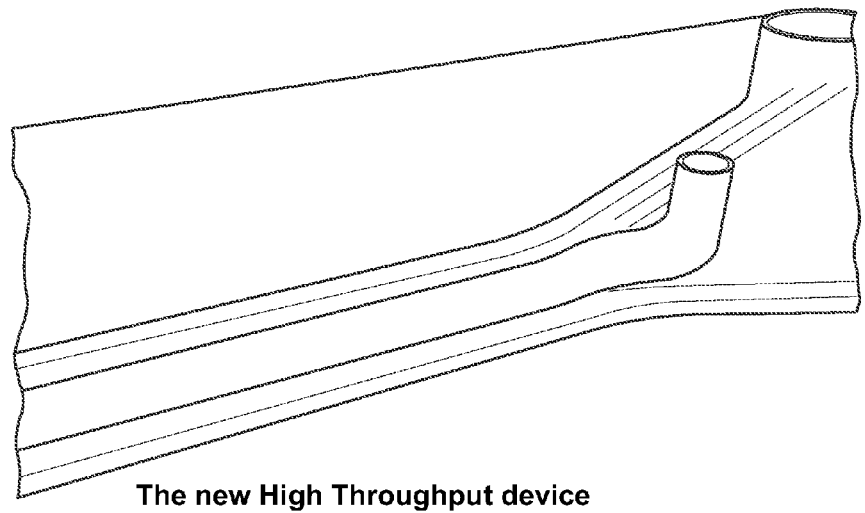
FIG. 2 is another view of the device of FIG. 1.
Figure 2:
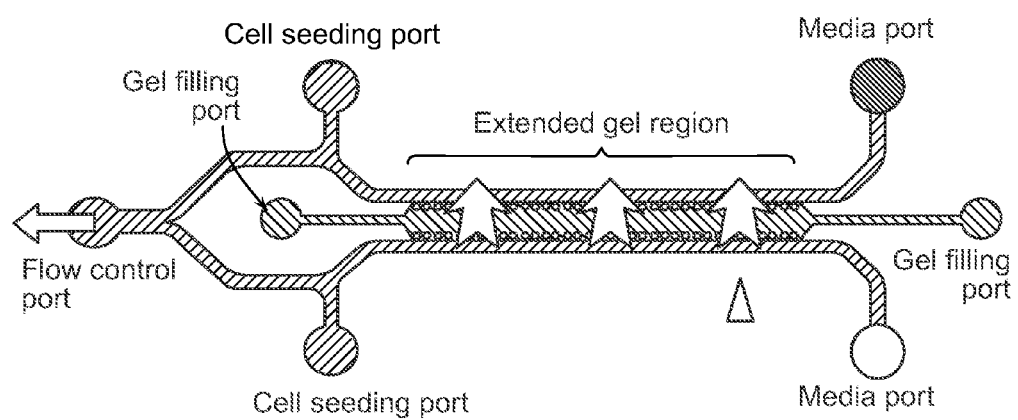

The A549 aggregates were then mixed with the collagen gel, yielding a mixture of aggregates within the gel. Ten microliters of the gel were then injected into the center channel of the device shown in FIGS. 1 and 2, yielding 36 distinct gel-fluid interfaces within the device.

Human Umbilical Vein Endothelial Cells were transfected by GFP protein label disassociated, and flowed into the first media channel. Media without cells was added to the second channel. Adding a small bubble of media on each port of the first media channel yielded a hydrostatic pressure gradient, pushing cells to the gel-media interfaces. The pressure gradient was maintained for one hour, before the bubbles were removed. The device was cultured, and imaged at 0, 12, 36, 60, 84, and 108 hours. The endothelial cells were seen to create an endothelial monolayer along the bottom of the media channel, as well as on the gel-media interface.

In the control group, no drugs were added to the system. In the experimental group, the commercial cancer anti-metastatic drug Iressa (AstraZeneca), an EGFR-TK enzyme blocker, was added to the endothelial cell medium in doses of 100 nM, 500 nM, 1000 nM, 1500 nM, and 2000 nM.

In the cases of 100 nM and 500 nM drug concentrations, the A549 cancer aggregates were seen to break up, and individual cancer cells began to migrate towards the endothelial monolayer. In the cases of 1000 nM, 1500 nM, and 2000 nM, the cancer aggregates stayed intact, and the endothelial cells began to invade into the collagen. 1000 nM was indicated to be the minimum effective dose, and a good starting point for minimum dosing studies in human subjects.

Results

This device has been used to test the necessary concentration of anti-metastatic drugs to keep cancer clusters from migrating.

Devices were prepared by injecting gel with spheres of aggregated cancer cells embedded in it. Endothelial cells were then injected into one of the two fluid ports. The cells were then cultured for 6 days, and imaged daily. Please note that there are no images from day 5.

Figure 5:
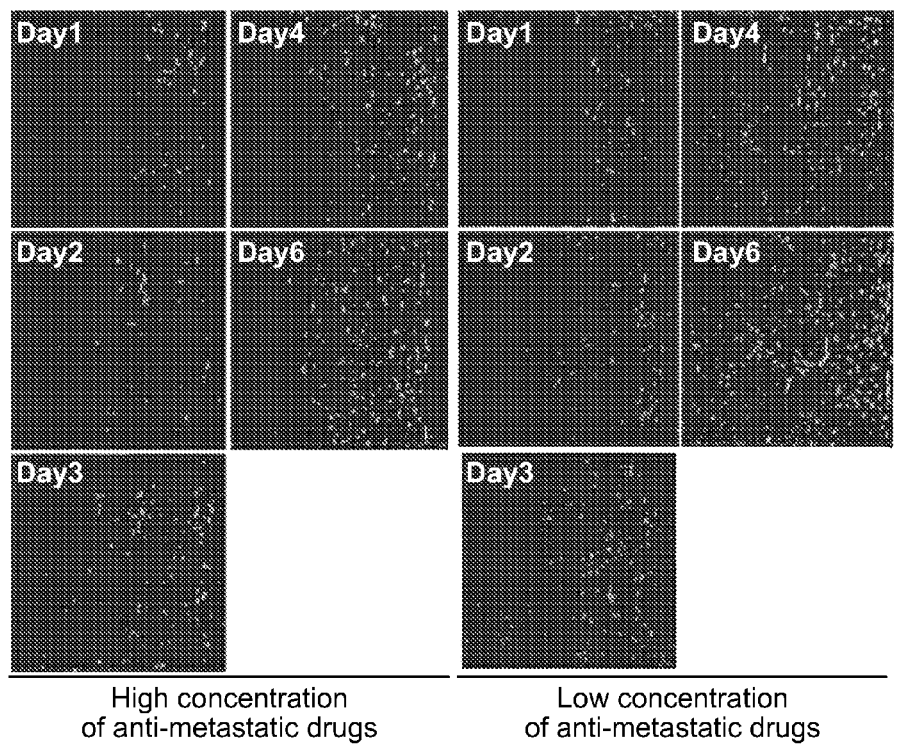
FIG. 5 shows the validation data.

FIG. 5 shows confocal images of two devices: a device loaded with high concentrations of anti-metastatic drugs, and a device with low concentrations of the drug. Cancer cell nuclei were tagged with a red fluorescent molecule, while endothelial cell nuclei fluoresced green. Initially the trapezoidal posts were difficult to see, but as the endothelial cells begin to form structures and wrap around the posts, the posts form trapezoidal shaped "holes" in the image.

Over the course of 6 days, the concentration in image 5 was high enough to keep the cells from separating and migrating. In image 6, the concentration was too low, such that the cancer cells (red) begin migrating on the third day, and by the sixth day, were beginning to enter the endothelial cell channel.

Therefore, assays can also be performed such that a full epithelial monolayer, similar to a blood vessel, is present before cancer cell introduction to a second fluid channel. Further modifications of the device to specialize it to antimetastatic drug testing include reducing the width of the central gel channel so that the gel only acts as a scaffold for the formation of endothelial cells, meaning the cancer cells would have less gel to migrate through in order to reach the endothelial cell wall.

A full epithelial monolayer, similar to a blood vessel, is present before cancer cell introduction to a second fluid channel. Further modifications of the device to specialize it to anti-metastatic drug testing include reducing the width of the central gel channel so that the gel only acts as a scaffold for the formation of endothelial cells, meaning the cancer cells would have less collagen gel to migrate through in order to reach the endothelial cell wall.

Example 2

Figure 6A:
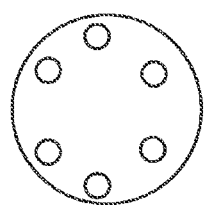
FIGS. 6A-6C (6A): Device fabrication process using soft-lithography technique. SU-8 photoresist spun-coated on silicon wafer (6A), and exposed to UV light through a transparency mask (6B). PDMS was poured on wafer and cured at 80° C. for 2 h (6C), and the cross-linked PDMS wafer peeled off (6D), ports punched and bonded with cover-slip to close the channels (6E). (6B) Design of the three-channel microfluidic device developed to study axonal turning in 3D scaffolds under a growth factor gradient. Collagen-1 was injected in the gel-filling channel and allowed to polymerize. The chemofactor of interest was added to the right channel, basal media added to the left channel to create the gradient, and neurons placed in the cell channel to respond to the gradient (6C).
Figure 6A:
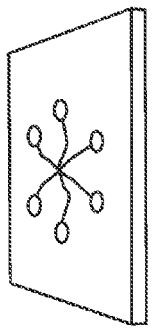
Figure 6A:
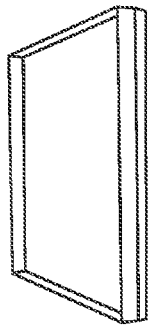
Figure 6A:
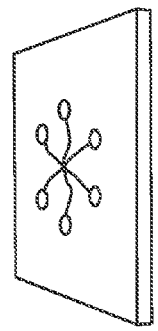
Figure 6A:
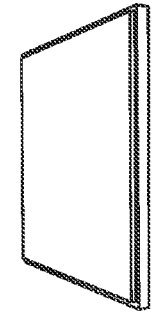
Figure 6B:
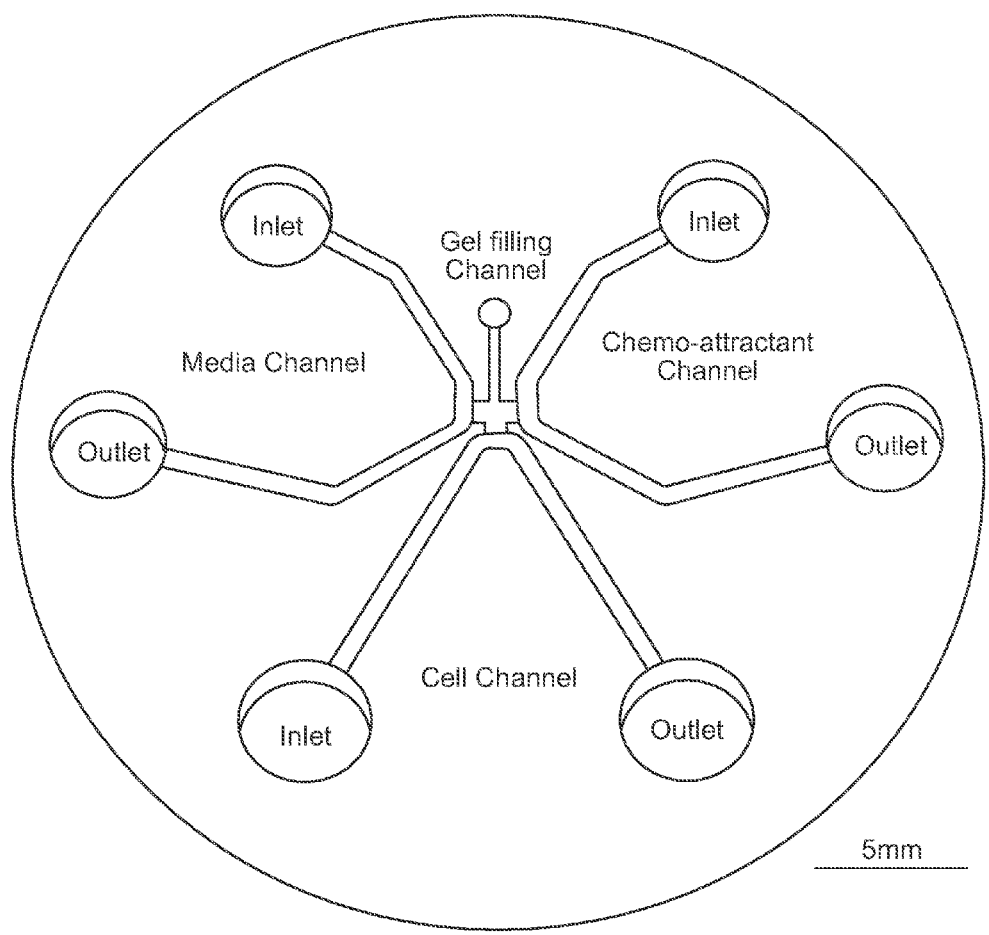
Figure 6C:
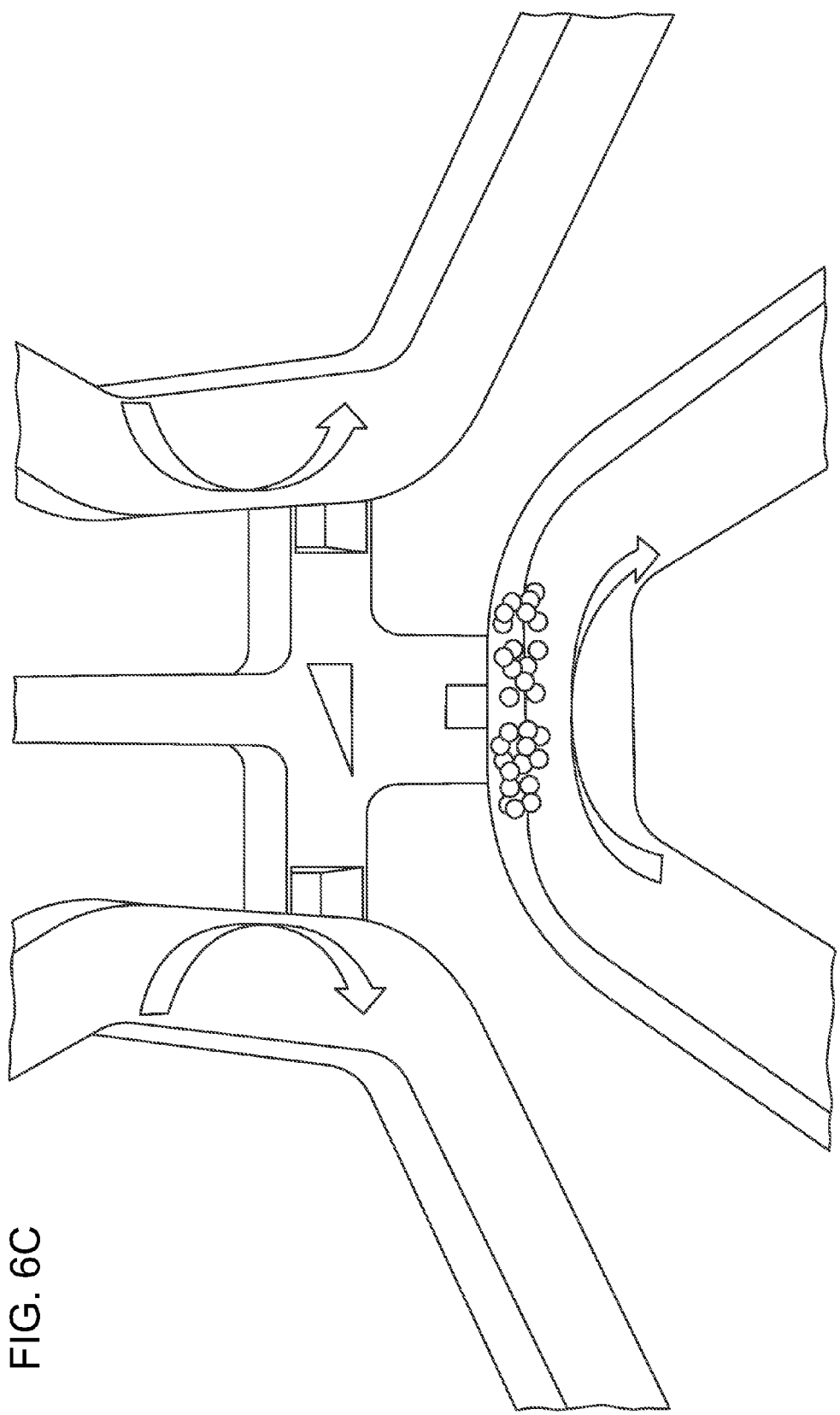

Spider Device—a High-Throughput Microfluidic Assay to Study Axonal Response to Growth Factor Gradients Studying axon guidance by diffusible or substrate bound gradients is challenging with current techniques. Described in this example is the design, fabrication and utility of one embodiment of the microfluidic devices provided herein used to study axon guidance under chemogradients. Experimental and computational studies demonstrated the establishment of a linear gradient of guidance cue within 30 min which was stable for up to 48 h. The gradient was found to be insensitive to external perturbations such as media change and movement of device. The effects of netrin-1 (0.1-10 µg/mL) and brain pulp (0.1 µL/mL) were evaluated for their chemoattractive potential on axonal turning, while slit-2 (62.5 or 250 ng/mL) was studied for its chemorepellant properties. Hippocampal or dorsal root ganglion (DRG) neurons were seeded into a microchannel and packed onto the surface of a 3D collagen gel (FIGS. 6A-6C). Axons grew into the matrix in three dimensions, and a gradient of guidance cue was created orthogonal to the direction of axon growth to impact axonal guidance. The average turning angle of each axon was measured and averaged across multiple devices cultured under similar conditions to quantify the effect of guidance cue gradient. Significant positive turning towards gradient were measured in the presence of brain pulp and netrin-1 (1 µg/mL), relative to control cultures which received no external guidance cue (p<0.001). Netrin-1 released from transfected fibroblasts had the most positive turning effect of all the chemoattractive cues tested (p<0.001). Slit-2 exhibited strong chemorepellant characteristics on both hippocampal and DRG axonal guidance at 250 ng/mL concentration. Slit-2 also showed similar behavior on DRG neuron invasion into 3D collagen gel (p<0.01 relative to control cultures). Taken together, the results indicate the utility of this microfluidic device to generate stable chemogradients for studying neurobiology, cell migration and proliferation, matrix remodeling and co-cultures with other cell lines, with additional applications in cancer biology, tissue engineering and regenerative medicine.

During nervous system development, a tightly-regulated complex neural network is established by spatio-temporal regulation of guidance molecules that direct the growth of axons along specific pathways to reach the target (B. J. Dickson, Science, 2002, 298, 1959). This process depends on the chemoaffinity of growth cones (the tip of the axon) to sense and respond to multiple attractive and repulsive guidance cues operating at different length scales in the environment (M. Tessier-Lavigne and C. S. Goodman, Science, 1996, 274, 1123). However, the precision and mechanism by which the distribution of guidance cues is maintained within the nervous system are not clear yet. Earlier studies have shown that axons fail to regenerate and accurately reestablish the lost neuronal network connections after an injury to the central nervous system (F. C. Wagner Jr and G. J. Dohrmann, Surg. Neurol., 1975, 3, 125). Although numerous tissue engineering strategies have been explored to promote axonal regeneration at the site of injury (M. B. Bunge, J. Spinal. Cord. Med., 2008, 31, 262), successful practical realization of these approaches is contingent upon elucidating the effects of concentration and gradient of developmentally important guidance cues on axonal response and turning, especially in the inflammatory environment at the injury site.

Growth factor gradients have been implicated in many biological phenomena, including cell migration, axonal outgrowth and guidance in the nervous system (G. Curing a and G. M. Smith, Exp. Neurol., 2008, 209, 333). It is now generally accepted that axonal outgrowth and guidance is controlled by the concerted action of attractive and repulsive cues, arranged in substrate-bound and diffusible gradients, to facilitate tunneling through the tissue and connecting to distant targets (D. Mortimer, T., et al., Trends. Neurosci, 2008, 31, 90). Although in vivo studies on axonal guidance are very powerful in identifying cues relevant to neural development, it is impossible to control the microenvironment around the neurons, and evaluate the role of the multitude of cues to which the growth cones are exposed. Thus, researchers have developed numerous experimental and computational techniques to study the effects of growth factors on axonal outgrowth in vitro. In one technique, neural tissue explants embedded in collagen matrix are exposed to a source of guidance cue released from transfected cells (H. Chen, et al., Neuron, 1998, 21, 1283), microbeads (B. Genc, et al., PLOS Biology, 2004, 2, 2112), or diffusible micropatterned gradients on collagen gel surface (W. J. Rosoff, et al., Nat. Neurosci., 2004, 7, 678). Quantification in these assays was limited to comparing axonal outgrowth from the explants on the higher and lower concentration sides. While these methods have been successful in identifying the global response of neuronal population to a specific cue, they generally fail to distinguish the effect of biomolecular gradients on axonal outgrowth and guidance. Moreover, it is difficult to trace individual axons as they grow out of the explant, due to dense axonal overlap on 2-dimensional coated surfaces. In other in vitro assays, discontinuous (S. Lang, et al., Anal. Bioanal. Chem., 2007, 390, 809) or continuous (S. Dertinger, et al., Proc. Natl. Acad. Sci. U.S.A., 2002, 99, 12542) gradients of guidance cues are printed onto the surface, on which the neurons are cultured and axonal growth observed. However, limitations of this technique include its suitability for only substrate-bound gradients and 2D cultures.

Micropipette turning assays have commonly been used for studying axonal guidance in vitro (Z. Pujic, et al, J. Neurosci. Meth., 2008, 170, 220). In this case, the micropipette serves as a continuous point source of chemoattractant, producing a growth factor gradient by diffusion to guide axonal growth (J. Q. Zheng, et al., Nature, 1994, 368, 140; K. Buck and J. Zheng, J. Neurosci., 2002, 22, 9358). However, the gradient produced by localized factor delivery is spatially non-uniform, and varies significantly with the molecular weight of diffusible cue, height of micropipette tip, and the pulse duration and frequency. In all the above assays, the gradients generated by these traditional methods are unstable, difficult to quantify and often lack defined spatio-temporal control. To elucidate the complexities of physiologically-relevant growth factor gradients and their specific cell signaling processes, user-defined control over the spatio-temporal distribution of growth factor in the extracellular matrix environment and the ability to directly visualize cells within that environment is needed.

Over the past decade, microfluidic devices have gained popularity in cell culture applications, because they offer a great platform for studying how cells respond to alterations of their physical and chemical milieu (N. Li, A. Tourovskaia and A. Folch, Crit. Rev. Biomed. Eng., 2003, 31, 423; J. El-Ali, et al., Nature, 2006, 442, 403; A. Folch and M. Toner, Ann. Rev. Biomed. Eng., 2000, 2, 227). These devices are also useful for creating well-defined 2D and 3D cell culture environments with micrometer precision, quantifiable characterization and experimental reproducibility. Microfluidic devices with simple geometries were also developed to demonstrate the effect of mechanical constraints on axon growth (H. Francisco, et al., Biomaterials, 2007, 28, 3398), though axonal turning and guidance could not be studied in these devices. Similarly microfluidic gradient mixers were developed to study the effects of substrate-bound gradients on neuron survival and outgrowth (G. Li, J. Lui and D. Hoffman-Kim, Ann. Biomed. Eng., 2008, 36, 889). Since neurons are sensitive to shear stress (S. S. Margulies, et al., J. Biomech., 1990, 23, 823), these gradient-generating devices are likely not be suitable to study the effect of diffusible cues on axonal turning. in this context, devices employing surface gradients of substrate cues (L. J. Millet, et al., Lab Chip, 2010, 10, 1525) or microgroove based devices might be more effective in isolating axons from their cell bodies and studying axonal outgrowth and turning (A. M. Taylor, et al., Nat. Methods., 2005, 2, 599; J. W. Park, et al., Nat. Protoc, 2006, 1, 2128). It can be seen from these earlier studies that stable biomolecular gradients can be created in microfluidic devices for studying axonal guidance by diffusible growth factors, although no such microfluidic system exists yet.

Described herein is one embodiment of a microfluidic devices that can be used to study axon guidance by diffusible factors in a 3D in vitro cell culture model. Neurons cultured in this device extended axons in a 3D physiological configuration, and the growing axons were exposed to guidance cue gradients orthogonal to the direction of axonal growth, making it an effective technique for studying axon guidance. Demonstrated herein is the utility of this embodiment of the device to study the effects of various chemoattractive/repulsive guidance cues, their mode of delivery and variable concentration gradients, on hippocampal and DRG neuron axonal outgrowth and turning. This embodiment of the device can also be used, for example, to study other neuronal cell types, either as single cultures or co-cultures. This device also has applications at the interface of neuroscience, developmental cell biology, advanced biomaterials and microfluidic technology.

Experimental

Microfluidic Device: Design and Fabrication

This embodiment of the microfluidic device was fabricated using photolithography and soft-lithography techniques described in detail elsewhere (Y. N. Xia and G. M. Whitesides, Ann. Rev. Mat. Sci., 1998, 28, 154). As shown in FIGS. 6A-6C, the device design was created in AutoCAD (Autodesk, San Rafael, Calif.) and a transparency mask was created from the CAD file and printed by a high-resolution printer (PageWorks, MA). The silicon wafer was first spin-coated with a SU-8 photoresist at a thickness of 120 µm. A transparency mask printed with the negative pattern of the device was placed over the wafer and exposed to UV-light, which crosslinked the photoresist in the exposed areas. The uncrosslinked photoresist was then washed away, resulting in a silicon wafer layered with the positive relief of the device. Microfluidic devices were made by replica molding (J. C. McDonald, et al., Electrophoresis, 2000, 21, 27) polydimethylsiloxane (PDMS; Dow Corning, USA) and curing the degassed elastomer mix (10:1, base: curing agent) against the silicon master in an 80° C. oven for 2.5 h. Polymerized PDMS devices were peeled off the silicon master, individual devices (30 mm diameter, 1 cm height) cut out and inlets and outlets cored down to microfluidic channels using standard 4 mm and 1 mm diameter punching tools. Prior to cell culture, PDMS wafers were cleaned and autoclaved at 120° C. for 35 min (20 min sterilization/15 min dry) to remove uncrosslinked PDMS and sterilize the devices. The glass cover-slips were air-dusted and autoclaved for 30 min (dry). PDMS surface and cover-slips were oxidized by air plasma for 45 sec, before they were bonded together, closing the channels and completing the device fabrication. This surface treatment ensured an irreversible bond between PDMS and cover-slip and also helped prevent leaks. To restore hydrophobicity before filling the gel scaffold, the devices were kept at 80° C. overnight.

Collagen Gel Loading in PDMS Devices

Sterilized PDMS wafers with their surfaces rendered hydrophobic (as described above) were filled with 2 mg/mL collagen type I isolated from rat tail (BD Biosciences, San Jose, Calif.; stored at 4° C.). Collagen solution was prepared by adding collagen stock solution to a mixture of 10×PBS, 1 M NaOH and tissue culture grade water to obtain a 2 mg/mL solution at pH 7.4. A cold pipette tip pre-loaded with 2 µL of collagen gel solution was carefully lowered into the gel-loading port of the device, and ice cold gel was microinjected into the device until the designated gel-region within the micro-pillars was filled (FIGS. 6A-6C). This process was repeated in multiple devices for each experimental condition. After gel injection, PDMS wafers were placed in a humidified container to prevent the hydrogels from drying out, and the gels were allowed to polymerize for 30 min at 37° C. in a humidified incubator. The gel was filled 24 h prior to experiment and left in the incubator to allow any air bubbles in the microchannels to resorb.

Gradient Simulation and Visualization

Figure 7A:
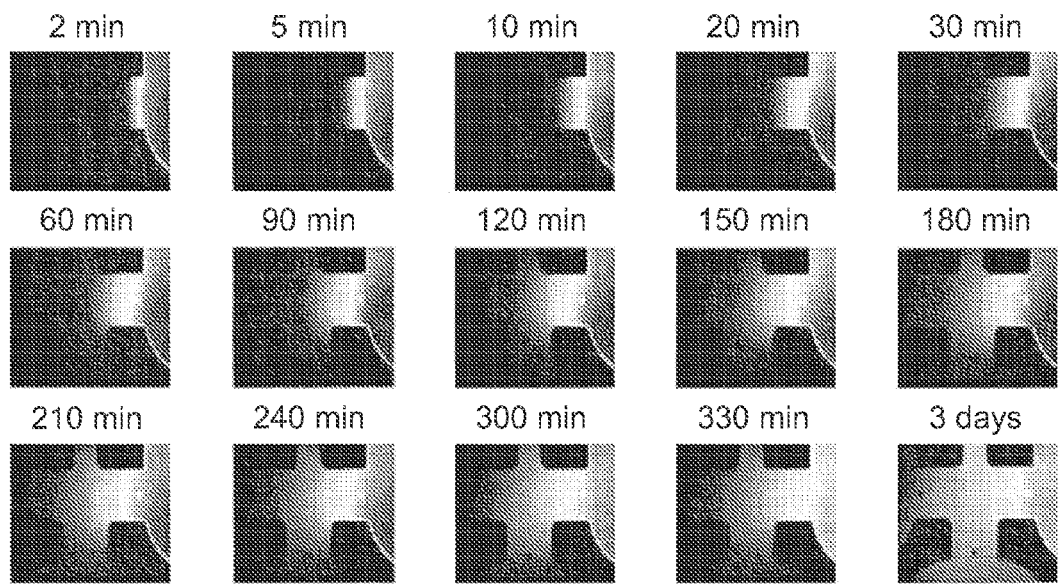
FIGS. 7A-7B. (7A): Time-lapse, normalized images of fluorescent dextran (40 kDa; 10 µM) gradient across the 3D collagen gel in the device. (7B) Diffusion profiles analyzed by averaging a horizontal rectangle along the gel region and plotted against its position in the channel. A snapshot of dextran gradient at 24 h time point was shown for reference.
Figure 7B:
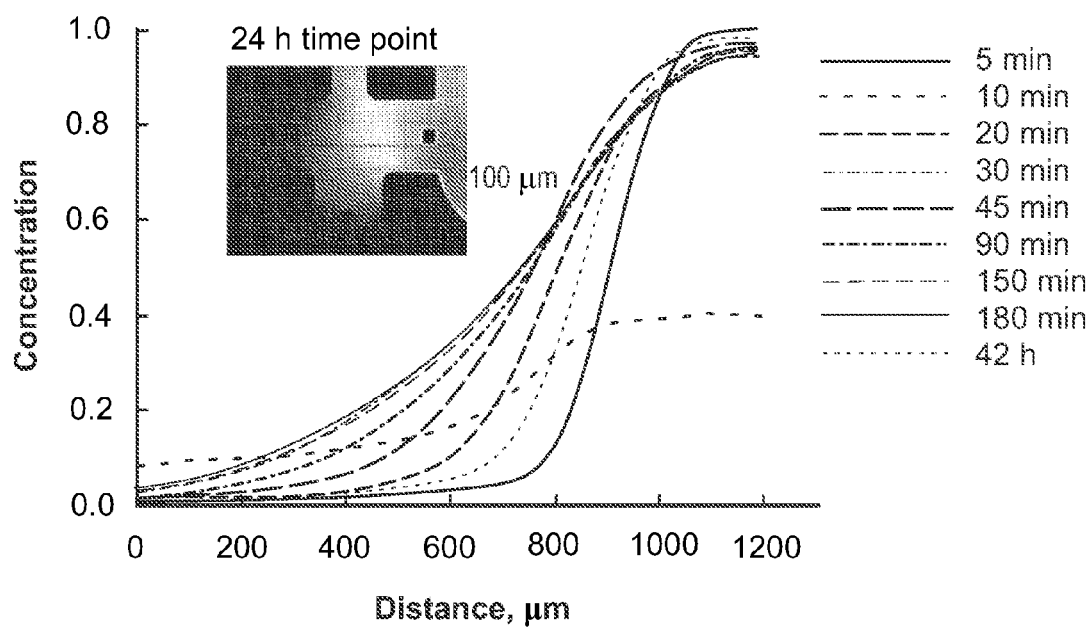

Following collagen gel polymerization, microfluidic channels were filled with cell culture media. Gradient studies were performed under static conditions with the media in chemoattractant channel (FIGS. 6A-6C) replaced by a dilute solution of florescent FITC-dextran (40 kDa, Invitrogen, CA) at an initial concentration of 10 µM (FIGS. 7A-7B). The other channels were filled with serum-free media. Florescent intensity was captured with a Nikon TE300 fluorescent microscope (Nikon Instruments Inc., NY, USA). A series of florescent images of the gel region were acquired every 5 min for the first half hour and then every half hour for 3-5 h, with a Hamamatsu camera (Hamamatsu, Shizuoka, Japan) using Openlab (Improvision, Waltham, Mass.) data acquisition software. The device was then brought to the incubator to prevent excess drying of the media, and further images were taken at 6 h intervals by stabilizing the device on a microscope stand for 30 min before acquiring the images. Image processing of time-lapse florescent images was performed using a custom written code in MATLAB (MathWorks, Natick, Mass.), to obtain the changes in florescent intensity across the gel at each time point. Briefly, pixel values were normalized by subtracting the background intensity value, and then divided by the maximum pixel value of 10 µM Dextran. The diffusion profiles were analyzed by averaging a horizontal rectangle along the gel region and plotted against its position in the channel (FIG. 7B insert). Each image was normalized with the maximum and minimum obtained from the first image of the series.

A diffusion-convection-reaction finite element model was developed in COMSOL (Burlington, Mass.) for quantifying concentration gradients under different experimental conditions and performing parametric analyses. Constant concentration boundary conditions were defined at the numerical model boundaries, for representing source conditions at the inlet ($C_{SOURCE}$) and sink conditions at the outlet ($C_{SINK}$) of the control channel and at the gel filling port. For the transient simulations, the initial concentration in the condition channel was set equal to that of the inlet to simulate the characterization experiments. Based on the experimental characteristics, a diffusion coefficient of $D_{GEL}=5.1\times10^{-11}$ m$^2$/s was defined for the growth-factor diffusion inside the collagen matrix, which agreed with the reported values of Helm et al. (C. L. Helm, et al., Proc. Natl. Acad. Sci. U.S.A., 2005, 102, 15779), for 2 mg/mL collagen gels. The diffusion coefficient inside the medium-containing channels was set to $D_M=6\times10^{-11}$ m$^2$/s, according the Stokes-Einstein relationship for a 40 kDa molecular weight protein. The numerical grid for performing the simulations consisted of approximately 400,000 finite elements.

Neuron Isolation and Culture

Figure 11A:
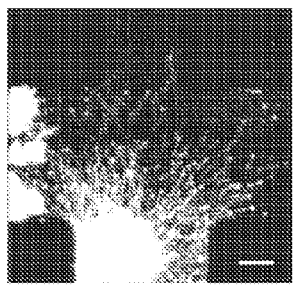
FIGS. 11A-11K: Axon guidance of hippocampal neurons by chemoattractants. Fluorescent images of rhodamine-stained neurons cultured in the presence of netrin-1 released from transfected fibroblasts in right channel and normal fibroblasts in left channel (11A), and normal fibroblasts in both the channels (11B). Confocal microscopy images of DCC-transfected neurons cultured with exogenous supplementation of 1 µg/mL lab-purified netrin-1 (11C). Confocal microscopy images of rhodamine-stained neurons which received 0.1 µg/mL lab-purified netrin-1 (11D), 1 µg/mL lab-purified netrin-1 (11E), and 10 µg/mL lab-purified netrin-1 (11F), no exogenous supplements (11G), and 100 ng/mL brain pulp (11H). Metrics used for quantification of axonal turning into each quadrant (11I), and the percentage of axons measured in each quadrant in response to external chemo attractive gradients (11J and 11K).
Figure 11B:
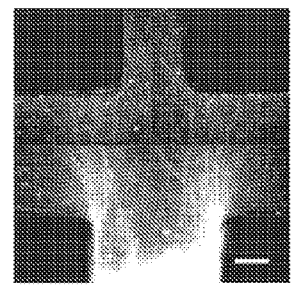
Figure 11C:
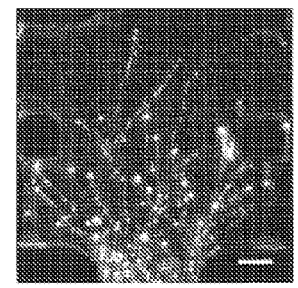

Primary hippocampal neurons and dorsal root ganglion (DRG) neurons cultured in the devices were obtained from embryonic day 14.5-16.5 mice as per protocols described in detail elsewhere (R. Li, Methods. Cell. Biol., 1998, 57, 167; W. E. Thomas, Life. Sci., 1986, 38, 297; A. V. Kwiatkowski, et al., Neuron, 2007, 56, 441). Cells from micro-dissected cortices were dissociated and resuspended in serum-free media at a final concentration of 10 million cells/mL. The neurons were seeded into the devices (n=10 devices per test condition) immediately after dissociation and cultured for 1-2 days, with serum-free media replaced in all the channels twice a day, before any guidance cue was introduced. All cell cultures were maintained in a humidified incubator at 5% $CO_2$ and 37° C. For netrin-1 studies (FIGS. 11A-11C), hippocampal neurons were transfected using amaxa nucleofection, with a pmax-gfp plasmid cotransfected with a plasmid expressing DCC (deleted in colorectal cancer) receptor (M. J. Galko and M. Tessier-Lavigne, Science, 2000, 289, 1365).

Guidance Cue Addition and Media Change

Netrin-1 added in the channel was obtained from multiple sources: lab-isolated (T. Serafini, et al., Cell, 1994, 78, 409) netrin-1 (0.1-10 µg/mL), and netrin-1 released from cDNA transfected stable fibroblast cell line (K. Löw, et al., J. Neurosci., 2008, 28, 1099). Commercially obtained netrin-1 at 0.1 µg/mL (R&D Systems, Minneapolis, Minn.) was also tested under similar culture conditions, but did not provide any additional advantage compared to that of lab-purified netrin-1. Brain pulp was prepared in the lab from fresh whole mouse brain tissues. Briefly, the brain tissue was homogenized with a rotor stator in a hypotonic solution supplemented with protease inhibitors (protease inhibitor cocktail; Roche, USA), filtered, total protein content measured using a Bradford protein assay, and diluted to 0.1 µL/mL concentration. The chemorepellant used was Slit-2 (62.5 or 250 ng/mL; R&D Systems, Minneapolis, Minn.)). For chemosensing studies, the medium was removed from all the ports after 24-48 h of cell seeding, and 350 µL medium containing known concentration of guidance cue was introduced in the chemoattractant channel, and 350 µL serum-free media in each of the remaining two channels. For the experiments with netrin-1 being released from fibroblasts, transfected fibroblasts ($1\times10^5$ cells) were seeded in the chemoattractant channel (source), and normal fibroblasts (non-transfected, $1\times10^5$ cells) were seeded in the left channel (sink). Unless transfected, these normal fibroblasts do not inherently release netrin into the media. Netrin-1 released from the transfected fibroblasts diffuses across the collagen-1 gel and creates a gradient. The medium was changed at regular intervals to maintain chemogradient at all times. The control devices which received no guidance cues were cultured in the same procedure as with test cases.

Characterization of Axonal Outgrowth and Turning

Figure 11D:
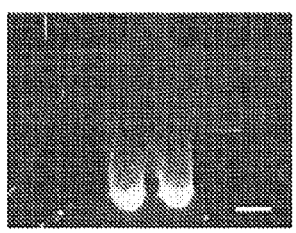
Figure 11E:
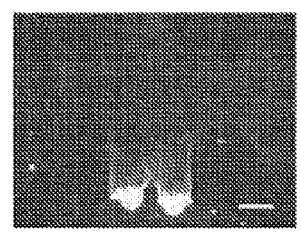
Figure 11F:
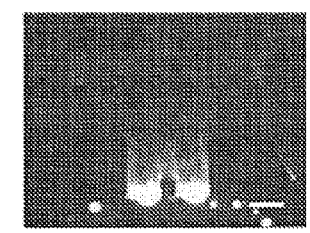
Figure 11G:
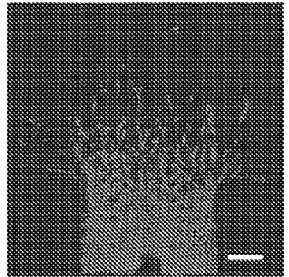
Figure 11H:
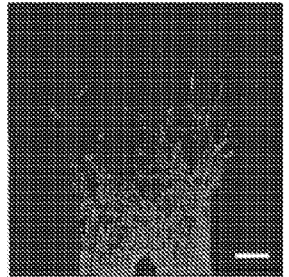
Figure 11I:
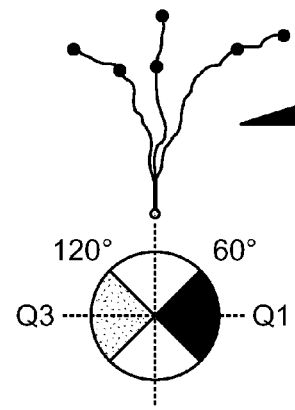
Figure 11J:
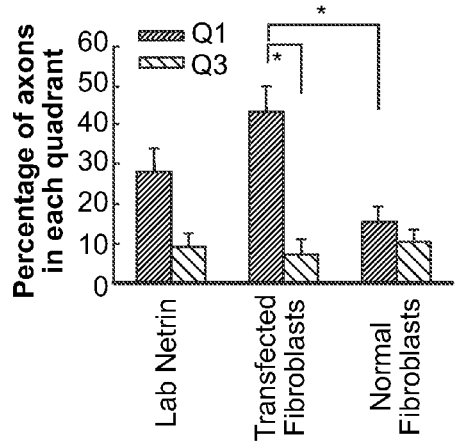

Phase-contrast, fluorescence and confocal microscopy were used to characterize axonal distribution and quantify axonal turning in 3D collagen gels within the devices. Florescent and phase contrast images were acquired with a Nikon TE300 microscope equipped with a Hamamatsu camera and Openlab image acquisition software. Axonal and nuclei staining were performed after fixation with 4% PFA (30 min). The fixed samples were rinsed thrice with 1× phosphate buffered saline (PBS), treated with 0.1% Triton-X (1-2 min), rinsed with 1×PBS twice followed by the infusion of a mixture of DAPI (for nuclei) and rhodamine phalloidin (for actin; 30 min) and a final wash step with 1×PBS. Confocal images were collected using a spinning disk confocal microscope (Zeiss Axiovert 200M) furnished with Imaging Suite (Perkins Elmer Life Science) acquisition software. A series of 20 optical serial sections (5 µm thick) were obtained and the aligned images stacked and rendered for 3D visualization using Imaris (Bitplane, MN). The last 100 µm segment along the length of each axon leading to the growth cone was traced with NeuronJ (E. Meijering, et al., Cytometry. Part. A, 2004, 58, 167), and the angle this segment makes with the horizontal line (0°) was measured. Among the four quadrants, values in Q1 (−60° to +60°) reflect growth towards guidance cue and in Q3 (120° to 240°) reflect turning away from the guidance cue (FIG. 11J). The number of axons in quadrants 1 and 3 were counted for devices cultured under similar conditions, and the statistical significance values between test cases and control cultures (with no guidance cues) were computed using Mann-Whitney test by averaging the data from all the devices under each experimental condition. For studies with DRGs, the number of cells which migrated into each quadrant were measured and quantified using a similar procedure.

Results and Discussion

Microfluidic Device Implementation

Microfluidic devices offer numerous practical advantages, including high-throughput and low-cost experiments, when compared to traditional gradient-generating techniques. Besides, microfluidic devices require smaller amounts of valuable reagents which allow multiple gradient-generating cell culture environments to be implemented in parallel. This embodiment of the microfluidic device described in this study offers a novel platform for studying axon guidance in vitro, and provides many unique features not available in other current techniques. (i) It is easy to fabricate, simple to manipulate, and more reliable in reproducibility of experiments. (ii) The cells can be cultured in more physiological conditions, since they are packed in a tissue-like conformation and project axons through a 3D matrix (FIGS. 10A-10B). The good survival and outgrowth from these neurons demonstrates a very effective way to culture these cells in the future. (iii) Chemogradients across the 3D gel can be established at desired time points to study the axonal biology. (iv) With multiple axons per device and multiple devices per batch, it is possible to obtain statistical significance of data with just one experiment. (v) It is easy to track axons in 3D and compute turning angles, and therefore conducive to detailed analysis and quantification. Such devices offer an efficient tool for studying axonal guidance in response to chemo-gradients.

In this embodiment, the device has a T-shaped gel region and three channels (FIG. 6B): media channel, cell channel and guidance cue channel. As the guidance cue added to the right channel diffuses through the gel, the other channels act as a sink for the same, thereby creating a gradient across the gel. Earlier studies have shown that the initial axonal outgrowth of cortical neurons is predominantly directed laterally, with progressive axonal turning at more lateral positions (H. B. M. Uylings, et al., in The cerebral cortex of the rat, ed. B. Kolb, and R. C. Tees, Cambridge, MIT, 1990, p 35-76). Thus, relative to cell body, the gel region was purposefully designed long enough to visualize enhanced axonal outgrowth and eventual turning response to the gradient. The three PDMS posts (FIG. 6C) provide structural support to the gel and prevent gel from overflowing into the media channels. Thus, in this configuration, the direction of axonal outgrowth is orthogonal to the direction of gradient, making this an effective setup to study axonal guidance. In addition, when cells must be circulated through a narrow channel, there is an increased risk of damage by shear stress. The chamber in which the cells were cultured was several orders of magnitude larger than the cell body, greatly increasing their chance of survival and reducing their tendency for mechanical activation while introducing them into the device.

Previous studies have demonstrated that cells within 3D scaffolds exist in a more natural environment in which they contact other cells and ECM in three dimensions, and are therefore expected to more closely evoke native cell responses than 2D substrates (W. M. Saltzman, et al., Ann. N.Y. Acad. Sci., 1992, 665, 259). Since cellular gene expression within 3D scaffolds (as in native tissues) can be regulated by scaffold-derived cues including cell adhesion molecules, growth factors, and mechanical stimuli, ECM-based scaffolds are more likely to evoke native integrin-ECM interactions and preserve the native cell phenotype (L. Griffith and M. Swartz, Nat. Rev., 2006, 7, 211). A reconstituted hydrogel of type I collagen at 2 mg/ml was used in the present study producing a polymerized matrix with fibrils 50-200 nm in diameter, and pore size on the order of 0.5-1 µm (N. Yamamura, et al., Tissue. Eng., 2007, 13, 1443). Although this is not the predominant extracellular matrix component in the nervous system, type I collagen has been successfully used by other researchers to study axonal outgrowth in both 2D and 3D cultures (G. Li and D. Hoffman-Kim, Tissue. Eng. Part B., 2008, 14, 33). The studies described herein also showed no adverse affects of collagen type I on neuron survival and axonal outgrowth, compared to matrigel or peptide gel.

Gradient Establishment and Stabilization

Figure 14:
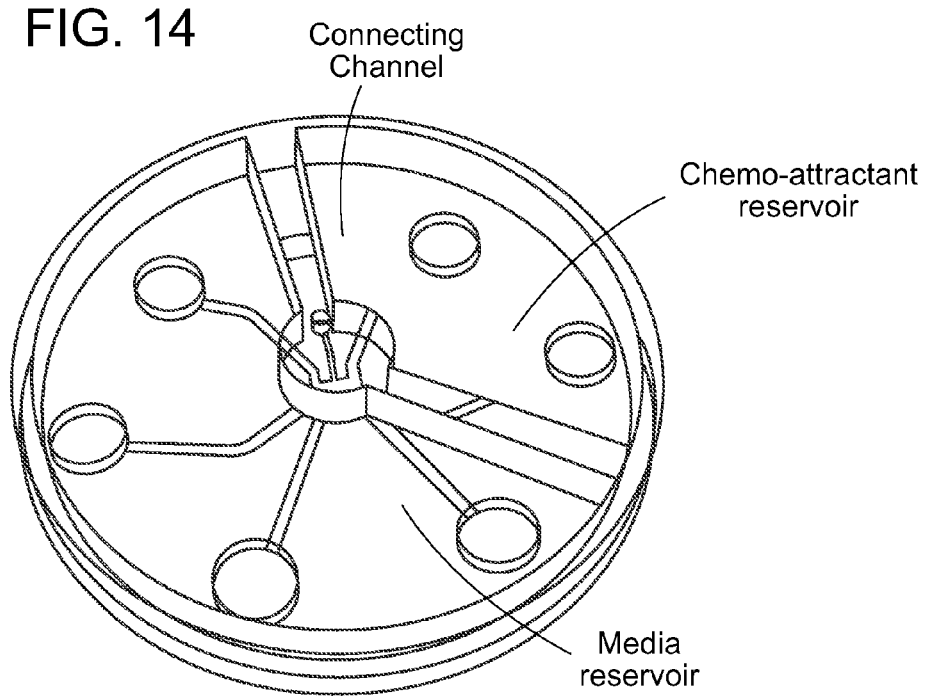
FIG. 14: A reservoir cover is added to the top of the device to ensure equalized pressures. The chemoattractant ports are covered with the chemoattractant reservoir (green) and the media and cell channel ports are covers with the media reservoir (blue). A small channel connects both reservoirs to allow differential pressure to equilibrate.
Figure 14:
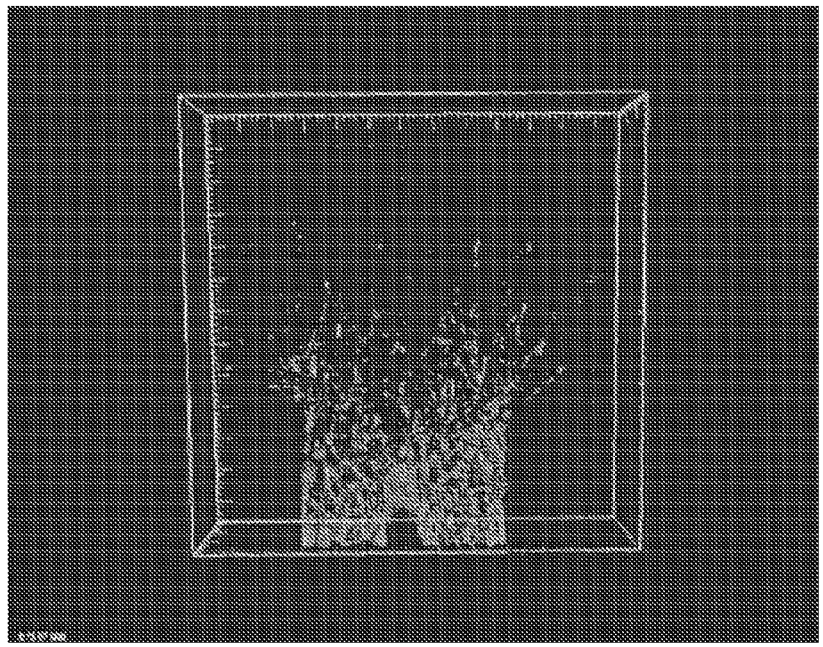
Figure 15A:
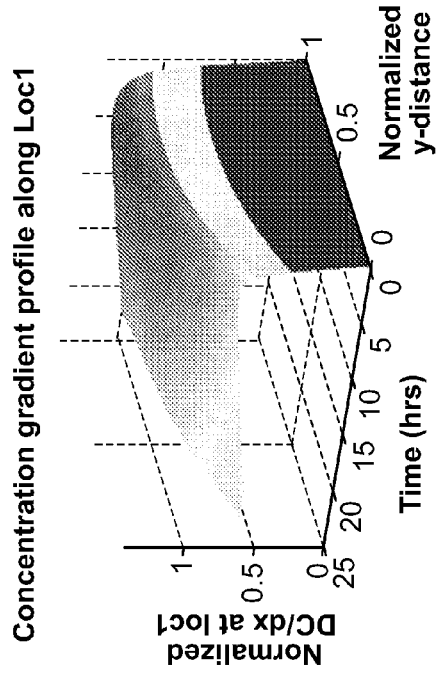
FIGS. 15A-15C (15A): Evaluation of concentration gradient along y-axis using COMSOL. Concentration distribution at steady state with arrows marking the y-axis locations 1 (black) and 2 (green), along which concentration gradients are plotted in (15B) and (15C), respectively. The concentration gradient values at both locations are normalized with respect to the maximum concentration gradient value at location 1 after 24 h ($DC/dx=1$), in order to allow for direct quantitative comparison. When chemoattractant is added at $t=0$, the concentration gradient at locations 1 and 2 does not exist. However, after 24 h during medium replacement, a stable concentration gradient will have been established.
Figure 15B:
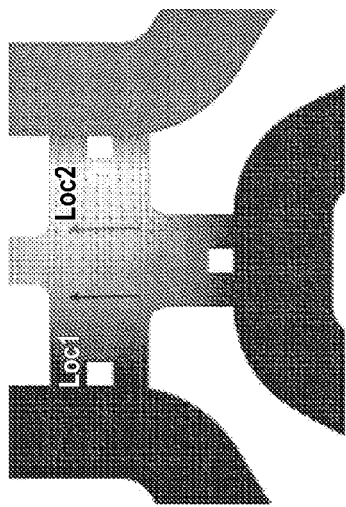
Figure 15C:
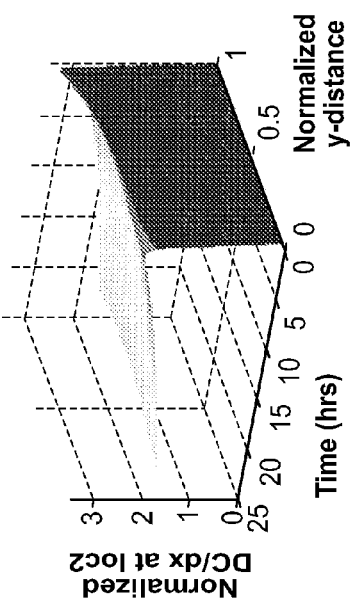

In preliminary gradient experiments, the chemoattractant was added to the device, and all the other channels were filled with the same volume of serum-free media, in an attempt to create gradient. However, convection through the gel was observed even after equilibrium was attained, probably due to small pressure differences between side channels, which might prevent diffusion gradient from forming across the gel. Thus, to maintain equilibrated pressures in the side channels, a PDMS reservoir system with two sections was installed on top of the device (FIG. 14). One section of reservoir filled with chemoattractant (or repellant) medium enclosed the chemoattractant channel port, while the other section filled with media covered the other two channels. A small channel shaped as a half cylinder with diameter 1.5 mm connected these two sections of the reservoir and allowed pressures to equilibrate, thus preserving the gradient through the gel. FIG. 7A shows typical time-dependent snapshots of gradient obtained with a 40 kDa FITC-Dextran in the device, from which concentration profiles across the gel were obtained over the 2 day period (FIG. 7B). It was observed that the gradient takes 30 min to establish, and a stable gradient could be maintained for up to 2 days. The gradient advanced to the left in the initial 30 min, after which the chemoattractant slowly depleted from the chemoattractant channel around the entrance of the gel, gradually accumulating in the cell and media channels. Deviations from a linear gradient are evident due to the T-shape of the gel region, but these are highly reproducible, can be predicted by the computational model, and can be accounted for in the interpretation of the experiments if necessary.

Recent studies by Goodhill et al., quantified gradient detection by growth cones using both experimental and computational approaches (G. J. Goodhill, Trends. Neurosci., 1998, 21, 226; G. J. Goodhill and J. S. Urbach, J. Neurobiol., 1999, 31, 230; J. S. Urbach and G. J. Goodhill, Neurocomputing, 1999, 26, 39). The steepness of the gradient was characterized by the change in concentration across the width of growth cone (~10 µm) normalized by the concentration at the source and expressed as a percentage. While gradients as low as 0.1% can be detected by growth cones, a 1% gradient is sufficient to induce some guidance and 10% steepness will induce robust guidance (W. J. Rosoff, et al. Nat. Neurosci., 2004, 7, 678). Since growth cones are exposed to a variety of gradients in their native environment in vivo, they likely adapt their morphology and directional guidance depending on the magnitude of the concentration and the gradient (J. Xu, W. Rosoff, et al., Development, 2005, 132, 45). If the concentration is high enough that all the cell surface receptors are saturated, then no amount of gradient will have any effect. On the other hand, if the concentration is too low, very few receptors would be activated despite higher gradients. Thus, it is best to decouple the effects of concentration levels and gradient on cellular responses to growth factors. Regardless of the perceived distortions (e.g., gel-filling region and the cell channel acting as sinks) to the maintenance of a uniform linear gradient across the gel in the device, the finite-element modeling predicted a steepness of 3-4% at the concentrations studied, which should induce robust axonal guidance. To maintain a steeper gradient for extended periods in this device, for example, the media can be slowly passed through the side-channels during the experiment. This procedure not only constantly replenishes chemoattractant in the source channel, but also prevents its accumulation in cell and media channels which might act as sinks.

Gradient Sensitivity to External Perturbations

Figure 8A:
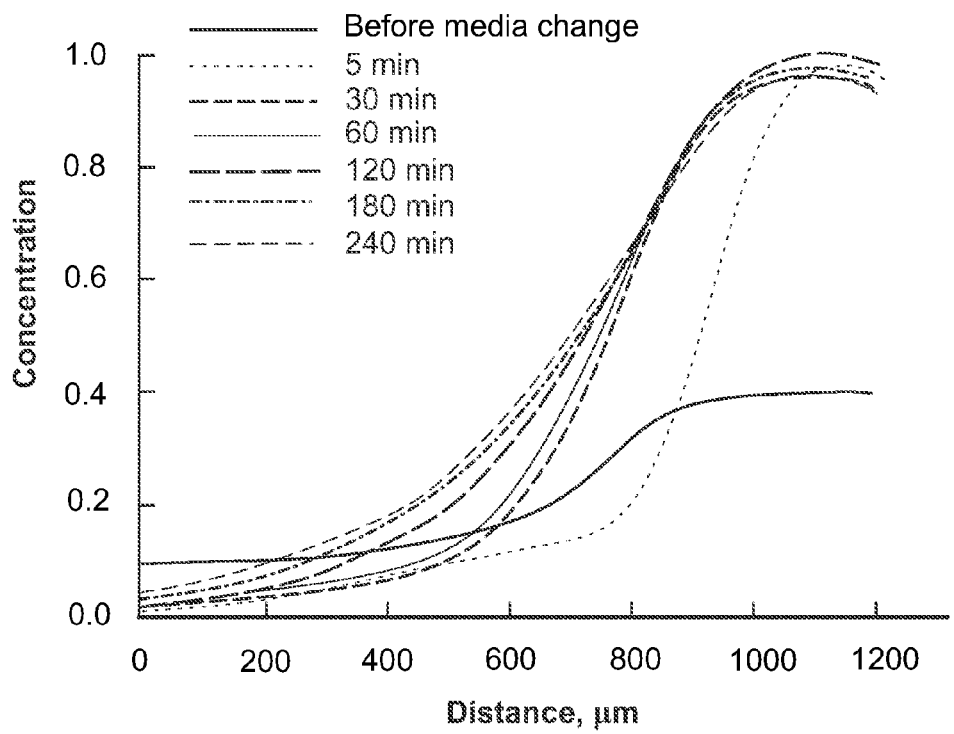
FIGS. 8A-8B: Role of external perturbations on gradient reestablishment in the device. (8A) Dextran gradient was completely reestablished in 30 min after media was changed in all the channels. (8B) The stable linear gradient remained unchanged even after the addition of 150 µL of dextran solution to the chemoattractant reservoir.
Figure 8B:
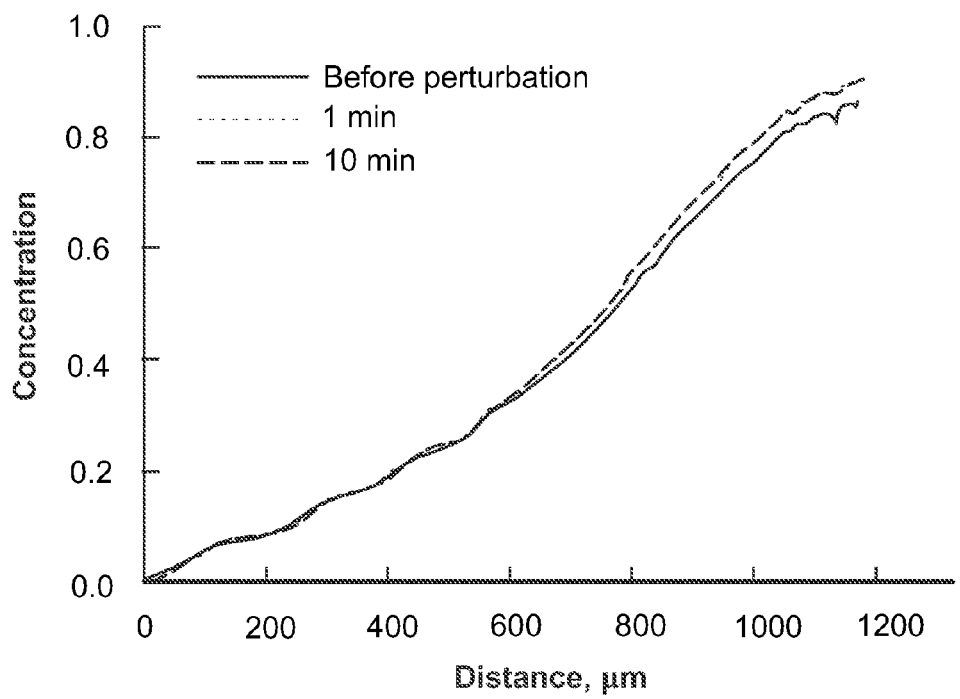
Figure 9A:
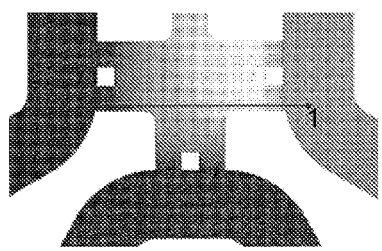
FIGS. 9A-9D: Simulation of guidance cue transport in the microfluidic device. The steady-state concentration distribution across the collagen scaffold region after 24 h of guidance cue addition (9A) and the concentration gradient (9C) in the device; spatio-temporal evolution of the concentration profiles (9B) and concentration gradient (9D) in these regions plotted along the dashed line shown in (9A) and (9C), respectively.
Figure 9B:
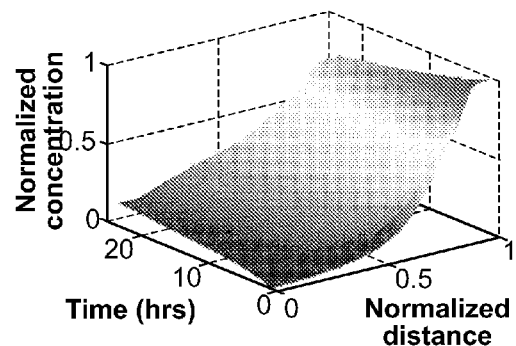
Figure 9C:
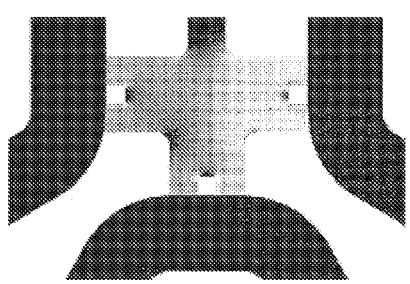
Figure 9D:
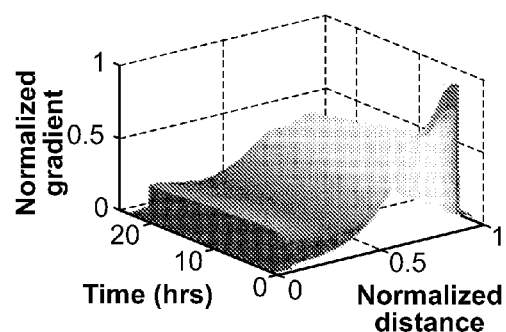

The role of external perturbations on gradient establishment and stabilization during the experiment were tested in two ways: media change in the device at regular interval, or adding 150 µL of Dextran solution to the chemoattractant reservoir on top of the device. When media is changed in all the channels, the reservoirs and ports are emptied and replaced with fresh media. Concentrations were monitored during media change (FIG. 8A), showing that the higher concentrations from fresh media reestablished the gradient across the gel within ~30 min, after which it remained stable. In a second experiment, 150 µL of dextran solution was added to the chemoattractant reservoir which already contains 350 µL of media. This caused a significant increase in the pressure in this compartment which was effectively equilibrated through the reservoir-connecting channel, and not through the gel disrupting the gradient (FIG. 8B). Similarly, when the device was moved from incubator (at equilibrium) to microscope for imaging, or when the cells were packed onto the gel surface, or when the incubator itself experienced vibrations, no significant changes in gradient across the gel were observed. Thus, these detailed studies show that the gradient was formed with a high degree of certainty in the device, and also recovers well from external perturbations.

Despite these advances, a number of uncontrollable variables may contribute to gradient disruption in cell culture studies. For example, rapid evaporation of media, variation in concentration of collagen gel near PDMS wall or posts, unwashed debris in channels, binding of guidance cues to matrix, etc. Thus, necessary precautions were taken to autoclave and visually check the devices before use, utilize collagen gel from the same batch, and maintain same collagen gel to neuron ratio for all experiments.

Gradient Simulation

The finite element model of the time dependent gradient in the microfluidic device was shown in FIGS. 9A-9D. The steady state concentration distribution across the gel region in the device (FIG. 9A) and the spatio-temporal evolution of the concentration profiles in this region (FIG. 9B) were calculated. In the initial conditions, the chemoattractant channel has a concentration of 1, and the cell and media channels have concentrations of 0. The concentration gradient (slope of the concentration profile) distribution across the gel region was shown in FIG. 9C for comparison, and its spatiotemporal evolution profile in FIG. 9D. It could be seen that it takes approximately 30 min for a quasi-steady concentration gradient to be established, which decays slowly within 42 h, after which the chemoattractant and the medium are replenished. Furthermore, the decaying concentration profiles lead to a more uniform gradient within the gel region over time. Thus, an exact knowledge of the concentration gradients and the ability to perform detailed parametric studies using simulations are important for quantifying the chemoattractant gradient sensed by the growth cone to interpret their turning potential.

Effect of Chemoattractive Gradients on Hippocampal Axonal Guidance

The goal of the experiment was to make the neurons grow their axons in three-dimensions into the collagen gel and neurons have a greater chance of doing this if they are close to the gel surface. Therefore, the cells were packed onto the gel by a differential pressure across the gel as shown in FIG. 10A-10B. The cell suspension (20 μL) was placed in the inlet port of the cell channel and the media from all the other ports was removed. The high pressure created by the cell droplet induced flow through the cell channel towards the outlet port. The low pressure in both the media channel and chemoattractant channel creates a small flow through the gel, thus packing the cells onto the gel surface. By reestablishing the pressure difference several times, the flow was restored, and the cell density packed onto gel increased. The medium was refreshed in the cell channel 2 h after cell seeding to eliminate the unpacked cells.

Netrin-1, a diffusible chemoattractant produced by floor plate cells, plays an important role in creating a complex pattern of neuronal connectivity by facilitating directed migration of immature neurons over long distances. Some studies have shown that netrin-1 mediates outgrowth of commissural axons in vitro via DCC receptor (K. Keino-Masu, et al., Cell, 1996, 87, 175), and enhances retinal neurite extension (T. Serafini, T., et al., Cell, 1994, 78, 409; K. J. Mitchell, et al., Neuron, 1996, 17, 203). On the other hand, netrin-1 has been shown to be a chemorepellent for oligodendrocyte precursor cells in the embryonic spinal cord, mediated via a netrin-receptor complex consisting of DCC and an UNC-5 homolog (UNC5H) (A. A. Jarjour, et al., J. Neurosci., 2003, 23, 3735). Thus, in this study, the role of netrin-1, delivered through different modes, on hippocampal neuron axonal turning and guidance in microfluidic devices was evaluated in vitro.

Figure 11K:
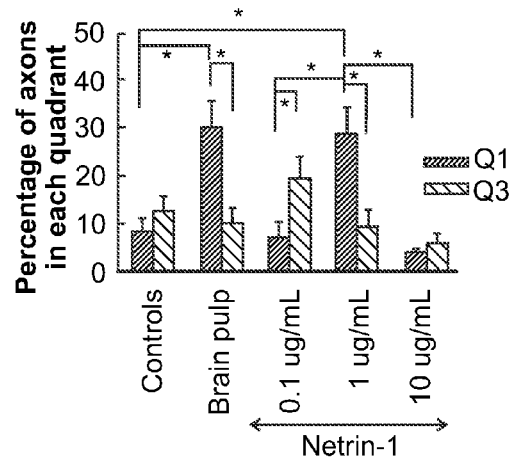

When hippocampal neurons were cultured in control devices with no exogenous guidance cues (FIG. 11G), as expected, a majority of axons showed no axonal turning in the absence of any gradient, with only 8.3±3.1% of total axons observed in Q1 and 12.6±4.3% in Q3 (n=151 axons; FIG. 11K). The axonal turning of neurons cultured with netrin-transfected fibroblasts in the right channel and normal fibroblasts in left channel was shown in FIG. 11A, while the axonal turning in cultures with normal fibroblasts in both the channels was shown in FIG. 11B. Netrin-1 released from netrin-transfected fibroblasts (FIG. 11A) attracted 43.4±6.5% of total axons towards the gradient, with only 7.1±3.9% turning away (p<0.001 for Q1 vs. Q3; n=119 axons). In contrast, cultures with normal fibroblasts on both sides with no netrin gradient across the gel (FIG. 11B), exhibited no preferential axonal turning (p>0.6 for Q1 vs. Q3; n=45 axons). In the former case, netrin-transfected fibroblasts might be continuously replenishing the gradient across the collagen gel, with the cell and media channels acting as a sink, although the exact concentration of netrin-1 being released from these cells is not known at this point. Netrin-1 release from fibroblasts therefore induced a three-fold increase in axonal turning towards the gradient when compared to non-transfected fibroblast cultures (p<0.001; FIG. 11J), and a 5-fold increase when compared to fibroblast-free controls (p<0.001).

Exogenous supplementation of 1 μg/mL lab-purified netrin-1 encouraged DCC-transfected hippocampal axonal turning towards the gradient (27.8±6% in Q1; p<0.01 for Q1 vs. Q3; n=117 axons) (FIG. 11C), thrice the percentage of axons which turned into Q1 in netrin-free controls (p<0.001 vs. controls). The differential effects of lab-purified netrin concentration on axonal response to the gradient were then tested. FIGS. 11D, 11E, 11F) shows the representative fluorescent images of hippocampal neurons cultured in the presence of 0.1, 1 and 10 μg/mL netrin, respectively. Quantitative analysis of these images revealed that 0.1 and 10 μg/mL netrin had no significant chemoattractive effect on axonal turning (n=138 and n=38 axons, respectively), compared to netrin-free controls. Higher concentration of netrin (10 μg/mL) might be saturating the growth cone receptors suppressing axonal turning, which would explain the lack of any response at this dosage, although further studies are needed to validate these hypotheses. In conclusion, 1 μg/mL netrin offered the maximum positive effect on axonal turning towards the gradient in the dosage range studied (p<0.03 for 1 μg/mL netrin vs. all the other cases).

When hippocampal neuron cultures were supplemented with 0.1 μg/mL brain pulp (FIG. 11H; n=28 axons), a 3-fold increase in axonal turning toward the gradient was observed relative to controls (p<0.005). It was interesting to note that the hippocampal neurons responded in a similar fashion to both 1 μg/mL lab-netrin and 0.1 μg/mL brain pulp, as evident from the percentage of axons in Q1 and Q3 under both cases (FIG. 11K). Though it is difficult to identify the composition and concentration of each guidance cue in the brain pulp mixture which contributed to this axonal response, it nevertheless shows the utility of this device to co-culture tissue specimen with a known cell type.

The cell culture environment is much more physiological in this device, when compared to 2D flat surface culture systems or the micropipette turning assay. Chemoattractant was added to the device when the growing neurites reach the horizontal section of the gel, where the gradient becomes nearly orthogonal to the direction of axonal growth. The growth cone is extremely dynamic in nature and fulfills three important functions—sense environmental cues, transmit signals to the cell body and navigate the axon accordingly.

Growth cone migration is mediated by the polymerization/depolymerization of cytoskeletal elements connected with the actin superstructure, which have been implicated to play a key role in axonal outgrowth, growth cone motility and guidance (D. Bentley and A. Toroian-Raymond, Nature, 1986, 323, 712). Guidance cues were shown to induce chemotropic responses in growth cones in vitro, wherein attractive cues such as netrin-1 or BDNF (brain-derived neurotrophic factor) extend the cytoskeletal network in the direction of the gradient (J. Yao, et al., Nat. Neurosci., 2006, 9, 1265), and proteins induced by repulsive cues such as slit-2 or semaphorin3A cause it to collapse (M. Piper, et al., Neuron, 2006, 49, 215). Netrin-1 is secreted into the matrix environment and binds to ECM molecules and cell membranes, thereby determining the range of netrin diffusion and signaling (T. E. Kennedy, Biochem. Cell. Biol., 2000, 78, 569). Thus, netrin signaling could be due to activation of different netrin receptors, with DCC (deleted in colorectal cancer) receptors primarily mediating netrin attraction (M. J. Barallobre, et al., Brain. Res. Rev., 2005, 49, 22), and UNC-5 receptors mediating netrin repulsion (H. M. Cooper, et al., Clin. Exp. Pharmacol. Physiol., 1999, 26, 749). Since collagen-1 is not the predominant component of ECM in the nervous system, netrin-1 binding to 3D collagen-1 scaffold will be negligible, which will not affect the perceived gradient by axons in the device. Results from this study also confirm that the hippocampal axonal turning toward the 1 µg/mL netrin-1 gradient is mediated by DCC-receptor activation in the leading edge of growth cone, as shown by the bright fluorescence of DCC receptors in FIG. 11C.

Effect of Slit-2 on Hippocampal Axonal Turning

Slit-2 has been shown to repel neuronal precursors migrating from the anterior subventricular zone to the olfactory bulb (W. Wu, et al., Nature, 1999, 400, 331), repel spinal motor axons in culture by interacting with Robo receptor (H. S. et al., Cell, 1999, 96, 807) and mediate glioma cell guidance in the brain. In conjunction with their Robo transmembrane receptor counterparts, slit-2 has been shown to regulate guidance of commissural axons at the midline (K. Brose, et al., Cell, 1999, 96, 795). In addition, cells that are repelled by slit-2 were shown to lose responsiveness towards netrins (E. Stein and M. Tessier-Lavigne, Science, 2001, 291, 1928; F. Causeret, et al., Dev. Biol., 2002, 246, 429). In knock-out mice lacking expression of slit-2, severe defects in axonal guidance were observed in vivo (A. S. Plump, et al., Neuron, 2002, 33, 219). Since slit-2 is a well studied chemorepellant in neurobiology, the effects of slit-2 gradient on axonal turning in microfluidic devices were evaluated.

Figure 12A:
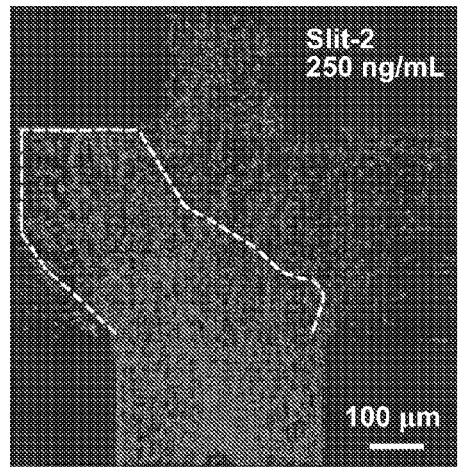
FIGS. 12A-12C: Dose-dependent effect of slit-2 on hippocampal axonal turning in device. Confocal microscopy images of rhodamine-stained neurons in response to gradient created from slit-2 at 250 ng/mL (12A) and 62.5 ng/mL (12B). (12C) Quantification of axonal turning revealed that 250 ng/mL slit-2 repelled significantly higher number of axons down the gradient compared to 62.5 ng/mL slit-2 or additive-free controls.
Figure 12B:
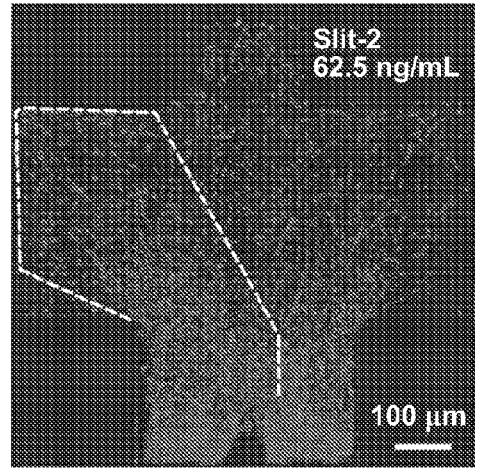
Figure 12C:
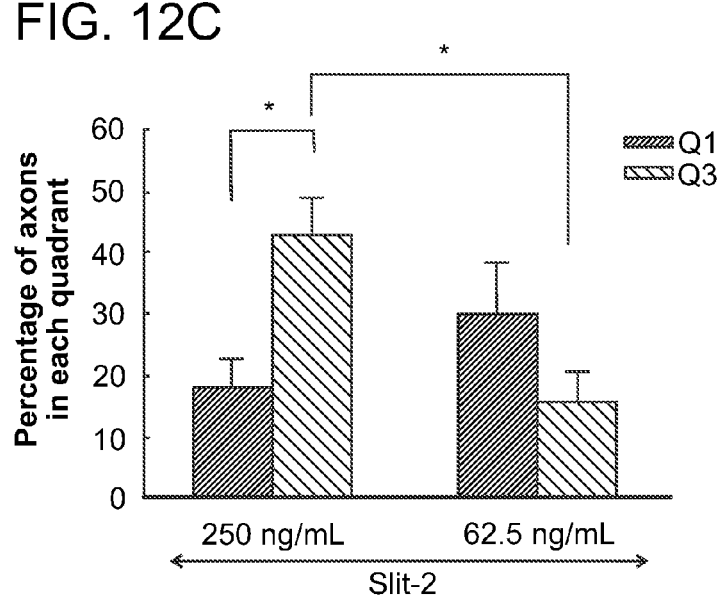

FIGS. 12A-12C shows representative collapsed 3D confocal microscopy images of hippocampal axonal turning at two different levels of slit-2 gradient. At the higher gradient (250 ng/mL in the right channel) slit-2 acted as a strong chemorepellant (FIG. 12A), as evident from the percentage of axons in Q3 (42.6±9.1%) compared to that in Q1 (18.2±4.5%; p<0.001 for Q3 vs. Q1; n=64 axons). In contrast, slit-2 at 62.5 ng/mL did not exhibit similar strong repellent characteristics (FIG. 12B; n=51 axons). Increasing the concentration of slit-2 from 62.5 ng/mL to 250 ng/mL almost tripled the percentage of axons that turned away from the high concentration (p<0.001; FIG. 12C). Relative to controls which received no cues (FIG. 11G), 250 ng/mL slit-2 enhanced axonal turning down the gradient by 3.4-fold (p<0.001). However, further studies are needed to understand the molecular mechanisms (e.g., receptor activation) behind this interesting behavior of slit-2 on hippocampal axonal turning.

Effect of Slit-2 on DRG Migration and Axonal Turning

Figure 13A:
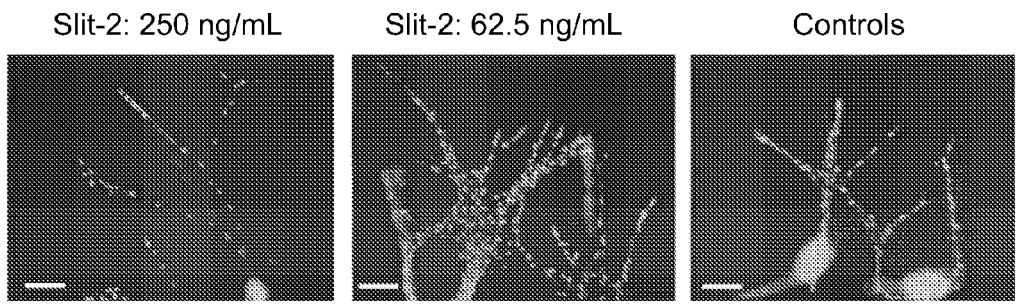
FIGS. 13A-13D: (13A) DRG neuronal (DAPI-stained) migration into 3D collagen scaffold in response to gradients created by 250 ng/mL and 62.5 ng/mL slit-2 in the device. DRG migration in control cultures which received no slit-2 was shown for comparison. (13B) Fluorescent microscopy images of extensive DRG axonal outgrowth and turning in response to 250 ng/mL slit-2 and no slit-2 (controls), after neuron migration was inhibited by adding 5-fluorouracil (5-FU) to the culture media. Quantification of DRG neuron migration (13C) and axonal turning (13D) into each quadrant, under slit-2 gradient and in control cultures. Significant chemorepellant behavior of 250 ng/mL slit-2 on DRG neuron migration and axonal outgrowth down the gradient was observed relative to controls ($p<0.001$).

When DRG explants were seeded in the cell channel, neurons overpopulated the devices and aggressively migrated into 3D collagen gel (FIG. 13A). In control cultures, which received no slit-2, neuronal migration into Q1 and Q3 remained similar due to lack of any gradient in the scaffold (18.5±5.1% in Q1 vs. 15±6.5% in Q3). On the other hand, 250 ng/mL slit-2 addition drastically increased DRG neuron migration down the gradient (74±12.5% in Q3; FIG. 8C), by 5-fold relative to controls (p<0.001 vs. controls), and by 2.7-fold relative to 62.5 ng/mL slit-2 gradient (p<0.01). Migrating neurons have been shown to utilize different signaling pathways than chemotaxing growth cones, by extending multiple processes and then selecting the one that appears most favorable for migration (M. W. Ward, et al., Mol. Cell. Neurosci., 2005, 30, 378). The leading tip of the migrating DRG neurons (FIG. 13A) preceding the cell body supports this strategy adapted under chemogradients. Taken together, these results indicates that slit-2 at 250 ng/mL concentration expresses a strong chemorepellant effect for DRG neuron migration, and further studies are needed to elicit the molecular mechanisms behind these observations.

Figure 13B:
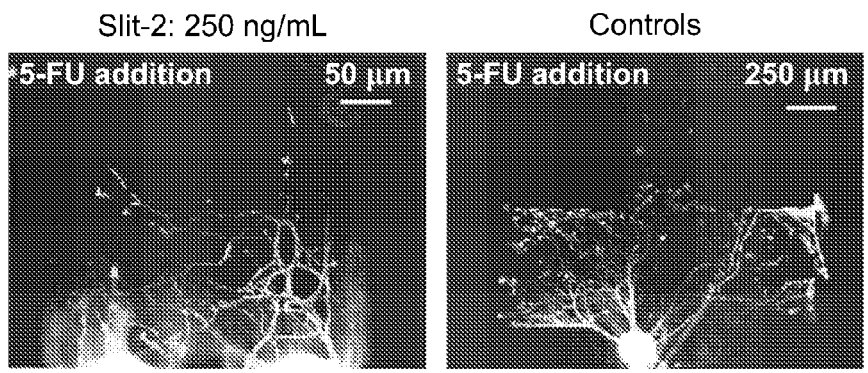
Figure 13C:
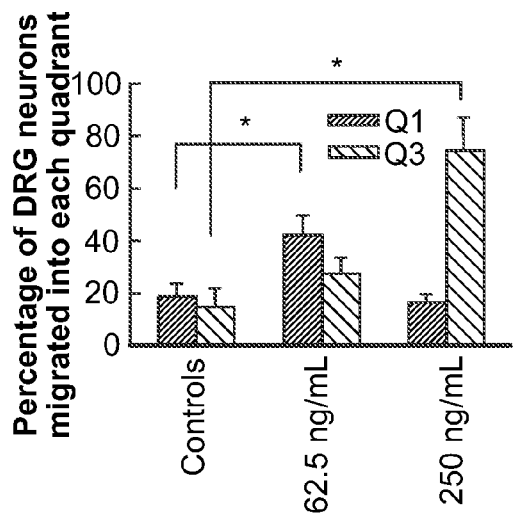
Figure 13D:
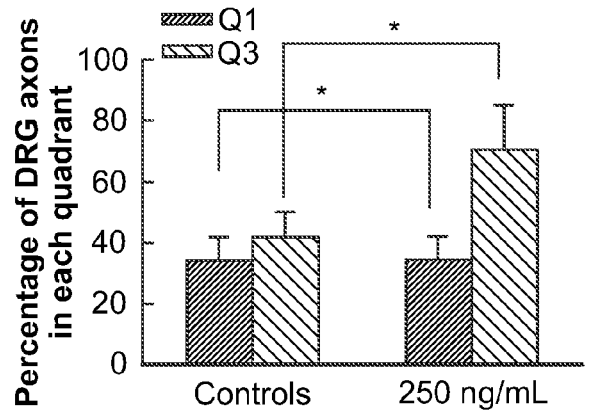

In order to inhibit DRG cell growth and migration and allow only neurite extension into the collagen scaffold, we added 5-fluorourasil (5-FU, $10^{-5}$ M concentration, Sigma Aldrich, USA), a pyrimidine analog drug used extensively in cancer research for inhibiting cell migration and proliferation (J. Fried, et al., Cancer. Res., 1981, 41, 2627). In these experiments, the DRG explants were seeded in the cell channel along with 5-FU on day 0, and after 24 h culture, all the channels were washed extensively with fresh media to remove traces of 5-FU from the gel. Since no cell migration into the scaffold was observed at this stage, a gradient was established in the devices by adding 250 ng/mL of slit-2 to the right hand channel. Representative fluorescence images show extensive DRG neuron axonal outgrowth and turning in 3D collagen scaffolds (FIG. 13B), cultured in the presence (or absence) of 250 ng/mL slit-2. Quantitative analysis revealed that 70±14.2% of DRG axons were repelled by slit-2, compared to 42±8% axons in control cultures (p<0.03 vs. controls). DRG neuron axonal turning into Q1 was significantly inhibited (by 56%) on slit-2 addition, relative to that in control cultures (p<0.05 vs. controls). These results were in broad agreement with the effects of 250 ng/mL slit-2 on hippocampal axonal turning in this device (FIGS. 12A-12C).

In addition to its potential in neurobiology studies, this device is useful in tissue engineering and regenerative medicine applications. Numerous studies have reported that an injury to the central nervous system (CNS) could drastically alter the cellular gene expression of guidance cues and their receptors (C. A. Willson, et al., Cell. Transplant., 2002, 11, 229). Of particular interest, changes in expression of netrin-1 and its receptors have been identified following an injury to the spinal cord and cerebellum, possibly accounting for regenerative failure of severed axons in these regions (R. Wehrle, et al., Eur. J. Neurosci., 2005, 22, 2134). The manipulation of these developmental cues, organization of their complex spatio-temporal gradients, understanding of cell-cell and cell-matrix interactions, and elucidation of the role of multiple guidance factors for the repair of injured CNS in animal experimental models could be a daunting and expensive task. Under these circumstances, it would be advantageous to recreate the cellular microenvironment in a simple inexpensive microfluidic system in vitro, and understand the role of each component (ECM molecules, growth factor gradients, mechanical stimuli, inflammatory environment, etc), as a guide to the design of tissue engineering approaches (e.g., peripheral nerve grafts, injectable hydrogels) for effective axonal regeneration and guidance in vivo.

Conclusions

This embodiment of the microfluidic device was designed, developed and optimized to study axonal guidance under chemo-gradients. The main advantages of this system include simplicity in fabrication and usage, cell culture in a physiological 3D environment, and maintenance of a stable gradient for long duration. Future experiments are underway to maintain constant gradients for even longer times, by continuous flow of media and chemo-attractants though the channels using external pumps. In this study, only known guidance cues such as netrin-1, brain pulp and slit-2 were studied for their influence on hippocampal or DRG axonal turning and DRG neuronal migration in vitro. These devices could also be used to screen new guidance molecules, study growth cone morphology, or identify genes involved in axon guidance. Since few methods exist for exposing cells to known gradients in vitro, this system could also be used with other cell types to study chemotaxis. Finally, this microfluidic platform has applications in optimization of biomaterials for neural tissue engineering, studying cancer cell migration, stem cell differentiation into highly specialized neurons, and angiogenesis.

Example 3

Interstitial Flow Influences Direction of Tumor Cell Migration Through Competing Mechanisms Interstitial flow is the convective transport of fluid through tissue extracellular matrix. This creeping fluid flow has been shown to affect the morphology and migration of cells such as fibroblasts, cancer cells, endothelial cells, and mesenchymal stem cells. However, due to limitations in experimental procedures and apparatuses, the mechanism by which cells detect flow and the details and dynamics of the cellular response remain largely unknown. A microfluidic cell culture system was designed to apply stable pressure gradients and fluid flow, and allow direct visualization of transient responses of cells seeded in a 3D collagen type I scaffold. This system was employed to examine the effects of interstitial flow on cancer cell morphology and migration and to extend previous studies showing that interstitial flow increases the metastatic potential of MDA-MB 231 breast cancer cells (Shields et al. 2007. Cancer Cell. 11:526-38). Consistent with this previous study, it was found that cells migrated along streamlines in the presence of flow; however, it was further demonstrated that the strength of the flow field as well as the cell density determined directional bias of migration along the streamline. In particular, it was found that cells either at high seeding density or with the CCR-7 receptor inhibited migrate against, rather than with the flow. Provided herein is further evidence that CCR7-dependent autologous chemotaxis is the mechanism that leads to migration with the flow, but also demonstrate a competing CCR7-independent mechanism that causes migration against the flow. Data from experiments investigating the effects of cell concentration, interstitial flow rate, and receptor activity support the hypothesis herein that the competing stimulus is shear stress mediated. This mechanism likely plays an important role in development of metastatic disease.

Tissues are comprised of cells residing in an extracellular matrix (ECM) containing interstitial fluid that transports nutrients and signaling molecules (Swartz, M A and Fleury, M E. 2007. Annu Rev. Biomed. Eng. 9:229-56; Jain, R. K. 1987. Cancer Research. 47:3039-3051). Osmotic and hydrostatic pressure gradients across tissues resulting from physiologic processes such as drainage toward lymphatics, inflammation, locally-elevated pressures due to tumor growth or leaky microvessels, and muscle contraction each drive fluid flow through the ECM (Jain, R. K. 1987. Cancer Research. 47:3039-3051; Boardman, K. C. and Swartz, M. A. 2003. Circ. Res. 92:801-808). This is termed interstitial flow and has long been recognized to be instrumental in tissue transport and physiology (Swartz, M A and Fleury, M E. 2007. Annu Rev. Biomed. Eng. 9:229-56; Levick, J R. 1987. Q. J. Exp. Phys. 72:409-37). Chary and Jain used fluorescence recovery after photobleaching to directly observe fluid flow in the tissue interstitium and determined typical flow velocities to be on the order of 0.1-2.0 µm/s, and more recent studies have demonstrated that flow can reach velocities as high as 4.0 µm/s (Chary, S R and Jain, R K. 1989. Proc. Natl. Acad. Sci. 86:5385-89; Dafni, H, et al., 2002. Cancer Research. 62:6731-6739).

Interstitial flow is particularly important in driving transport in the vicinity of tumors, as neoplastic tissue is often characterized by localized increases in interstitial pressure, leading to high interstitial pressure gradients at the tumor margin (Heldin, C, et al., 2004. Nat. Rev. Cancer. 4:806-13). Furthermore high intratumoral interstitial pressure has been correlated with poor prognosis for cancer patients (Curti, B. D. et al. 1993. Cancer Res. 53:2204-2207 (1993)). Interstitial flow has hence emerged as a possible stimulus for guiding tumor cell migration in the formation of metastases (Curti, B. D. et al. 1993. Cancer Res. 53:2204-2207 (1993); Chang, S., et al., 2008. Proc. Nat. Acad. Sci. 105:3927-2932; Hofmann, M., et al. 2006. Neoplasia. 8:89-95; Leunig, M., et al. 1992. Cancer Research. 52:6553-6560).

Shields et al. observed increased metastatic potential in cell populations exposed to flow and demonstrated that this was activated through binding of self-secreted CCL21 ligand to the CCR7 receptor (Shields et al. 2007. Cancer Cell. 11:526-38). This autocrine signaling mechanism, termed autologous chemotaxis, arises in a flow field where convection distributes autocrine chemokine factors creating a transcellular chemokine gradient, which in turn provides a chemotactic signal (Fleury, M E, et al., 2006. Biophysical Journal. 91:113-21).

The transwell assay used by Shields et al. to develop the autologous chemotaxis model and other similar in vitro assays have provided valuable insight into the metastatic process and tumor cell migration by allowing the systematic study of isolated stimuli on tumor cells (Curti, B. D. et al. 1993. Cancer Res. 53:2204-2207 (1993); Chang, S., et al., 2008. Proc. Nat. Acad. Sci. 105:3927-2932; Griffith, L G, and Swartz, M A. 2006. Nat. Rev. MCB. 7:211-24; Vickerman, V, et al., 2008. Lab on a Chip. 8:1468-77; Keenan, T. M. and Folch, A. 2007. Lab on a Chip. 8:34-57; Keenan, T. M. 2006. App. Phys. Letters. 89:114103-1-114103-3; Jeon, N. L., et al., 2000. Langmuir. 16:8311-8316; Friedl, P. et al. 1995. Cancer Research. 55:4557-4560; Helm, C., et al. 2005. Proc. Nat. Acad. Sci. 44:15779-15784; Wang, S and Tarbell, J M. 2000. Arterioscler. Thromb. Vasc. Biol. 20:2220-2225; Ng, C P and Swartz, M A. 2003. Am. J. Phiol. Heart Circ. Physiol. 284:H1771-H1777). However, limitations in the culture conditions and imaging capabilities of the transwell assay have contributed to our lack of detailed understanding of how cells detect and respond to interstitial flow. Further verification of the autologous chemotaxis model and investigation of other flow-induced cell stimuli would clearly benefit from a cell culture system in which cells are seeded in a physiologically relevant 3D matrix and in which the time-dependent morphological and migratory responses to flow can be quantified. 3D culture systems have been used to demonstrate the effect of interstitial flow on other cell types, such as fibroblasts (Ng, C P and Swartz, M A. 2003. Am. J. Phiol. Heart Circ. Physiol. 284:H1771-H1777; Boardman, K. C. and Swartz, M. A. 2003. Circ. Res. 92:801-808), myofibroblasts (Ng, C. P. et al., 2005. *J. Cell Science.* 118:4731-4740), endothelial cells (Vickerman, V, et al., 2008. Lab on a Chip. 8:1468-77; Helm, C., et al. 2005. Proc. Nat. Acad. Sci. 44:15779-15784), and smooth muscle cells (Wang, S and Tarbell, J M. 2000. Arterioscler. Thromb. Vasc. Biol. 20:2220-2225).

Described herein is a microfluidic cell culture system in which the directional bias and dynamics of cell migration in a physiologically relevant 3D matrix can be observed and quantified, and this system was employed to investigate the effects of interstitial flow on tumor cell migration. Demonstrated herein is that interstitial flow influences the directional bias of cell migration and that the migratory response is flow rate and cell density dependent. Furthermore, by blocking the CCR7 pathway, evidence to support the CCR7-dependent autologous chemotaxis model for migration in the direction of flow is provided, and that a second, CCR7-independent pathway stimulates cells to migrate against the flow is demonstrated. Competition between these two apparently independent mechanisms largely determines the direction of cell migration under the influence of interstitial flow.

Results

Figure 16A:
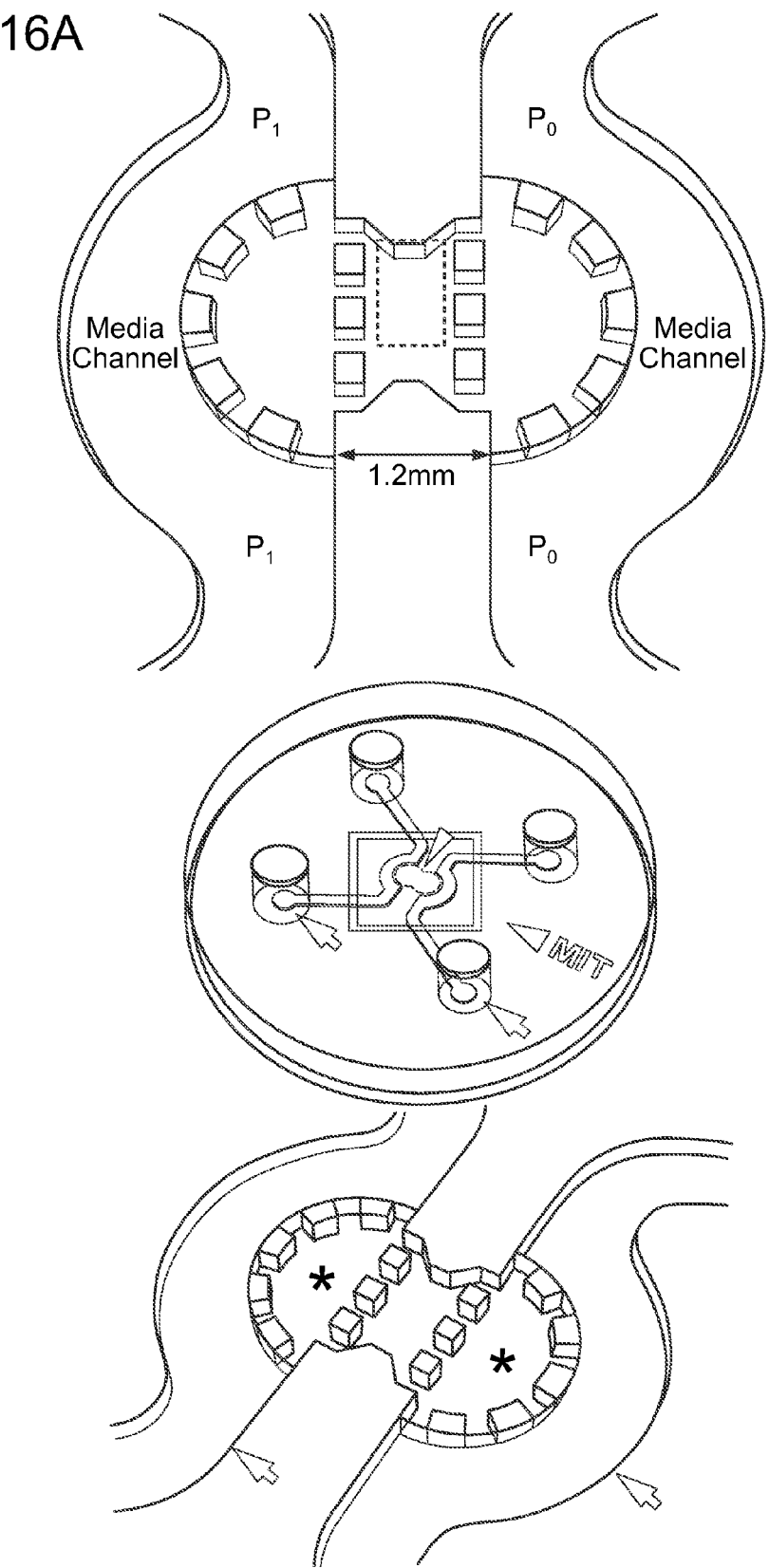
FIGS. 16A-16D: Microfluidic cell culture system for investigating the effects of interstitial flow on tumor cell migration. (16A) Schematic of the microfluidic device. The device consists of two channels (blue and green) separated by a region in which cells are suspended in collagen I gel (pink). By applying a pressure gradient across the gel, a consistent flow field is generated. To validate the flow field, fluorescent microspheres were introduced into the bulk media, and time lapse images were taken to track the beads. The microfluidic device provides cells access to growth medium and target tissue. Schematic of the device showing media channels (arrows), tissue wells (asterisks), and soma well (arrowhead). Detail of (a) showing media channels (arrows), tissue wells (asterisks), and soma well (arrowhead). (16B) Velocity vectors observed by tracking the fluorescent microspheres (green) superimposed on streamline vectors for a computation model (blue) and on a phase contrast image of the region of the device indicated by the dashed line in (16A). Experimentally observed velocity vectors are similar to the velocity vectors predicted by FEM model in (16C) magnitude and (16D) direction (mean±SEM, ** $p<0.01$ between flow velocities. Average angle computed between 0 and 90°)
Figure 16B:
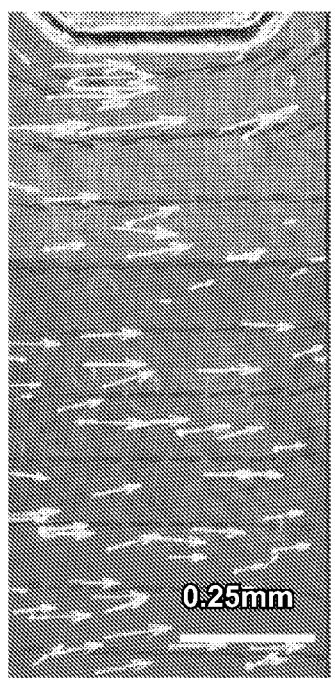
Figure 16C:
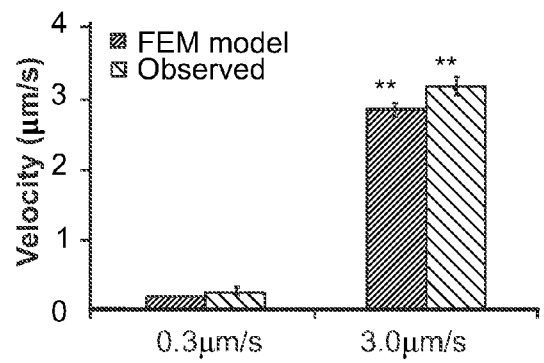
Figure 16D:
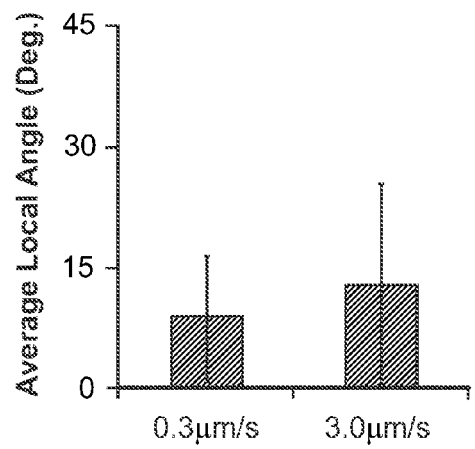

Cell culture system design and verification of interstitial flow field. A microfluidic cell culture system to culture breast cancer cells (MDA-MB 231) in a 3D collagen I matrix and to subject these cells to a controlled level of interstitial flow was employed. The system consists of two channels separated by a region containing single cells suspended in collagen I gel (FIG. 16A). By applying a hydrostatic pressure gradient across the gel region, a consistent flow field is generated. FEM software was used to solve Brinkman's equation for flow through porous medium for our system geometry (FIG. 16B). The flow field was validated by adding fluorescent microspheres to the bulk fluid, and imaging the microspheres using fluorescent time-lapse microscopy (FIG. 16B). Interstitial flow velocities were found to be repeatable and consistent with numerical predictions (FIG. 16C); the measured and predicted velocity vectors were also observed to be co-directional (FIG. 16D). In what follows, each flow field will be referred to by its respective nominal value, the rounded means of 0.3 μm/s and 3.0 μm/s, respectively, which are representative of the range of published in vivo interstitial flow velocity values. From the bead tracking data, the hydraulic permeability of 2 mg/ml collagen I gel was determined to be $1.55 \times 10^{-13}$ m2, similar to previously published values.

Figure 17A:
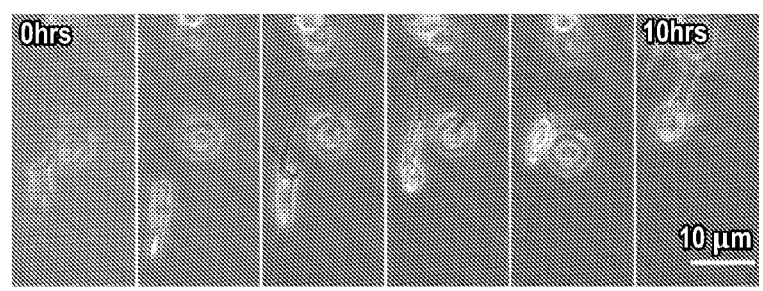
FIGS. 17A-17E: Interstitial flow influences direction of cell migration. (17A) Sample time lapse images of a cell migrating in interstitial flow field. Flow is 3.0 µm/s from top to bottom in the image. (17B) Sample data from one control device. Polar histogram demonstrates distribution of angles of net migration vectors for cells in a population in one device. Cells in control devices without flow randomly migrate. (17C) Flow changes the distribution of migration vector angles. In this sample data from one device, cell migration bias is against the flow. To quantify directional bias in cell migration, two metrics were computed. (17D) The streamline migration metric is a measure of migration bias along the streamlines, and (17E) the directional migration metric is a measure of the upstream or downstream migration bias for cells migrating along streamlines.
Figure 17B:
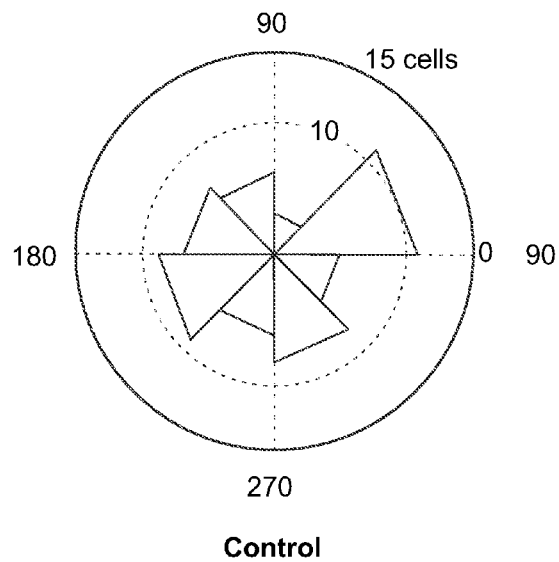
Figure 17C:
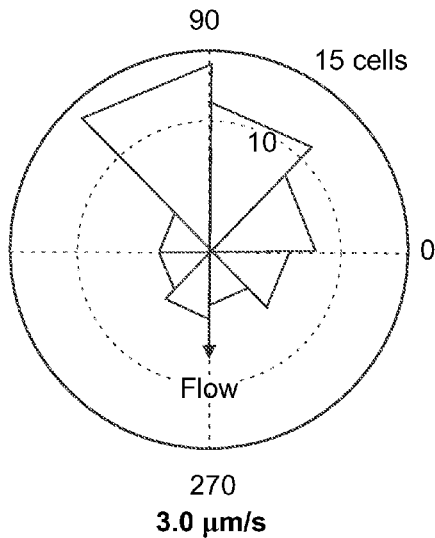

Cells preferentially align with the flow. MDA-MB 231 human breast carcinoma cells were seeded in collagen I gel in microfluidic devices. The cells were suspended in 3D within the gel and migrated in 3D (FIG. 17A). Confocal reflectance microscopy demonstrated that the cells degraded the collagen matrix as they migrated, leaving tracks in the gel during migration, thus suggesting a proteolytically active migration mechanism. When exposed to interstitial flow, cells aligned parallel to flow streamlines. At longer times, cells extended protrusions and subsequently formed multi-cell strings in parallel with the flow streamlines; after 40 hrs, cells exposed to flow velocities of 3.0 μm/s aligned with the streamlines of the flow field with 86±7% of cells aligned within 45° of the local streamline. Cells not exposed to flow remained randomly oriented with only 55±2% of cells within 45° of the local streamline.

Cells seeded at high concentration migrate against the flow. Using time-lapse imaging over 16 hr intervals, the center of mass of each cell was tracked. Cell migration speed was found to be independent of interstitial flow magnitude (0.10 μm/s±0.05). Cells exposed to interstitial flow migrated with increased directionality, defined as the net migration distance normalized by the total migration distance (0.63±0.073 for 0.3 μm/s, 0.61±0.071 for 3.0 μm/s, compared to 0.39±0.071 for control); however, cell motility, defined as the percentage of cells migrating a distance greater than one cell diameter in 8 hrs, was unaffected by flow.

Figure 17D:
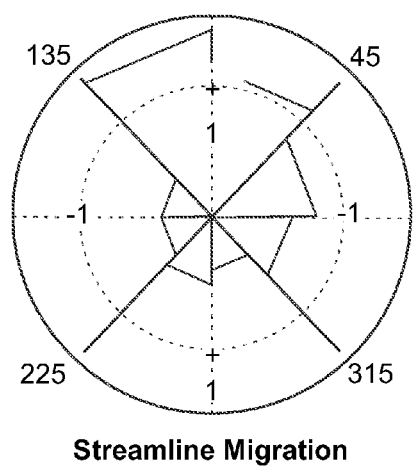
Figure 17E:
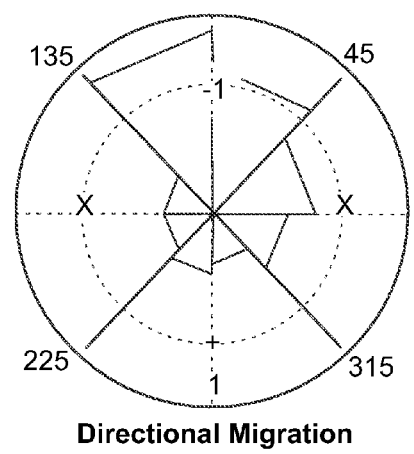

Interstitial flow induced a directional bias in cellular migration. Polar histograms of migration data for a control device and a device with 3.0 μm/s flow clearly demonstrate the effect of flow on the direction of migration vectors (FIGS. 17A-17E). In devices with flow, cells preferentially migrated along streamlines. To quantify the migration direction of cell populations, two metrics are presented. The "streamline migration metric" scores cells with a +1 if they migrate within 45° of a streamline and a −1 if they migrate outside of this zone (FIG. 17D). An average score for a cell population of +1 indicates that all of the cells are migrating along a streamline, a score of 0 corresponds to purely random migration, and score of −1 indicates that all cells are migrating perpendicular to the streamline. To determine directional bias of migration along streamlines, a "directional migration metric" was computed that scored cells with a +1 if they migrated in the direction of flow and a −1 if they migrated against the flow (FIG. 17E). A population has an average score of +1 if all of the cells migrating within 45° of a streamline are migrating with the flow, a score of 0 if cells are randomly migrating, and score of −1 if all of the cells are migrating against the flow.

Figure 18A:
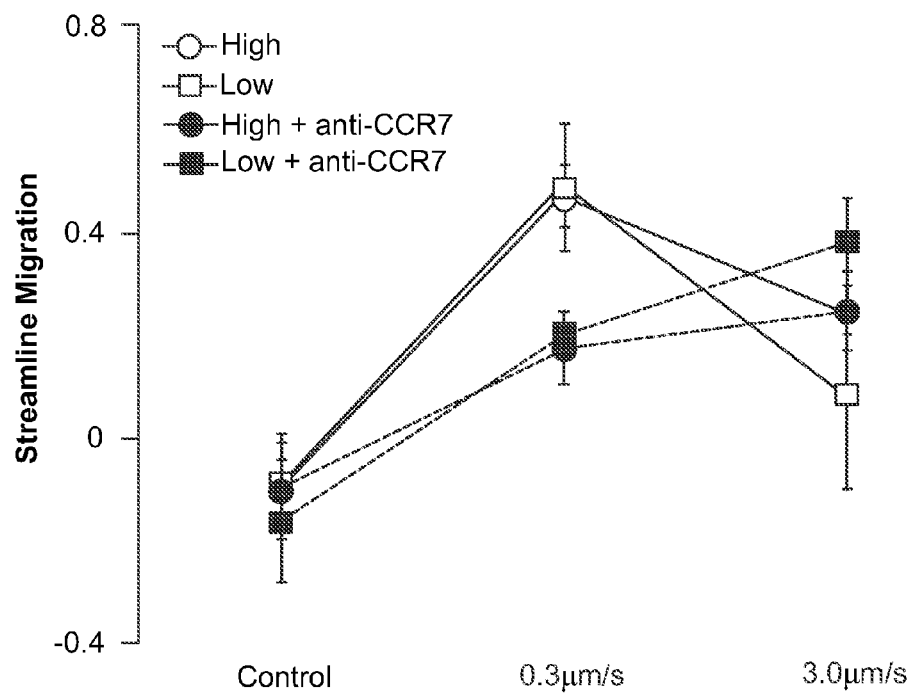
FIGS. 18A-18B: Interstital flow induces a bias in direction of tumor cell migration. Cells were scored according to the metrics presented in FIGS. 17A-17E. "High" and "low" refer to $25 \times 10^4$ cells/ml and $5 \times 10^4$ cells/ml, respectively. (18A) Cells exposed to interstitial flow preferentially migrated along streamlines, and this bias is a function of flow rate, cell density, and CCR7 receptor activity. Blocking CCR7 in a 0.3 µm/s flow field causes a significant decrease in streamline migration score ($p<0.01$). In a 3.0 µm/s flow field, blocking CCR7 has the opposite effect of increasing streamline migration score, but only at a low cell density ($p<0.05$). (18B) Cells exposed to interstitial flow preferentially migrated upstream or downstream as a function of flow rate, cell density, and CCR7 receptor activity. Directional migration scores become more negative with increasing flow velocity. With active CCR7, increasing cell density reverses directional bias from downstream to upstream ($p<0.01$ for both flow rates), but when CCR7 is blocked, directional migration scores are more negative and do not depend on cell density. (Mean±STD computed by averaging score for each cell in one device ($n>15$) and averaging the score for 3 devices at each condition).
Figure 18B:
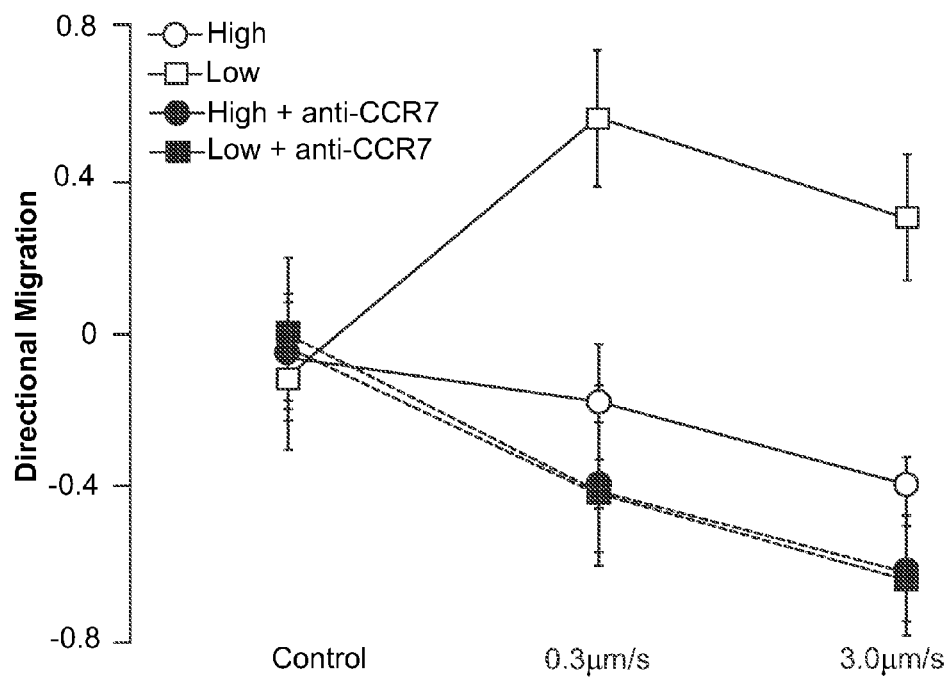

Cells seeded at $25 \times 10^4$ cells/ml and exposed to interstitial flow preferentially migrated along the flow streamlines, with average streamline migration scores of 0.47±0.06 for 0.3 μm/s and 0.24±0.04 for 3.0 μm/s (mean±STD, FIG. 18A). Of the cells migrating along the streamline, a greater fraction of the cell population migrated upstream than downstream and the strength of this upstream bias was a function of interstitial flow rate. At an interstitial flow speed of 0.3 μm/s, the average directional migration score was −0.18±0.15, and at 3.0 μm/s directional bias increased further to −0.40±0.08. Cells in control devices did not preferentially migrate in either direction (FIG. 18B). These results were opposite to those reported by Shields et al. who had observed cells to preferentially migrate with the flow.

At low cell seeding density, cells migrate with the flow. In order to test for the effect of cell density on directional migration under flow, experiments were conducted at two different seeding densities, $25 \times 10^4$ and $5 \times 10^4$ cells/ml. This difference in density corresponds to an increase in intercellular distance by a factor of approximately 2. Increasing intercellular distance did not affect the bias for migration along streamlines in a 0.3 μm/s interstitial flow field, although a smaller percentage of cells migrated along streamlines in a 3.0 μm/s interstitial field when seeded at a lower concentration (FIG. 18A).

Decreasing cell density did, however, exert a dramatic effect on the direction of migration, causing a reversal in the directional bias of migration relative to the flow as indicated by the sign change in the directional migration metric, a result consistent with Shields et al. At a flow speed of 0.3 μm/s, the average directional migration score was −0.177±0.15 at $25 \times 10^4$ cells/ml but increased to 0.570±0.18 at $5 \times 10^4$ cells/ml. For 3.0 μm/s, the average directional migration score was −0.401±0.08 at $25 \times 10^4$ cells/ml but increased to 0.307±0.16 at $5 \times 10^4$ cells/ml (FIG. 18B).

Blocking CCR7 signaling increases the tendency for upstream migration. In devices seeded at $25 \times 10^4$ cells/ml and subject to 0.3 μm/s interstitial flow, addition of CCR7 reduced the bias of migration along streamlines, lowering the average streamline migration metric from 0.472±0.060 to 0.174±0.070, but had little effect on cells in a 3.0 μm/s flow field (FIG. 18A). At both interstitial flow velocities, blocking CCR7 increased directional migration against the flow (FIG. 18B).

Cells at low seeding density migrate upstream when CCR7 signaling is blocked. Interestingly, the combined effect of decreasing cell density and blocking CCR7 resulted in a flow-rate dependent change in migration bias along streamlines. At 0.3 μm/s, the streamline migration score was reduced from 0.489±0.122 to 0.201±0.031 with the addition of CCR7 blocking antibody at $5\times10^4$ cells/ml; however, at 3.0 μm/s, the streamline migration score increased from 0.088±0.188 to 0.384±0.06 at $5\times10^4$ cells/ml (FIG. 18A).

In devices seeded at $5\times10^4$ cells/ml, addition of anti-CCR7 blocking antibody completely negated preferential migration in the direction of flow and in fact, caused preferential migration against the flow. The average directional migration score dramatically decreased at both flow velocities, from 0.570±0.12 to −0.420±0.19 at 0.3 μm/s and from 0.307±0.16 to −0.649±0.18 at 3.0 μm/s (FIG. 18B).

Blocking CCR7 eliminates seeding density dependence of cell migration. When comparing cell populations at $5\times10^4$ cells/ml with CCR7 blocking antibody and populations at $25\times10^4$ cells/ml with CCR7 blocking antibody, there are no significant differences in directional migration bias. These data suggest that addition of the blocking antibody negates the effect of cell concentration on directional migration bias. Furthermore, although the effects are not statistically significant, a consistent trend is observed in the effect of flow rate. At both cell concentrations, increasing the flow rate from 0.3 μm/s to 3.0 μm/s increases the percentage of cells migrating along the streamline and increases the upstream migration bias of cells migrating along the streamline (FIGS. 18A-18B).

Discussion

Effect of interstitial flow on cell migration. Interstitial flow influenced tumor cell migration and, in particular, dramatically affected the direction of migration. For all culture conditions with interstitial flow, cells preferentially migrated along streamlines. The relative fraction of the cell population that migrated along the streamlines, and the upstream and downstream bias along the streamline was a function of cell density, CCR7 activity, and interstitial flow velocity.

CCR7 and autologous chemotaxis. For cells seeded at $5\times10^4$ and $25\times10^4$ cells/ml in 3.0 μm/s and 0.3 μm/s flow fields, addition of CCR7 blocking antibody decreased the tendency for downstream migration. These data indicate that the CCR7 receptor is involved in downstream migration and thus support the findings of Shields et al., who identified the CCR7 chemokine receptor as critical in the signaling pathway responsible for autologous chemotaxis (Shields et al. 2007. Cancer Cell. 11:526-38). Autologous chemotaxis is the result of a flow-induced gradient of an autocrine chemotactic signal that is detected by the CCR7 chemokine receptor and stimulates migration in the direction of flow. Provided herein is data confirming that CCR7 is involved in tumor cell migration, and validating the autologous chemotaxis model by demonstrating that CCR7 is directly involved in downstream migration.

Interestingly, in experiments without the CCR7 blocking antibody, migration direction was a strong function of cell seeding density. As cell concentration was increased, fewer cells migrated downstream, and a general tendency for migration in the upstream direction began to emerge. It was expected that the density dependence in the direction of cell migration is the result of the interaction between autocrine and paracrine chemokine concentration fields. Autologous chemotaxis, as the result of autocrine chemokine gradients, had previously been studied in the context of single cells (Fleury, M E, et al., 2006. Biophysical Journal. 91:113-21), but when the effects of neighboring cells in the model was included, increasing cell density was observed to decrease the magnitude of the transcellular gradient for cells downstream of other cells. This is due to the fact that the local effects of a single cell become overwhelmed by the effects of ligand release from a population of cells. Consequently, increasing the cell density decreases the autocrine transcellular gradient, attenuating the signal for autologous chemotaxis, and reducing the tendency for CCR7-mediated migration downstream. As further validation that high cell concentration results in a weaker autologous chemotaxis stimulus, the directional migration trends are similar between cell populations seeded at high cell concentration and cell populations with blocked CCR7.

Competing signals. When CCR7 is blocked, directional migration scores decrease for all conditions tested. The decrease in streamline migration scores is pronounced for cells at $5\times10^4$ cells/ml; the average directional migration score changes sign from positive to negative, reflecting a shift in migration bias from downstream to upstream. Motivated by the negative directional migration scores for both cell densities and flow rates when CCR7 is blocked, it was hypothesized that a CCR7-independent stimulus competes with CCR7-dependent autologous chemotaxis and when CCR7 is inhibited, stimulates cells to migrate upstream. The relative strength of these two stimuli governs the directional bias in migration for a cell population and is a function of cell density, interstitial flow rate, and CCR7 receptor availability.

The streamline and directional migration scores provide insight into the nature of the CCR7 independent stimulus. Directional migration scores monotonically decrease (become more negative) with increasing interstitial flow velocity, and this effect is independent of CCR7 activity and seeding density. In contrast, downstream migration of cells at low density peaks at a flow rate of 0.3 um/s, then decreases at 3.0 um/s. These data suggest that the CCR7 independent stimulus increases in strength with increasing interstitial flow velocity. Furthermore, when CCR7 is blocked, the directional migration score is independent of cell seeding density, suggesting that the strength of the CCR7 independent stimulus is cell density independent. Interestingly, the upstream migration stimulus persists even at low cell density and flow rate suggesting that the stimulus is independent of cell-cell interactions.

The stimulus that drives cells upstream is flow rate dependent but cell density independent. Flow-induced stresses on a cell are a function of flow rate and, in contrast to an autocrine or paracrine signaling stimulus, independent of cell density. Shear stress has long been known to play a role in endothelial cell (EC) migration (Branemark, P. I. 1965. Bibl. Anat. 7:9-28; Li, S., Huang, N. F. and Hsu, S. 2005. J. of Cellular Biochem. 96:1110-1126; Boardman, K. C. and Swartz, M. A. 2003. Circ. Res. 92:801-808; Branemark, P. I. 1965. Bibl. Anat. 7:9-28; Moldovan, N. I, et al., 2000. Circ. Res. 87:378-384; Galbraith, C. G., et al., 1998. Cell. Motil. Cytoskeleton. 40:317-330; Helmke, B. P., et al., 2000. Circ. Res. 86:745-752; Wang, N., et al., 1993. Science. 260:1124-1127), and Wang and Tarbell demonstrated that small interstitial flow velocities could impart large shear stresses on a cell due to the small interstitial spaces in tissues (Wang, D. M. and Tarbell, J. M. 1995. J. Biomech. Eng. 117:358-363). Using Ganaphthy's formulation for drag on a sphere in a Brinkman's medium, it was estimated the total stress on a cell of radius 10

μm in a porous medium of permeability 1.5×10-6 m2 to be 0.1 Pa for 3.0 μm/s and 0.01 Pa for 0.3 μm/s (Ganaphthy, R. 1997. *Zeitschrift für Angewandte Mathematik and Mechanik.* 77:871-875). Lawler et al. demonstrated that shear stresses of this magnitude influence tumor cell morphology and found that dynamic bleb formation in esophageal cancer cells, which is associated with migration through a 3D matrix, increases with increasing shear rate for shear stresses greater than 0.05 Pa (Lawler, K., et al., 2006. *Am. J. Physiol. Cell Physiol.* 291:668-677).

Flow past a cell in a 3D matrix leads to a transcellular shear stress gradient (Pedersen, J. A., et al., 2010). Cells in 3D matrices under interstitial flow: effects of extracellular matrix alignment on shear stress and drag forces. 43:900-905), and this stress results in asymmetric force in cell-matrix interactions—e.g., tensile force on the upstream side and compressive force on the downstream side. It has been shown that tensile force can activate integrins and drive focal adhesion assembly (Galbraith, C. G., et al., 2001. J. Cell Biology. 159:695-705; Kong, F., et al., 2009. J. Cell Biology. 185: 1275-1284) and that integrins mediate interstitial flow induced matrix remodeling by fibroblasts in 3D matrix (Ng, C. P. et al., 2005. *J. Cell Science.* 118:4731-4740). It was speculated that the flow-induced stress gradient leads to a difference in integrin and FA activation, with more activation upstream, where cell-matrix connections are in tension. It was expected that this mechanism is similar to that examined by Lo et al., who demonstrated that a transcellular strain gradient, which presumably results in biased integrin activation due to the gradient in tension on the integrins, guides cell migration toward increasing strain (Lo, C., et al., 2000. Biophysical J. 79:144-152).

Fleury et al. developed a computational model and showed that interstitial flow biases the distribution of secreted MMPs, resulting in MMP accumulation downstream of the cell (Fleury, M E, et al., 2006. Biophysical Journal. 91:113-21). The increased concentration of MMPs downstream would result in increased degradation of the matrix, further strengthening upstream cell-matrix connections and favoring upstream migration. Confocal reflectance data demonstrated that cells leave gaps in the matrix at the trailing edge as they migrate, supporting the hypothesis that directed proteolysis is involved in upstream migration. It was believed that directed proteolysis is one of many mechanisms, including FA structure, transcellular stress distribution, and morphogen distribution (Wang, S and Tarbell, J M. 2000. Arterioscler. Thromb. Vasc. Biol. 20:2220-2225; Cukierman, E. et al. *Science.* 294: 1708-1713), that differs significantly in 2D and 3D and contributes to differences in our data and that of Li et al., who demonstrated that shear stress caused polarized recruitment of focal adhesion kinase (FAK) at the downstream edge of the cell, formation of new focal adhesions, and subsequent migration in the direction of flow for ECs seeded on a 2D substrate (Li, S, et al., 2002. Proc. Natl. Acad. Sci. 99:3546-3551).

Elucidating the role of integrins in driving upstream migration is difficult as the migration pathways activated through integrins and chemokine receptors converge early in the signaling cascade (Li, S., Huang, N. F. and Hsu, S. 2005. J. of Cellular Biochem. 96:1110-1126; Lawler, K., et al., 2006. *Am. J. Physiol. Cell Physiol.* 291:668-677; Shyy, J., Y. and Chien, S. 2001. Circ. Res. 91:769-775; Frame, M. C. 2002. Biochimica et Biophysica Acta. 1602:114-130). FAK colocalizes with activated integrins and activates Src kinase (Thomas, J. W., et al., 1998. J. Biol. Chem. 273:577-583; Eide, B. L. et al., 1995. Mol. Cell. Biol. 15:2819-1817; Schaller, M. D., et al., 1994. Mol. Cell. Biol. 14:1680-1688), which modulates traction forces important for tumor cell migration (Fincham, V. J. and Frame, M. C. 1998. EMBO J. 17:81-92; Sieg, D. J. et al., 1998. EMBO J. 17:5933-5947). As described herein, a specific inhibitor of Src kinase PP2 (Li, S., et al., 1997. J. Biol. Chem. 272:30455-30462; Jalali, S., et al., 1998. Arterioscler. Thromb. Vasc. Biol. 18:227-234) and it was found that cells migrated randomly, with no biased migration upstream or downstream. These data are consistent with the CCR7-mediated autologous chemotaxis model for downstream migration since Src has been implicated in the CCR7 pathway in lymphocytes (Riol-Blanco, L., et al., 2005. J. Immunol. 174:4070-4080; Bardi, G., et al., 2003. FEBS Letters. 542:79-83). Since PP2 blocked upstream migration as well, Src is involved in upstream migration; furthermore, upstream migration is independent of cell density, so paracrine and autocrine signaling through chemokine receptors are unlikely stimuli for Src activation. Consequently, the PP2 data support the hypothesis herein that flow induced stress gradients and directed proteolysis lead to bias integrin activation, FA formation, and subsequent Src activation, stimulating migration against the flow.

Interstitial flow has been studied extensively with regard to drug transport for cancer treatment (Heldin, C, et al., 2004. Nat. Rev. Cancer. 4:806-13), and in vivo it has been shown that interstitial fluid pressure (IFP) is correlated with cervix cancer patient survival (Milosevic, M., et al., 2001. *Cancer Research.* 61:6400-6405) and reducing interstitial fluid pressure reduces tumor cell proliferation (Hofmann, M., et al. 2006. Neoplasia. 8:89-95). Because interstitial fluid flows from a tumor to surrounding lymphatics, blocking CCR7 and thus inhibiting migration in the flow direction would reduce migration from the tumor and likely reduce the probability of metastasis formation. Cell density and interstitial flow rates decrease with increasing distance from the cell, both of which are highest at the tumor margin. The data herein indicate the existence of an "escape radius" at a critical distance from the tumor surface. For cells at a radial distance less than the escape radius, interstitial flow guides cells upstream, keeping cells clustered with the tumor, but for cells located beyond the escape radius, interstitial flow guides cells downstream, toward draining lymphatics. Although further modeling and in vivo data are required to validate its existence, the escape radius could be a critical parameter in estimating the severity of metastatic disease and determining proper treatment. Interstitial flow is just one of many biochemical and biophysical stimuli in vivo that influences tumor cell migration, but its consideration is crucial for understanding and treating metastatic disease and for developing tissue engineered constructs.

Materials and Methods

Cell and Device Preparation.

Microfluidic devices were fabricated using soft lithography in a process that has been described previously (Vickerman, V, et al., 2008. Lab on a Chip. 8:1468-77; Kothapalli unpublished data). Polydimethylsiloxane (PDMS, Ellsworth Adhesives, MA) was mixed at 10:1 base:curing agent, poured over a silicon master, and incubated overnight at 80° C. The PDMS was cut from the silicon master, trimmed, and autoclaved in water. The devices were then dry autoclaved and dried overnight in an oven at 80° C. The sterile PDMS devices were then surface activated by plasma treatment for 2 min, (Harrick Plasma, Ithaca, N.Y.), coated with Poly-D-lysine (PDL, Sigma-Aldrich, St. Louis, Mo.) incubated overnight at 37° C., washed with sterile water, and dried overnight at 80° C.

MDA-MB-231 cells originally derived from a pleural effusion were obtained from the American Type Culture Collection (Manassas, Va.) and were cultured in standard growth media of 10×DMEM (Invitrogen, Carlsbad, Calif.) with 10% FBS (Invitrogen). Collagen type I (BD Biosciences, Bedford, Mass.) solution was buffered with 10×DMEM, titrated to a pH of 8.9 with NaOH, and brought to a final concentration of 2 mg/ml collagen I in total solution. Cells were harvested with 0.05% Trypsin/EDTA and centrifuged at 12000 RPM for 5 min. The cells were resuspended in media at the desired concentration, and the suspended cells were then mixed with collagen I solution to make a final cell density of $2.5×10^5$ or $0.5×10^5$ cells/(ml total solution). The gel-cell solution was added to the devices by hand using a micropipette, and devices were sealed with a coverslip. The seeded devices were placed in an incubator at 37° C. for 30 min to allow the collagen gel to polymerize before adding media.

Cells were incubated overnight at 37° C. To apply a pressure gradient, external media reservoirs were connected to the microfluidic chip. The reservoirs were made from modified Nalgene (Thermo Fisher Scientific, Waltham, Mass.) bottles with Tygon (Compagnie de Saint-Gobain, Paris, France) tubing to connect the reservoirs to the device. Medium was added to each reservoir at volumes that established the desired pressure gradient across the gel. Devices were allowed to reach thermal equilibrium at 37° C. before imaging (see Supplementary Methods in SI Appendix for details on imaging and data quantification).

Media was supplemented with human recombinant EGF at 10 ng/ml (PeproTech, Rocky Hill, N.J.). For CCR7 blocking, human CCR7 MAb (R&D Systems) was added to the media at 5 µg/ml.

Example 4

Three-Dimensional Microfluidic System for Screening Antimetastatic Lung Cancer Drugs Matrix metalloproteinases (MMPs) inhibition are likely useful as an effective strategy to treat lung cancer. The lack of selective MMP inhibitors along with a limited knowledge about the exact functions of a particular MMP still hamper the clinical applications. Despite disappointments of clinical trials with the currently available MMP inhibitors, a third generation of MMP inhibitors is currently under investigation. They are especially designed to block only the target MMP, while sparing the anti-target ones. However, this absolutely emphasizes the need to understand the involvement and activity levels of MMPs and at the same time the requirement for the development of specific and sensitive quantitative assay to determine MMP activity during the metastasis of lung cancers.

For the purpose of developing the 3D microfluidic systems for screening antimetastatic lung cancer drugs, stabilizing mature microvascular networks for the long term was explored. Several research groups have reported the application of microfluidic devices to study important steps of cancer metastasis, focusing on individual steps in the metastatic sequential processes (Strell, C., et al., *Mol. Life Sci.*, 64:3306-3316 (2007); Chaw, K. C., et al., *Lab Chip*, 7:1041-1047 (2007); Liu, T., et 430:4285-4291 (2009)). However, none of these studies has led to an ability to study metastatic sequential processes. Described herein is a methodology for examining sequential processes of lung cancer metastasis within a 3D microfluidic platform. The approach is commercially applicable for screening anti-metastatic lung cancer drugs and also developing specific MMP inhibitors.

Figure 19B:
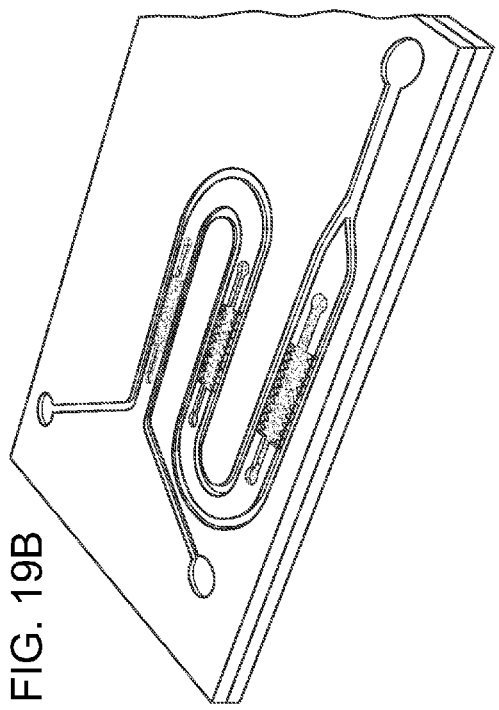
Figure 19D:
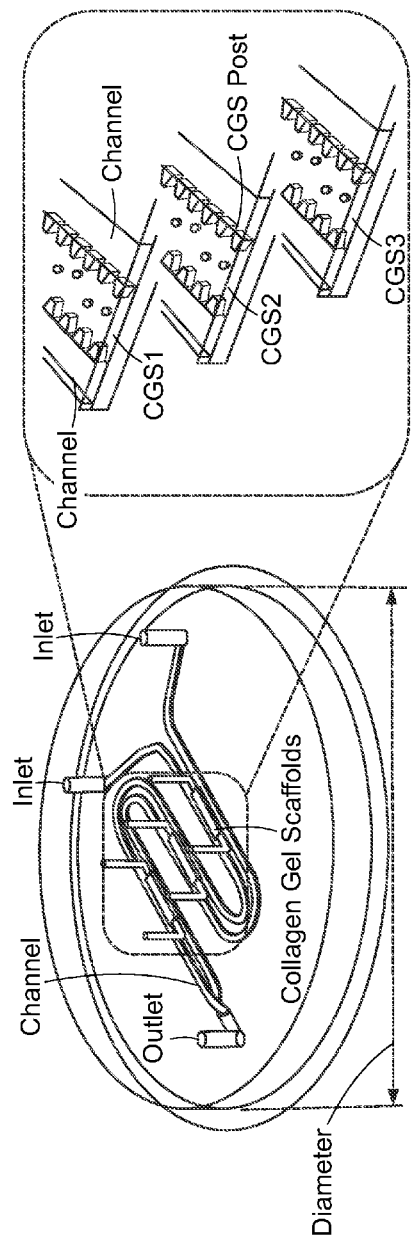

A perfusion microfluidic device which included three different collagen gel scaffolds (CGSs) (CGS1 (top), CGS2 (middle), and CGS3 (bottom)) along a serpentine channel was designed and fabricated using polydimethysiloxane (PDMS, Sylgard 184, Dow Chemical, MI) and soft lithography as previously described for standard microfluidic protocols (V. Vickerman, et al., Lab Chip, 2008, 8, 1468-1477; S. Chung, R. et al., Lab Chip, 2009, 9, 269-275). See FIGS. 19A-19D. The diameter of the device was about 350 mm and had two independent flow channels. The inlet dimensions of the flow channels was about 500 µm (w)×150 µm (h) and the dimensions of the three CGSs were about 4,100 µm (l)×1,300 µm (w)×150 µm (h). In this particular device, there were two independent flow channels that merged at the outlet (FIG. 19A), and the three CGSs were filled with three different concentrations of type-I collagen gel (BD Biosciences, MA, USA) via the gel ports. Each CGS contained 20 trapezoidal mechanical posts (FIG. 19B).

Vascular networks of human umbilical vein vascular cells (HUVECs) within the CGSs were created and stable mature vascular networks were formed within the 3D CGSs. Lung cancer cells (A549) were co-cultured on the channels with static conditions. Anti-metastatic lung cancer drugs such as GM6001 as broad-spectrum MMP inhibitor, specific inhibitors for MMP2 and MMP9 as anti-metastatic drug controls, and specific inhibitors for MMP7 and MMP13 as negative controls can then be applied to the device. The sequential processes of metastasis (e.g., migration, intravasation, extravasation) can be examined qualitatively and quantitatively, and can be performed without the use of chemotactic factors.

Results and Discussion
Maturation of Microvascular Networks within 3D CGSs

Figure 20A:
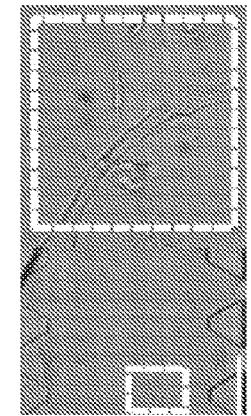
FIGS. 20A-20B: Microvascular networks stabilized within CGS2 (2.5 mg/ml) after 96 h. (20A-20B) phase contrast and confocal micro-scopic images showing maturated vascular networks marked in yellow dotted lines. Scale bars, 20A (300 µm); 20B (640 µm).
Figure 20B:
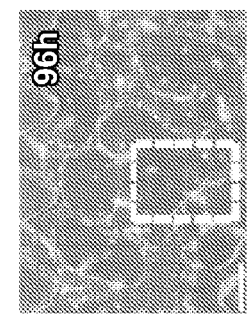
Figure 21A:
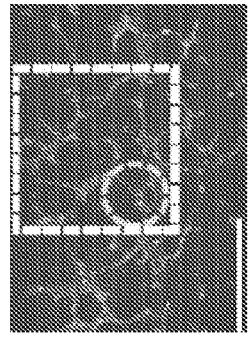
FIGS. 21A-21B: Lumen-like maturation in CGS2 (2.5 mg/ml) after 108 h. (21A-21B) phase contrast and confocal microscopic images showing maturated lumen-like forms marked in white dotted lines. Scale bars, 21A (300 µm); 21B (640 µm).
Figure 21B:
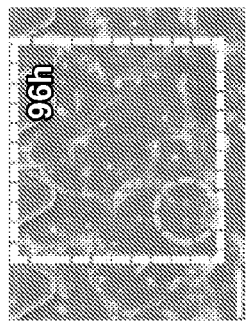
Figure 22A:
Figure 22B:
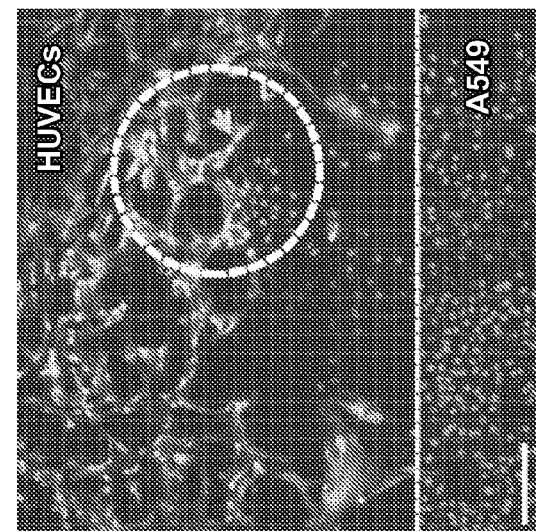
Figure 22C:
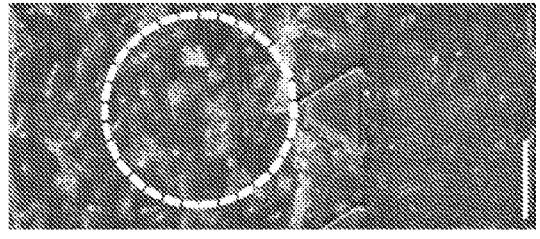

The formation of stable vascular networks of HUVECs depended on seeding density, concentration of VEGF and collagen concentration in CGSs. Stable vascular networks of HUVECs within 3D CGS at $3×10^6$ HUVECs/ml, 40 ng/ml of VEGF, and 2.0-2.5 mg/ml collagen were collected. FIGS. 20A-20B represents microvascular networks stabilized within CGS2 (2.5 mg/ml) after 96 h. VEGF (40 ng/ml) was applied for signalling pathways of vessel maturation and GM6001 (12.5 µM after 24 h) was applied for governing cell-matrix interaction of vessel stabilization. The lumen-like formation shown in FIGS. 21A-21B showed the application of 3D vascular network to the antimetastatic cancer drug screening.

Migration of Lung Cancer Cells into Microvascular Networks within CGSs

More preferable migration and intravasation steps were observed by coculturing with A549 at 96 h after the initial HUVEC seeding. FIGS. 22A-22D represented an example of the microfluidic cancer metastasis systems showing the sequential steps of migration and intravasation of A549 within 3D CGS (2.0 mg/ml).

Application of GM6001 as a MMP Inhibitor to Lung Cancer Cells

Migration of A549 lung cancer cells from channels to CGS2 was not shown with GM6001 (12.5 µM) at 18 h of coculturing after 96 h. In contrast, migration from the same cocultures without GM6001 was observed (FIGS. 23A-23D).

Sequential steps of migration and intravasation of A549 under static or temporal conditions without use of any chemotactic factors was observed. This microfluidic metastasis system can be used to screening antimetastatic cancer drugs to inhibit migration and/or intravasation. Also extravasation can be observed by spatiotemporally controlling various 3D micro-environments and to obtain more preferable quantitative data.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

The invention claimed is:

1. A microfluidic device comprising:
    a substrate comprised of an optically transparent material and further comprising
    i) one or more fluid channels;
    ii) one or more fluid channel inlets;
    iii) one or more fluid channel outlets;
    iv) one or more gel cage regions; and
    v) a plurality of posts;
    wherein
    all or a portion of each gel cage region is flanked by all or a portion of one or more fluid channels, thereby creating one or more gel cage region-fluid channel interface regions; and
    each gel cage region comprises at least one row of posts which forms the gel cage region, each post of the at least one row of posts forming a triangular shape, a trapezoidal shape or a combination thereof, the sum of a contact angle of a gel on a surface of the substrate and an internal angle of a corner of each post of the at least one row of posts being about 180°, and a distance between each neighboring pair of posts in the at least one row of posts being from about 50 micrometers to about 300 micrometers.

2. The device of claim 1 wherein each gel cage region forms a gel channel and each gel channel comprises two parallel rows of posts, in which each row of posts is along the length of each gel channel and one row is along one side of the gel channel, and the other row is along the opposite side of the gel channel thereby forming a gel cage region along each length of each gel channel.

3. The microfluidic device of claim 1 comprising a first fluid channel and a second fluid channel of the one or more fluid channels, wherein a first gel cage region of the one or more gel cage regions forms a gel channel, and
    v)
    wherein
    all or a portion of one side of the gel channel is flanked by, and parallel to, all or a portion of the first fluid channel thereby creating a first gel channel-fluid channel interface region;
    all or a portion of the other side of the gel channel is flanked by, and parallel to, all or a portion of the second fluid channel thereby creating a second gel channel-fluid channel interface region; and
    the gel channel comprises two parallel rows of posts of the at least one row of posts, in which each row of posts is along the length of the gel channel and one row is along one side of the gel channel at the first gel channel-fluid channel interface, and the other row is along the other side of the gel channel at the second gel channel-fluid channel interface, thereby forming the first gel cage region along the length of the gel channel.

4. A high throughput device comprising at least two of the devices of claim 1 linked together in series, in parallel or in a combination thereof.

5. The microfluidic device of claim 3 further comprising:
    (vii) a second gel cage region of the one or more gel cage regions which forms a second gel channel; and
    (viii) a third gel cage region of the one or more gel cage regions which forms a third gel channel
    wherein
    all or a portion of one side of the second gel channel is flanked by, and parallel to, all or a portion of the first fluid channel thereby creating a third gel channel-fluid channel interface region;
    all or a portion of the other side of the second gel channel, is flanked by, and parallel to, all or a portion of the second fluid channel thereby creating a fourth gel channel-fluid channel interface region;
    all or a portion of one side of the third gel channel is flanked by, and parallel to, all or a portion of the first fluid channel thereby creating a fifth gel channel-fluid channel interface region;
    all or a portion of the other side of the third gel channel, is flanked by, and parallel to, all or a portion of the second fluid channel thereby creating a sixth gel channel-fluid channel interface region;
    the second gel channel comprises two parallel rows of posts of the at least one row of posts, in which each row of posts is along the length of the second gel channel and one row is along one side of the second gel channel at the third gel channel-fluid channel interface, and the other row is along the other side of the second gel channel at the fourth gel channel-fluid channel interface, thereby forming the second gel cage region along the length of the second gel channel; and
    the third gel channel comprises two parallel rows of posts of the at least one row of posts, in which each row of posts is along the length of the third gel channel and one row is along one side of the third gel channel at the fifth gel channel-fluid channel interface, and the other row is along the other side of the third gel channel at the sixth gel channel-fluid channel interface, thereby forming the third gel cage region along the length of the third gel channel.

6. The device of claim 5 comprising
    at least three fluid channels,
    wherein the first gel cage region, the second gel cage region and the third gel cage region are arranged in parallel to one another in the device.

7. The device of claim 1 further comprising one or more gas channels wherein all or a portion of the one or more gas channels flanks at least one side of the one or more fluid channels, the one or more gel cage regions or a combination thereof.

8. The device of claim 1 further comprising a membrane that is impermeable to cells and permeable to molecules secreted by cells, wherein one side of the membrane is in contact with the one or more fluid channels, the one or more gel channels or a combination thereof.

9. The device of claim 8 further comprising a capture agent that specifically binds one or more molecules secreted by a cell, wherein the capture agent is on the opposite side of the membrane and cannot pass through the membrane.

10. The microfluidic device of claim 1, wherein
    a portion of each fluid channel is in contact with a region of the one or more gel cage regions and the remaining portion of each fluid channel extends away from the one or more gel cage region.

11. The device of claim 10 which comprises three or more fluid channels and one gel cage region.

12. The device of claim 11 wherein the one or more the fluid channels are in the shape of a "C", a "V", a "U" or combinations thereof, wherein a middle region of each fluid channel contacts the gel cage region and each end of each fluid channel extends away from the gel cage region.

13. The microfluidic device of claim 1 comprising a first fluid channel and a second fluid channel of the one or more fluid channels, and
an elliptical gel cage region;
wherein
one side of the elliptical gel cage region is flanked by the first fluid channel thereby creating a first gel cage region-fluid channel interface, and the other side of the elliptical gel cage region is flanked by the second fluid channel thereby creating a second gel cage region-fluid channel interface; and
the elliptical gel cage region comprises two parallel rows of posts centrally located in the elliptical gel cage region, thereby creating a central gel chamber; a row of posts arranged in a semicircle along the first gel cage region-fluid channel interface, thereby creating a first gel chamber that flanks one side of the central gel chamber on one side; and a row of posts arranged in a semicircle at the second gel cage region-fluid channel interface, thereby creating a second gel chamber that flanks the other side of the central gel chamber.

14. The device of claim 13 wherein the central gel cage region, the first gel chamber, the second gel chamber or a combination thereof further comprises tissue.

15. The device of claim 5 comprising at least three fluid channels, wherein the first gel cage region, the second gel cage region and the third gel cage region are arranged in series to one another in the device.

16. A method of making the device of claim 1 comprising:
a) etching one or more fluid channels and one or more gel cage regions into a first portion of the optically transparent material and creating one or more inlets to allow flow through the one or more fluid channels and the one or more gel cage regions, thereby creating a roof and walls of the device; and
b) bonding the first portion of the optically transparent material to a second portion of the optically transparent material that forms a floor of the device.

17. A method of identifying whether an agent is angiogenic or anti-angiogenic comprising:
a) introducing an agent to be assessed into the one or more fluid channels of the device of claim 1, wherein one or more fluid channels of the device comprises endothelial cells and one or more gel cage regions of the device comprises a gel that forms a gel region within the gel cage region of the device; and
b) maintaining the device under conditions in which the endothelial cells are encouraged to adhere to the gel region at the one or more gel cage region-fluid channel interface regions; and
c) determining whether creation of create cone-like protrusions that are lined with endothelial cells into the gel region are enhanced or inhibited in the presence of the agent compared to a control;
wherein if creation of cone-like protrusions that are lined with endothelial cells into the gel region is enhanced in the presence of the agent compared to the control, then the agent is angiogenic, and if creation of cone-like protrusions that are lined with endothelial cells into the gel is inhibited in the presence of the agent compared to the control, then the agent is anti-angiogenic.

18. A method of identifying whether an agent can be used to metastasis comprising:
a) introducing an agent to be assessed into the one or more fluid channels of the device of claim 1, wherein one or more fluid channels of the device comprises endothelial cells, one or more fluid or gel cage regions of the device comprise cancer cells, and one or more cage regions of the device comprises a gel that forms a gel region in the gel cage region of the device; and
b) maintaining the device under conditions in which the endothelial cells are encouraged to adhere to the gel region at the one or more gel cage region-fluid channel interface regions, thereby forming an endothelial layer of cells; and
c) determining whether the cancer cells disperse in the gel, migrate toward and across the endothelial layers of cells or a combination thereof in the presence of the agent;
wherein if the cancer cells have not dispersed in the gel, migrated toward the and across the endothelial layer of cells or a combination thereof, then this indicates that the agent can be used to inhibit metastasis.

19. The method of claim 18 wherein the cancer cells are dissociated cells from a cancer patient's cancer biopsy.

20. A method of growing blood vessels in vitro comprising:
a) introducing endothelial cells into one or more fluid channels of the device, wherein one or more gel cage regions of the device further comprises a gel that forms a gel cage therein; and
b) maintaining the device under conditions in which the endothelial cells are encouraged to adhere to the gel cage at the gel cage region-fluid channel interface region and create cone-like protrusions that are lined with endothelial cells into the gel cage, thereby growing blood vessels in vitro.

21. A method of identifying whether an agent is chemoattractive agent or a chemorepulsive agent of neuronal cells comprising:
a) introducing an agent to be assessed and neuronal cells into the one or more fluid channels of the device of claim 1, the one or more gel cage regions of the device of claim 1, or a combination thereof; wherein the one or more cage regions of the device comprises a gel that forms a gel region within the gel cage region of the device; and
b) maintaining the device under conditions in which the neuronal cells proliferate in the gel cage region; and
c) determining whether the neuronal cells proliferate toward the agent or away from the agent;
wherein if the neuronal cells proliferate toward the agent, then the agent is a chemoattractive agent of neuronal cells, and if the neuronal cells proliferate away from the agent, then the agent is a chemorepulsive agent of neuronal cells.

22. A method of identifying whether an agent can be used to treat cancer comprising:
a) introducing an agent to be assessed into the one or more fluid channels of the device of claim 1, wherein one or more gel cage regions of the device comprises a gel that forms one or more gel cages, and the gel cage further comprises a biopsy of a cancerous tissue; and
b) determining whether motility of the cancerous tissue is inhibited in the presence of the agent;
wherein if motility of the cancerous tissue is inhibited, then the agent can be used to treat cancer.

* * * * *

UNITED STATES PATENT AND TRADEMARK OFFICE
CERTIFICATE OF CORRECTION

| | | |
|---|---|---|
| PATENT NO. | : 9,261,496 B2 | |
| APPLICATION NO. | : 13/876293 | |
| DATED | : February 16, 2016 | |
| INVENTOR(S) | : Kamm et al. | |

It is certified that error appears in the above-identified patent and that said Letters Patent is hereby corrected as shown below:

In the claims

In Claim 3, Column 53, line 50, delete "v)".

Signed and Sealed this
Nineteenth Day of April, 2016

Michelle K. Lee
*Director of the United States Patent and Trademark Office*